(12) United States Patent
Awasthi et al.

(10) Patent No.: US 9,359,196 B2
(45) Date of Patent: Jun. 7, 2016

(54) ANTIPROLIFERATIVE COMPOSITIONS COMPRISING CURCUMIN ANALOGS AND METHODS OF PRODUCING AND USING SAME

(75) Inventors: Vibhudutta Awasthi, Edmond, OK (US); Pallavi Lagisetty, Glen Allen, VA (US); Hrushikesh Agashe, Pittsburg, PA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1029 days.

(21) Appl. No.: 13/279,766

(22) Filed: Oct. 24, 2011

(65) Prior Publication Data

US 2012/0288555 A1    Nov. 15, 2012

Related U.S. Application Data

(63) Continuation-in-part of application No. 13/168,534, filed on Jun. 24, 2011, now abandoned, and a continuation-in-part of application No. 12/556,906, filed on Sep. 10, 2009, now Pat. No. 8,420,118.

(60) Provisional application No. 61/359,536, filed on Jun. 29, 2010.

(51) Int. Cl.

| | |
|---|---|
| *C07D 211/44* | (2006.01) |
| *A61K 9/127* | (2006.01) |
| *A61K 31/444* | (2006.01) |
| *A61K 31/724* | (2006.01) |
| *A61K 31/4412* | (2006.01) |
| *B82Y 5/00* | (2011.01) |
| *A61K 47/48* | (2006.01) |
| *C08B 37/16* | (2006.01) |
| *C08L 5/16* | (2006.01) |
| *A61K 31/198* | (2006.01) |
| *A61K 31/45* | (2006.01) |
| *A61K 9/00* | (2006.01) |

(52) U.S. Cl.
CPC ............... *B82Y 5/00* (2013.01); *A61K 31/198* (2013.01); *A61K 31/45* (2013.01); *A61K 31/724* (2013.01); *A61K 47/48969* (2013.01); *C08B 37/0015* (2013.01); *C08L 5/16* (2013.01); *A61K 9/0019* (2013.01); *A61K 9/1272* (2013.01)

(58) Field of Classification Search
CPC ........................................................ A61K 9/127
USPC ........................................................ 424/450
See application file for complete search history.

(56) References Cited

U.S. PATENT DOCUMENTS

| | | | |
|---|---|---|---|
| 6,664,272 | B2 | 12/2003 | Snyder et al. |
| 7,371,766 | B2 | 5/2008 | Snyder et al. |

(Continued)

OTHER PUBLICATIONS

Lagisetty et al in Bioorganic & Medicinal Chemistry, vol. 18 (16), pp. 6109-6120, 2010.*

(Continued)

*Primary Examiner* — Gollamudi Kishore
(74) *Attorney, Agent, or Firm* — Dunlap Codding, P.C.

(57) ABSTRACT

Antiproliferative compositions that include CLEFMA, as well as liposomal compositions containing said antiproliferative compositions, are disclosed. Also disclosed are methods of making and using the antiproliferative compositions and liposomal compositions.

11 Claims, 24 Drawing Sheets
(11 of 24 Drawing Sheet(s) Filed in Color)

(56) References Cited

U.S. PATENT DOCUMENTS

| | | | |
|---|---|---|---|
| 2001/0051184 A1* | 12/2001 | Heng | A61K 9/0014 424/461 |
| 2004/0009914 A1 | 1/2004 | Shoji et al. | |
| 2005/0069551 A1 | 3/2005 | Shoji et al. | |
| 2005/0181036 A1* | 8/2005 | Aggarwal | A61K 9/0078 424/450 |
| 2006/0229239 A9 | 10/2006 | Shoji et al. | |
| 2007/0270464 A1 | 11/2007 | Liotta et al. | |
| 2008/0138400 A1* | 6/2008 | Kurzrock | A61K 9/1271 424/450 |
| 2008/0234320 A1 | 9/2008 | Snyder et al. | |
| 2009/0011991 A1 | 1/2009 | Shoji et al. | |

OTHER PUBLICATIONS

Pallavi et al., "An Anti-Proliferative Curcuminoid from Structure Activity Relationship Studies on 3,5-bis (benzylidene)-4-piperidones", Ref Works 210-06-22T20:27:53Z.

* cited by examiner compound 1 (EF24)

Scheme 1

1. R' = F, R = R" = H
2. R' = R" = R = H
3. R' = Cl, R" = R = H
4. R' = Br, R" = R = H
5. R' = NO₂, R" = R = H

6. R = Cl, R' = R" = H
7. R' = R = H, R" = F
8. R' = R = H, R" = Cl
9. R' = R = H, R" = N(CH₃)₂

Scheme 2

Conditions: i) NaBH₄, Ethanol, Room Temperature, 1 h ii) Pd/C/H₂, 1 atm, Room Temperature, 16 h Scheme 3

Conditions: (i) HCOOH, Acetic anhydride, Room Temp, 24 h (ii) Pyridine, Acetic anhydride, Room Temp, 16 h
(iii) Pyridine, Tosyl Chloride, Room Temp, 16 h (iv) Succinic anhydride, Triethylamine, 2 h
(v) N-hydroxysuccinimide, Dicyclohexylcarbodiimide, Dimethylformamide, Room Temp, 18 h
(vi) Glucosamine, Pyridine, 90 °C, 3 h (vii) $Cs_2CO_3$, KI, DMF, 85 °C, 1 h Conditions: (i) Succinic anhydride, Triethylamine, Room Temp, 2 h
(ii) Dicyclohexylcarbodiimide, N-hydroxysuccinimide, Room Temp, 16 h
(iii) Hexadecylamine, Py, 90 °C, 3h (iv) Stearoyl chloride, Triethylamine, Room Temp, 16 h
(v) long chain dicarboxylacid anhydride, Triethylamine, Room Temp, 2 h

ANTIPROLIFERATIVE COMPOSITIONS COMPRISING CURCUMIN ANALOGS AND METHODS OF PRODUCING AND USING SAME

CROSS REFERENCE TO RELATED APPLICATIONS

This application is a continuation-in-part of U.S. Ser. No. 13/168,534, filed Jun. 24, 2011, now abandoned; which claims benefit under 35 U.S.C. 119(e) of provisional application U.S. Ser. No. 61/359,536, filed Jun. 29, 2010. Said '534 application is also a continuation-in-part of U.S. Ser. No. 12/556,906, filed Sep. 10, 2009 now U.S. Pat. No. 8,420,118. The entire contents of the above-referenced patents and patent applications are hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Invention

The presently disclosed and claimed inventive concept(s) relates generally to compositions having antiproliferative activity, and in particular, but not by way of limitation, to compositions comprising curcumin analogs that possess antiproliferative activity, and methods of producing and using same.

2. Description of the Background Art

Cancer remains a challenging health care problem. Chemotherapeutic drugs are the mainstay in managing patients diagnosed with any form of cancer. Among various malignancies, pancreatic and lung cancers are the leading cause of cancer deaths in the world. For instance, in the United States of America an estimated 160,390 deaths in 2007 were attributed to lung cancer. About 6 out of 10 people with lung cancer die within one year of being diagnosed with the disease. In non-small cell lung carcinoma (NSCLC), which histologically includes adenocarcinoma, squamous cell carcinoma, and large cell carcinoma, surgery is the only curative treatment modality. Meta-analysis of clinical data suggests that up to 85% of the NSCLC patients depend on systemic chemotherapy as part of the overall management. Similarly, pancreatic adenocarcinoma is one of the most lethal cancers, with most patients dying of their disease within one year. The currently available U.S. Food and Drug Administration-approved treatments for this disease are gemcitabine and erlotinib, both of which produce responses only in a minority of patients, and their effect on survival is minimal. In light of the inefficacy of current standard of care in cancer chemotherapy, development of better therapies for pancreatic and lung cancer is of contemporary interest.

Chalcones are open-chain molecules where two aromatic rings flank a three-carbon enone fragment on either side. Curcumin, (1E,6E)-1,7-bis(4-hydroxy-3-methoxyphenyl) hepta-1,6-diene-3,5-dione, is a naturally occurring bis-chalcone derivative present in *Curcuma longa* Linn, a commonly used Indian spice turmeric. Studies have shown that curcumin has potent anti-angiogenic, anti-cancer properties. Although several in vitro investigations and pre-clinical studies have demonstrated immense potential of curcumin in cancer treatment, its clinical application has been found limited by its instability and poor bioavailability. As such, to improve the spectrum of activity as well as to modify pharmaceutical properties, several structurally-related compounds have been synthesized and evaluated as anti-proliferative and anti-infective agents. See, for example, Adams et al., 2004; Du et al., 2006; Modzelewska et al., 2006; and Robinson et al., 2005. A few curcumin analogs act as anti-inflammatory molecules by inhibiting cyclooxygenase-2 (COX-2) activity. Incidentally, COX-2 is also over-expressed in many malignant tissues. Curcumin has also been found to have beneficial effects in Alzheimer's disease.

3,5-Bis(2-fluorobenzylidene)-4-piperidone (also known as EF24) is a synthetic analog of curcumin that has been shown to possess potent antiproliferative activity against a number of cancer cell lines such as colon, breast and ovarian cell lines. Like curcumin, the exact mechanism of action of EF24 is unclear, but it appears to suppress cancer cell proliferation and angiogenesis by downregulating various cancer promoting genes such as COX-2, IN-8 and VEGF. It has also been found to induce G2/M cell cycle arrest and apoptosis in cisplatin-resistant human cancer cells. A recent study suggests that EF24 suppresses NF-kB signaling by directly inhibiting I-kB kinase. Chemically, it has been proposed that conjugated enones inhibit glutathione-S-transferase, which enhances the cytotoxicity of these compounds. The enones permit addition of intracellular thiol compounds, such as glutathione, to the olefinic double bond. The addition product is capable of further reacting with cellular nucleophiles, and consequently contributes to the cytotoxicity thereof. Definite evidence in favor of this hypothesis is still lacking.

Therefore, there is a need in the art for new and improved antiproliferative compositions. It is to said compositions, as well as methods of producing and using same, that the presently disclosed and claimed inventive concept(s) is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1(*b*) provides a general diagram of 3,5-bis(benzylidene)-4-piperidones showing regions (dotted lines) that were chemically modified.

DETAILED DESCRIPTION OF THE INVENTIVE CONCEPT(S)

Figure 1A:
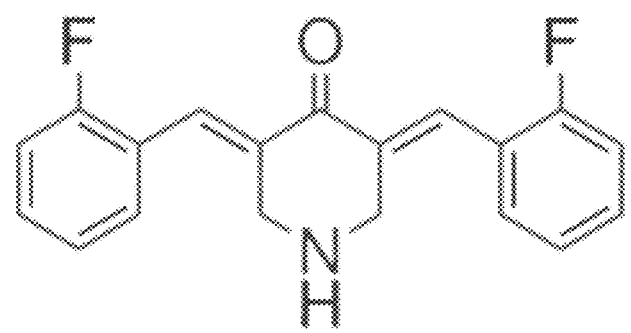
FIG. 1(*a*) illustrates the structure of 3,5-bis(2-fluorobenzylidene)-4-piperidone.

Before explaining at least one embodiment of the presently disclosed and claimed inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which this inventive concept(s) pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, or management of a disease and/or cancer. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

A "disorder" is any condition that would benefit from treatment with the polypeptide. This includes chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed inventive concept(s). This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed and claimed inventive concept(s) (and/or the methods of administration of same) may be designed to provide delayed, controlled or sustained release using formulation techniques which are well known in the art.

The presently disclosed and claimed inventive concept(s) also includes a pharmaceutical composition comprising a therapeutically effective amount of at least one of the compositions described herein in combination with a pharmaceutically acceptable carrier. As used herein, a "pharmaceutically acceptable carrier" is a pharmaceutically acceptable solvent, suspending agent or vehicle for delivering the compositions of the presently disclosed and claimed inventive concept(s) to the human or animal. The carrier may be liquid or solid and is selected with the planned manner of administration in mind. Examples of pharmaceutically acceptable carriers that may be utilized in accordance with the presently disclosed and claimed inventive concept(s) include, but are not limited to, PEG, liposomes, ethanol, DMSO, aqueous buffers, oils, and combinations thereof.

The terms "liposome", "lipid nanostructure" and "vesicle" may be used interchangeably herein and will be understood to refer to an assembled structure constructed of molecules such as lipids and/or proteins, for example, not through covalent bonds but through interactions (such as but not limited to, hydrophobic interactions, electrostatic interactions and hydrogen bonds) acting between the molecules in an aqueous medium.

The terms "aqueous solution" and "aqueous medium" will be used interchangeably herein and will be understood to refer to water as well as any kind of solution which is physiologically acceptable and solvent in water.

The terms "imaging agent" and "labeling moiety" are used interchangeably herein and will be understood to refer to any agent/moiety that allows for detection of said imaging agent/labeling moiety by any methods known in the art. For example but not by way of limitation, the imaging agents contemplated for use in accordance with the presently disclosed and claimed inventive concept(s) may be radiolabels detectable by molecular imaging, x-ray and/or PET, or may be a gas for detection by ultrasound, or may be a gadolinium chelate derivative for detection by magnetic resonance imaging (MRI), or may be a fluorophore for detection by fluoroscopy, or may be any agents known in the art for detection by computerized tomography (CT), dual source CT (perfusion imaging), diffusion tensor imaging (DTI), delayed enhanced imaging, and computerized SPECT, or may be any combination thereof.

The terms "targeting molecule" and "targeting moiety" are used interchangeably herein and will be understood to refer to any molecule/moiety that specifically recognizes a biomarker present on a cell to be targeted, thus direct the delivery of the compositions described herein to said cell. For example but not by way of limitation, targeting molecules that may be utilized in accordance with the presently disclosed and claimed inventive concept(s) include antibodies and antibody fragments, small and large molecule ligands of known receptors and antigens, and combinations thereof. Targeting molecules are well known in the art, and a person having ordinary skill in the art will readily understand how to select a particular targeting molecule and incorporate same into the compositions described herein; therefore, no further description of said targeting molecules is required.

Turning now to the presently disclosed and claimed inventive concept(s), said inventive concept(s) are directed in general to compositions comprising a derivative of a diphenyldifluoroketone (such as but not limited to, 3,5-bis-(2-fluorobenzylidene)-4-piperidone or EF24). Said derivative may comprise a chloro substitution in an aromatic ring thereof, and may further comprise an unsaturated maleic acid N-substitution in a piperidone ring thereof.

In one embodiment, the composition of the presently disclosed and claimed inventive concept(s) comprises 4-[3,5-bis(2-chlorobenzylidene-4-oxo-piperidine-1-yl)-4-oxo-2-butenoic acid] (CLEFMA).

In certain embodiments, the composition of the presently disclosed and claimed inventive concept(s) may include at least one additional molecule/agent. For example but not by way of limitation, the composition may include a solubilization agent (such as but not limited to, HPβCD), an imaging agent (such as but not limited to, a radiolabel), a targeting molecule (for targeting delivery of the composition to particular cell(s), i.e., a cancer-specific ligand for targeted cytotoxicity), an anti-cancer agent, an anti-inflammatory agent, an anti-oxidant, a Cox-2 inhibitor, a targeting moiety, a coating molecule, a labeling moiety, and combinations thereof.

The presently disclosed and claimed inventive concept(s) further includes a method of producing the antiproliferative composition described herein above. Said method may comprise any of the steps described in the attached Invention Disclosure and manuscripts.

The compositions of the presently disclosed and claimed inventive concept(s) may be prepared according to methods known in the art, particularly in light of the disclosure and examples set forth herein. The starting materials used to synthesize the compositions of the presently disclosed and claimed inventive concept(s) are commercially available or capable of preparation using methods known in the art.

The presently disclosed and claimed inventive concept(s) further includes a pharmaceutical composition comprising an antiproliferative agent as described herein above.

The presently disclosed and claimed invention is also directed to a method of using the pharmaceutical composition described herein above. Said method may include the steps of providing the pharmaceutical composition comprising an antiproliferative composition as described herein above, and administering an effective amount of the pharmaceutical composition to a patient in need thereof.

The presently disclosed and claimed inventive concept(s) is also directed to a method of inhibiting growth of at least one tumor cell, comprising the step of exposing the at least one tumor cell to an effective amount of the antiproliferative composition described herein above.

The presently disclosed and claimed inventive concept(s) is further directed to a method of inducing tumor cell death in vivo. The method includes the step of contacting a population of tumor cells in vivo with a therapeutically effective amount of the antiproliferative composition described herein above.

The presently disclosed and claimed inventive concept(s) is also directed to a method of treating cancerous tissue in a subject, comprising administering an effective amount of the antiproliferative composition described herein above.

The presently disclosed and claimed inventive concept(s) is further directed to a method of inhibiting and/or preventing growth of a cancer. Said method comprises administering an effective amount of an antiproliferative composition as described in detail herein above to a subject suffering from or predisposed to cancer, thereby inhibiting and/or preventing growth of the cancer.

The presently disclosed and claimed inventive concept(s) is further directed to a method of decreasing the occurrence and/or severity of cancer/tumorigenesis. Said method comprises administering an effective amount of an antiproliferative composition as described in detail herein above to a subject suffering from or predisposed to cancer/tumorigenesis, thereby inhibiting and/or preventing cancer/tumorigenesis.

The presently disclosed and claimed inventive concept(s) is further directed to a method of selectively targeting a specific pathophysiology. Said method comprises administering an effective amount of an antiproliferative composition as described in detail herein above to a subject suffering from or predisposed to said specific pathophysiology, thereby inhibiting, decreasing the occurrence of and/or preventing said pathophysiology. For example but not by way of limitation, the administration of the antiproliferative composition may result in increased production of reactive oxygen species and/or activation of Nrf2-mediated oxidative stress response.

The presently disclosed and claimed inventive concept(s) is further related to a liposome or other lipid nanostructure having the antiproliferative compositions described herein above encapsulated therein. In one embodiment, the liposome or other lipid nanostructure may comprise a lipid composition having the structure represented by the following general formula [Subramaniam et al., 2008]:

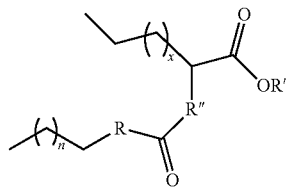

wherein R is NH or O; R' is at least one of a hydrogen (H), an alkyl group (such as but not limited to, methyl, ethyl, propyl, butyl, pentyl, hexyl, heptyl, octyl, nonyl, decyl, undecyl, dodecyl, hexadecyl), Na, Li, K, a metal, or a halogen; R" is at least one of a —CH$_2$— group and a —CH$_2$CH$_2$-group; and n and x are each an 8-16 carbon chain that may be saturated or unsaturated, and that may or may not contain additional functional groups. In one embodiment, the lipid is asymmetrical. Examples of said lipid compositions include, but are not limited to, 2-carboxyheptadecanoyl heptadecylamide (CHHDA); 1,4-dipalmitoyl-tartarate-2,3-disuccinic acid (DPTSA); 1,4-dipalmitoyl-tartarate-2,3-diglutaric acid (DPTGA); 1,4-disteroyl-tartarate-2,3-disuccinic acid (DSTSA); and cholesteryl hemisuccinate (CHEMS).

Said liposome or other lipid nanostructure may further include other lipids, such as but not limited to, phospholipids.

Specific examples of other lipids that may be utilized in accordance with the presently disclosed and claimed inventive concept(s) include, but are not limited to, at least one phosphatidylcholine, such as but not limited to, 1,2-disteroyl-sn-glycero-3-phosphatidylcholine (DSPC) and dipalmitoyl phosphatidylcholine (DPPC); at least one phosphoethanolamine, such as but not limited to, 1,2-disteroyl-sn-glycero-3-phosphatidylethanolamine (DSPE); at least one phosphatidylglycerol, such as but not limited to, dimyristoylphosphatidyl glycerol (DMPG); at least one sterol lipid, such as but not limited to, cholesterol; at least one vitamin, such as but not limited to, vitamin E; and the like. In one embodiment, the anionic non-phospholipid may comprise 1% to 30% of the total lipid present in the liposome/lipid nanostructure. In another embodiment, any phospholipid present in the liposome/lipid nanostructure will be in the range of from 30% to 99% of the total lipid present in the liposome/lipid nanostructure, so as to minimize any toxicity of the liposome/lipid nanostructure.

The liposome/lipid nanostructure may also include at least one additional molecule/agent. For example but not by way of limitation, the liposome/lipid nantostructure may include a solubilization agent (such as but not limited to, HP(3CD), glutathione, an imaging agent (such as but not limited to, a radiolabel), a targeting molecule (for targeting delivery of the composition to particular cell(s), i.e., a cancer-specific ligand for targeted cytotoxicity), an anti-cancer agent, an anti-inflammatory agent, an anti-oxidant agent, a Cox-2 inhibitor, a coating molecule, and combinations thereof.

The liposome/lipid nanostructure may be provided with any particle size that will allow the liposome/lipid nanostructure to function in accordance with the presently disclosed and claimed inventive concept(s). In one embodiment, the liposome/lipid nanostructure may be provided with a particle size in a range of from about 50 nm to about 500 nm, such as but not limited to, about 200 nm to about 300 nm; in addition, the liposome/lipid nanostructure may be provided with a volume average particle size in a range of from about 10 nm to about 5,000 nm.

The lipids and liposome/lipid nanostructures formed therefrom in accordance with the presently disclosed and claimed inventive concept(s) are described in further detail in U.S. Ser. No. 12/556,906, which has previously been incorporated herein by reference. Said liposome/lipid nanostructures have several advantages of the prior art, including but not limited to, a decrease in toxicity as well as a decrease in expense. Negative phospholipids are toxic to cells at certain concentrations; because of the absence of the phosphate group from the compositions, the lipid (and thus the liposome/lipid nanostructures formed therefrom) does not induce untoward effects as commonly seen with liposomes containing anionic phospholipid. The '906 application demonstrates that the presence of the anionic non-phospholipid is not toxic to vascular endothelial cells nor to macrophages in culture, and that LEH preparations formed therefrom do not activate platelets in vitro. In addition, the lipid compositions are entirely synthetic and thus can be synthesized in large quantities using inexpensive raw materials and procedures. Further, the replacement of anionic phospholipids commonly used in liposome formulations with the anionic non-phospholipid compositions increases encapsulation and stability of the liposomal structures.

The liposome/lipid nanostructure may further comprise at least one additional moiety. Moieties that may be utilized in accordance with the presently disclosed and claimed inventive concept(s) include, but are not limited to: (1) a targeting moiety such as but not limited to antibodies and antibody fragments; as well as small and large molecule ligands of known receptors and antigens; (2) a coating molecule attached to any phospholipids present in the liposome/lipid nanostructure to decrease the charge effect thereof, such as but not limited to, polyethylene glycol (PEG); (3) a labeling moiety, such as but not limited to, moieties that allow radiolabeling of the liposome structure, including but not limited to, diethylenetriamine pentaacetic acid; and the like.

The presently disclosed and claimed inventive concept(s) further includes a pharmaceutical composition comprising a liposome/lipid nanostructure as described herein above having an antiproliferative agent as described herein above encapsulated therein.

The presently disclosed and claimed inventive concept(s) further includes a method of forming a liposome/lipid nanostructure having at least one antiproliferative composition (as described herein above) encapsulated therein. Such method includes the steps of providing at least one anionic non-phospholipid composition as described herein above, providing the antiproliferative composition, disposing the anionic non-phospholipid composition and the antiproliferative composition in an aqueous solution, and dispersing same to form the liposome/lipid nanostructure having the antiproliferative composition encapsulated therein. The dispersion may be accomplished as described herein above and in the '906 application. Alternatively, the anionic non-phospholipid composition may initially be dispersed to form a pro-liposome composition, and the pro-liposome composition mixed with the antiproliferative composition to encapsulate same and form the liposome/lipid nanostructure having the antiproliferative composition encapsulated therein.

The presently disclosed and claimed inventive concept(s) is also directed to a method of using the pharmaceutical composition described herein above. Said method includes the steps of providing the pharmaceutical composition comprising anionic non-phospholipid and antiproliferative composition as described herein above, and administering an effective amount of the pharmaceutical composition to a patient in need thereof.

The presently disclosed and claimed inventive concept(s) is also directed to a method of inhibiting growth of at least one tumor cell, comprising the step of exposing the at least one tumor cell to an effective amount of the liposome-encapsulated antiproliferative composition described herein above.

The presently disclosed and claimed inventive concept(s) is further directed to a method of inducing tumor cell death in vivo. The method includes the step of contacting a population of tumor cells in vivo with a therapeutically effective amount of the liposome-encapsulated antiproliferative composition described herein above.

The presently disclosed and claimed inventive concept(s) is also directed to a method of treating cancerous tissue in a subject, comprising administering an effective amount of the liposome-encapsulated antiproliferative composition described herein above.

The presently disclosed and claimed inventive concept(s) is further directed to a method of inhibiting and/or preventing growth of a cancer. Said method comprises administering an effective amount of the liposome-encapsulated antiproliferative composition as described in detail herein above to a subject suffering from or predisposed to cancer, thereby inhibiting and/or preventing growth of the cancer.

The presently disclosed and claimed inventive concept(s) is further directed to a method of decreasing the occurrence and/or severity of cancer/tumorigenesis. Said method comprises administering an effective amount of the liposome-encapsulated antiproliferative composition as described in detail herein above to a subject suffering from or predisposed to cancer/tumorigenesis, thereby inhibiting and/or preventing cancer/tumorigenesis.

The presently disclosed and claimed inventive concept(s) is further directed to a method of selectively targeting a specific pathophysiology. Said method comprises administering an effective amount of the liposome-encapsulated antiproliferative composition as described in detail herein above to a subject suffering from or predisposed to said specific pathophysiology, thereby inhibiting, decreasing the occurrence of and/or preventing said pathophysiology. For example but not by way of limitation, the administration of the liposome-encapsulated antiproliferative composition may result in increased production of reactive oxygen species and/or activation of Nrf2-mediated oxidative stress response.

Further, in certain embodiments of any of the methods described and/or claimed herein, the antiproliferative compositions (as well as liposome-encapsulated antiproliferative compositions) described herein do not substantially affect normal cells.

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

EXAMPLE 1

Despite the growing understanding about the molecular basis of oncogenesis, cancer remains a challenging health care problem. Chemotherapeutic drugs are the mainstay in managing patients diagnosed with any form of cancer. The emergent chemo-resistance, morbid toxicities and overall inefficacy of current drug portfolios in many cancers necessitate the development of new drugs with novel mechanism of action and selective action on cancer cells. Taking a cue from the recent findings that curcumin has tumor suppressive activity in a variety of cancers, [Levi-Ari et al., 2006; Subramaniam et al., 2008] the inventors preformed a structure activity relationship on synthetic diphenyldihaloketone analogs. [Subramaniam et al., 2008; Lagisetty et al., 2009] As a class, such compounds belong to chalcone group of chemicals. Chalcones are open-chain molecules where two aromatic rings flank a three-carbon enone fragment on either side. Curcumin, (1E,6E)-1,7-bis(4-hydroxy-3-methoxyphenyl) hepta-1,6-diene-3,5-dione, is a naturally occurring bis-chalcone derivative present in *Curcuma longa* Linn, a commonly used Indian spice turmeric. Studies have shown that curcumin has potent anti-angiogenic, anti-cancer properties. [Leyon et al., 2003] Although several in vitro investigations and pre-clinical studies have demonstrated immense potential of curcumin in cancer treatment, its clinical application has been found limited by its instability and poor bioavailability. [Anand et al, 2007] As such, to improve the spectrum of activity as well as to modify pharmaceutical properties, several structurally-related compounds have been synthesized and evaluated as anti-proliferative and anti-infective agents. [Adams et al, 2004; Du et al., 2006; Modzelewska et al., 2006; Robinson et al., 2005] A few curcumin analogs act as anti-inflammatory molecules by inhibiting cyclooxygenase-2 (COX-2) activity. Incidentally, COX-2 is also over-expressed in many malignant tissues. [Eberhart et al., 1994] In Alzheimer's disease also curcumin has been found to have beneficial effects. [Roberson et al., 2006]

3,5-Bis(2-fluorobenzylidene)-4-piperidone (also known as EF24) is a synthetic analog of curcumin that was first reported by Adams, et al. (2004). It has been shown to possess potent antiproliferative activity against a number of cancer cell lines such as colon, [Subramaniam et al., 2008] breast [Sun et al., 2006] and ovary [Selvendiran et al., 2007]. Like curcumin, the exact mechanism of action of EF24 is unclear, but it appears to suppress cancer cell proliferation and angiogenesis by downregulating various cancer promoting genes such as COX-2, IL-8 and VEGF [Subramaniam et al., 2008]. It has also been found to induce G2/M cell cycle arrest and apoptosis in cisplatin-resistant human cancer cells [Selvendiran et al., 2007]. A recent study suggests that EF24 suppresses NF-kB signaling by directly inhibiting I-kB kinase [Kasinski et al., 2008]. Chemically, it has been proposed that conjugated enones inhibit glutathione-5-transferase, which enhances the cytotoxicity of these compounds [O'Dwyer et al., 1994]. The enones permit a Michael addition of intracellular thiol compounds, such as glutathione, to the olefinic double bond. The addition products are capable of releasing the conjugated drug based on the reversible equilibrium existing between the conjugate and free drug [Adams et al., 2005; Costi et al., 2004; Pati et al., 2008; Sun et al., 2009].

Among various malignancies, lung cancers are the leading cause of cancer deaths in the world. For instance, in the United States of America an estimated 160,390 deaths in 2007 were attributed to lung cancer [Tsuboi et al., 2007]. About 6 out of 10 people with lung cancer die within 1 year of being diagnosed with the disease. In non-small cell lung carcinoma (NSCLC), which histologically includes adenocarcinoma, squamous cell carcinoma, and large cell carcinoma, surgery is the only curative treatment modality. [Burdett et al., 2007] Meta-analysis of clinical data suggests that up to 85% of the NSCLC patients depend on systemic chemotherapy as part of the overall management. [Akerley et al., 1999] The current standard of care for lung cancer produces unsatisfactory responses and inadequate improvement in survival. [Dubey et al., 2009] Since anti-cancer drugs remain the mainstay in the post-diagnosis management of lung cancer, broadening of the chemotherapeutic options is of contemporary interest.

In this Example, the results of structure activity relationship studies on 3,5-bis(benzylidene)-4-piperidones are described. The compounds were systematically evaluated for anti-proliferative activity in cultured lung adenocarcinoma cells. The lead compound, named CLEFMA, was preliminarily investigated for the molecular basis of anti-proliferative action. The information provides a sound basis for further chemical modifications of the core structure resulting in potentially more bioavailable and potent compounds amenable to improved formulation pharmaceutics.

Results and Discussion for Example 1

Chemistry

Figure 1B:
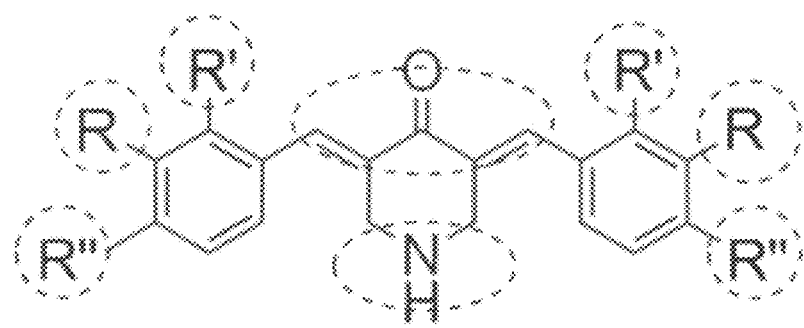

Several analogs of 3,5-bis(2-fluorobenzylidene)-4-piperidone, 1 (FIG. 1a), were synthesized and classified into five series, namely A, B, C, D and E as shown in Table 1 and FIG. 1b. The basic chemical reaction was Claisen-Schmidt condensation between 4-piperidone hydrochloride and substituted aromatic aldehydes (FIG. 2). [Adams et al., 2004] Single X-ray crystallography of 1 revealed that the olefinic double bonds adopts E configuration, and the central piperidone ring remains in a sofa conformation. [Lagisetty et al., 2009] This is consistent with the previously reported crystal structures for 3,5-bis(benzylidene)-4-piperidones and 2,6-bis (arylidene)cyclohexanones. [Dimmock et al., et al., 1999; Dimmock et al., 2002; Jia et al., 1988]

Figure 2:
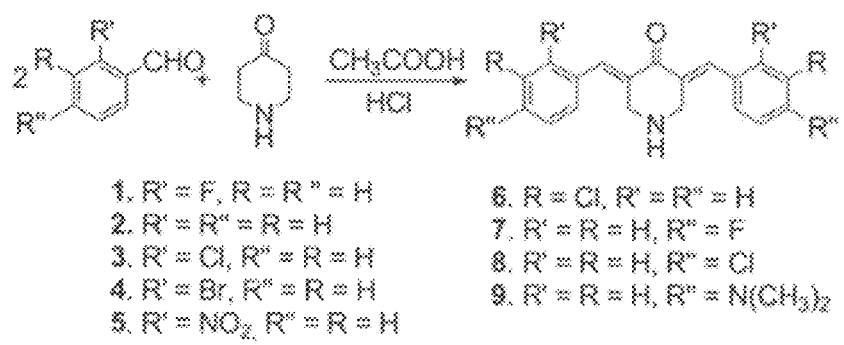
FIG. 2 illustrates the synthetic scheme for various 3,5-bis (benzylidene)-4-piperidones.

Series A compounds (aromatic ring substitutions): 3,5-Bis (benzylidene)-4-piperidones containing different substitutions on the two aromatic rings were synthesized in good yields (FIG. 2). Compounds 2-5 carry different ortho-substituents on their aromatic rings. Compound 6 has the substitution on meta-position, and compounds 7-9 bear substitution on para-position of the aromatic ring.

TABLE 1

Summary of synthesized 3,5-bis(benzylidene)-4-piperidone derivatives

| Compound | Chemical name | M.W. | M.P. (° C.) | Reaction Time(h) | % Yield | IC50 value (μM) |
|---|---|---|---|---|---|---|
| 1 | 3,5-Bis(2-fluorobenzylidene)-4-piperidone | 311.12 | 189-190 | 48 | 94 | 44 |
| 2 | 3,5-Bis(benzylidene)-4-piperidone | 275.12 | 179-180 | 48 | 85 | 12 |
| 3 | 3,5-Bis(2-chlorobenzylidene)-4-piperidone | 343.05 | 215-217 | 48 | 72 | 5 |
| 4 | 3,5-Bis(2-bromobenzylidene)-4-piperidone | 430.95 | 220-222 | 72 | 69 | 6 |
| 5 | 3,5-Bis(2-nitrobenzylidene)-4-piperidone | 365.10 | 223-225 | 72 | 72 | 93 |
| 6 | 3,5-Bis(3-chlorobenzylidene)-4-piperidone | 343.05 | 248-250 | 48 | 87 | 50 |
| 7 | 3,5-Bis(4-fluorobenzylidene)-4-piperidone | 361.13 | 208-210 | 48 | 89 | 45.67 |
| 8 | 3,5-Bis(4-chlorobenzylidene)-4-piperidone | 343.05 | 255-257 | 48 | 84 | 87 |
| 9 | 3,5-Bis[4-(N,N-dimethylaminoenzylidene)]-4-piperidone | 361.13 | 242-243 (decomp) | 48 | 81 | 101 |
| 10 | 3,5-Bis(2-fluorobenzylidene)-4-hydroxy-piperidine | 313.13 | 83-85 | 1 | 98 | 124 |
| 11 | 3,5-Bis(2-fluorobenzyl)-4-piperidone | 315.14 | 76-78 | 16 | 95 | 130 |
| 12 | 4-[3,5-bis(2-fluorobenzylidene)-4-oxo-piperidone-1-yl)-4-oxo-butanoic acid] | 411.13 | 141-143 | 2 | 92 | 69 |
| 13 | 4-[3,5-Bis-(2-fluorobenzylidene)-4-oxo-piperidin-1-yl]-4-oxo-2-butenoic acid | 409.38 | 102-103 | 2 | 84 | 29 |
| 14 | 2-[3,5-Bis-(2-fluorobenzylidene)-4-oxo-piperidin-1-yl]-2-oxo-ethoxyacetic acid | 427.13 | 145-146 | 2 | 52 | 310 |
| 15 | 5-[3,5-Bis-(2-fluorobenzylidene)-4-oxo-piperidin-1-yl]-5-oxo-pentanoic acid | 425.13 | 167-168 | 2 | 96 | 60 |
| 16 | 2-[3,5-Bis-(2-fluorobenzylidene)-4-oxo-piperidine-1-carbonyl]-benzoic acid | 459.13 | 196-198 | 2 | 93 | 56 |
| 17 | 2-[3,5-Bis-(2-fluorobenzylidene)-4-oxo-piperidine-1-carbonyl]-cyclohexanecarboxylic acid | 465.18 | 96-98 | 2 | 88 | 55 |
| 18 | N-Formyl-3,5-bis(2-fluorobenzylidene)-4-piperidone | 339.11 | 164-165 | 16 | 45 | 49 |
| 19 | N-Acetyl-3,5-bis(2-fluorobenzylidene)-4-piperidone | 353.13 | 132-134 | 16 | 91 | 54 |
| 20 | N-(4-Methylbenzenesulfonyl)-3,5-bis(2-fluoro benzylidene)-4-piperidone | 465.12 | 162-163 | 16 | 86 | 50 |
| 22 | 4-Oxo-4-[3,5-bis(2-fluorobenzylidene-4-piperidonylcarbonyl)-2-glucose propanamide] | 572.20 | 148-150 | 3 | 68 | 79 |
| 23 | 2-[3,5-Bis(2-fluorobenzylidene-4-piperidone-1-yl]-N-(4-fluorobenzyl)acetamide] | 476.16 | 115-117 | 1 | 53 | 46 |
| 24 | 4-[3,5-Bis-(2-fluorobenzylidene)-4-oxo-piperidin-1-yl]-N-hexadecyl-4-oxo-butyramide | 634.20 | 60-62 | 3 | 59 | 64 |
| 25 | 3,5-Bis-(2-fluorobenzylidene)-1-octadecanoyl-4-piperidone | 577.40 | 70-71 | 16 | 67 | Not done |
| 26 | 3-[3,5-Bis-(2-fluorobenzylidene)-4-oxo-piperidine-1-carbonyl]-pentadec-4-enoic acid | 577.29 | 48-50 | 2 | 95 | 58 |
| 27 | 3-[3,5-Bis-(2-fluorobenzylidene)-4-oxo-piperidine-1-carbonyl]-heptadec-4-enoic acid | 605.33 | Thick syrup | 2 | 92 | 47 |
| 28 | 3-[3,5-Bis-(2-fluorobenzylidene)-4-oxo-piperidine-1-carbonyl]-heneicos-4-enoic acid | 661.39 | Thick syrup | 2 | 93 | 84 |
| 29 | 4-[3,5-Bis-(2-chlorobenzylidene)-4-oxo-piperidin-1-yl]-4-oxo-2-butenoic acid | 441.05 | 98-99 | 0.5 | 94 | 1 |

TABLE 2

Synthesis details for Series B compounds

| Compound | Reactant 1 | Reactant 2 | Yield | Characteristics |
|---|---|---|---|---|
| 4.1.2. [3,5-Bis-(benzylidene)-4-piperidone] (2) | 4-Piperidone hydrochloride monohydrate (1.35 g, 8.79 mmol) | Benzaldehyde (2.03 ml, 19.80 mmol) | 85% (2.1 g) | $^1$H NMR (300 MHz, DMSO-d6): δ 7.90 (s, 2H, C=CH), 7.50-7.40 (m, 10H, Ar—H), 4.50 (s, 4H). $^{13}$C NMR (75 MHz, DMSO-d6): δ 170.31, 139.92, 130.76, 130.39, 123.52, 114.15, 44.12. ESI Mass calculated for $C_{19}H_{18}NO$ (M + H)$^+$ 276.14, found 276.15. |
| 4.1.3. [3,5-Bis(2-chlorobenzylidene)-4-piperidone] (3) | 4-Piperidone hydrochloride monohydrate (0.80 g, 5.20 mmol) | 2-Chloro-benzaldehyde (1.33 ml, 11.8 mmol) | 72% (1.3 g) | $^1$H NMR (300 MHz, DMSO-d6): δ 10.00 (s, 1H, NH), 7.97 (s, 2H, C=CH), 7.70-7.60 (m, 2H, Ar—H), 7.55-7.40 (m, 6H, Ar—H), 4.34 (s, 4H). $^{13}$C NMR (75 MHz, DMSO-d6): δ 172.10, 136.30, 134.54, 132.14, 132.06, 131.27, 130.42, 130.14, 127.99, 113.93, 44.06. ESI Mass calculated for $C_{19}H_{16}Cl_2NO$ (M + H)$^+$ 344.06, found 344.00. |

TABLE 2-continued

Synthesis details for Series B compounds

| Compound | Reactant 1 | Reactant 2 | Yield | Characteristics |
|---|---|---|---|---|
| 4.1.4. [3,5-Bis(2-bromo-benzylidene)-4-piperidone] (4) | 4-Piperidone hydrochloride monohydrate (0.80 g, 5.20 mmol) | 2-Bromo-benzaldehyde (1.24 ml, 10.40 mmol) | 69% (1.6 g) | $^1$H NMR (300 MHz, DMSO-d6): δ 9.86 (s, 1H), 7.94 (s, 2H, C=CH), 7.84-7.82 (m, 2H, Ar—H), 7.60-7.39 (m, 6H, Ar—H), 4.34 (s, 4H). $^{13}$C NMR (75 MHz, DMSO-d6): δ 173.30, 133.88, 133.62, 129.79, 128.51, 125.12, 107.42, 42.50. ESI Mass calculated for $C_{19}H_{16}Br_2NO$ $(M + H)^+$ 434.14, found 434.00. |
| 4.1.5. [3,5-Bis(2-nitrobenzylidene)-4-piperidone] (5) | 4-Piperidone hydrochloride monohydrate (0.40 gm, 2.60 mmol) | 2-Nitro-benzaldehyde (0.80 gm, 5.20 mmol) | 72% (0.7 g) | $^1$H NMR (300 MHz, DMSO-d6): δ 9.65 (s, 1H), 8.28 (d, 2H, Ar—H, J = 7.5), 8.15 (s, 2H, C=CH), 7.89 (t, 2H, Ar—H, J = 7.6), 7.77 (t, 2H, Ar—H, J = 7.6), 7.56 (d, 2H, Ar—H, J = 7.6), 4.21 (s, 4H). $^{13}$C NMR (75 MHz, DMSO-d6): δ 172.48, 147.87, 137.97, 134.87, 131.25, 131.13, 130.09, 129.09, 125.73, 43.87. ESI Mass calculated for $C_{19}H_{16}N_3O_5$ $(M + H)^+$ 366.11, found 366.10. |
| 4.1.6. [3,5-Bis(3-chlorobenzylidene)-4-piperidone] (6) | 4-Piperidone hydrochloride monohydrate (0.70 gm, 4.55 mmol) | 3-Chloro-benzaldehyde (1.58 ml, 9.10 mmol) | 87% (1.4 g) | $^1$H NMR (300 MHz, DMSO-d6): δ 10.05 (s, 1H), 7.82 (s, 2H, C=CH), 7.61 (s, 2H, Ar—H), 7.60-7.40 (m, 6H, Ar—H), 4.41 (s, 4H). $^{13}$C NMR (75 MHz, DMSO-d6): δ 174.10, 137.10, 134.30, 133.04, 131.08, 130.43, 129.98, 128.96, 112.98, 44.40. ESI Mass calculated for $C_{19}H_{16}Cl_2NO$ $(M + H)^+$ 344.06, found 344.09. |
| 4.1.7. [3,5-Bis(4-fluorobenzylidene)-4-piperidone] (7) | 4-Piperidone hydrochloride monohydrate (0.78 gm, 5.08 mmol) | 4-Fluoro-benzaldehyde (1.10 ml, 10.20 mmol) | 89% (1.4 g) | $^1$H NMR (300 MHz, DMSO-d6): δ 9.93 (s, 1H), 7.87 (s, 2H, C=CH), 7.70-7.59 (m, 4H, Ar—H), 7.43-7.34 (m, 4H, Ar—H), 4.46 (s, 4H). $^{13}$C NMR (75 MHz, DMSO-d6): δ 172.47, 163.23 (d, J = 249.6), 138.40, 133.51 (d, J = 3.9), 130.76, 128.08, 116.47 (d, J = 21.6), 44.05. ESI Mass calculated for $C_{19}H_{16}F_2NO$ $(M + H)^+$ 312.12, found 312.12 |
| 4.1.8. [3,5-Bis(4-chlorobenzylidene)-4-piperidone] (8) | 4-Piperidone hydrochloride monohydrate (0.80 gm, 5.20 mmol) | 4-Chloro-benzaldehyde (1.41 gm, 10.42 mmol) | 84% (1.5 g) | $^1$H NMR (300 MHz, DMSO-d6): δ 10.07 (s, 1H, NH), 7.83 (s, 2H, C=CH), 7.60-7.45 (m, 8H, Ar—H), 4.43 (s, 4H). $^{13}$C NMR (75 MHz, DMSO-d6): δ 172.31, 138.35, 135.24, 133.01, 132.75, 129.44, 128.87, 44.10. ESI Mass calculated for $C_{19}H_{16}Cl_2NO$ $(M + H)^+$ 344.06, found 344.07. |
| 4.1.9. [3,5-Bis(4-dimethylamino-benzylidene)-4-piperidone] (9) | 4-Piperidone hydrochloride monohydrate (0.30 gm, 1.95 mmol) | 4-Dimethyl-aminobenzaldehyde (0.58 gm, 3.91 mmol) | 81% (0.6 g) | $^1$H NMR (300 MHz, DMSO-d6): δ 9.16 (s, 1H, NH), 7.76 (s, 2H, C=CH), 7.38 (d, 4H, Ar—H, J = 9.1), 6.82 (d, 4H, Ar—H, J = 9.1), 4.74 (s, 4H), 3.02 (s, 12H). ESI Mass calculated for $C_{23}H_{28}N_3O$ $(M + H)^+$ 362.22, found 362.13. |

TABLE 3

Synthesis details for series C compounds

| Particulars | NMR | Mass |
|---|---|---|
| 4.3.1. 4-Oxo-4-[3,5-bis(2-fluoro-benzylidene-4-piperidone-1-yl) butanoic acid] (12): Succinic anhydride (107 mg, 1.07 mmol) was reacted with 1, (320 mg, 1.02 mmol) in triethylamine (0.28 ml, 1.99 mmol) to obtain 12 as yellow amorphous solid in 92% yield (391 mg). $R_f = 0.31$ | $^1$H NMR (400 MHz, CDCl$_3$): δ 9.63 (br s, 1H, COOH), 7.87, 7.84 (s, 2H, C=CH), 7.40-7.10 (m, 8H, Ar—H), 4.75, 4.57 (2s, 4H), 2.49 (t, 2H, J = 6.2), 2.37 (t, 2H, J = 6.2). $^{13}$C NMR (100 MHz, CDCl$_3$): δ 185.81, 177.55, 170.22, 161.98 (d, J = 47.5), 159.48 (d, J = 47.5), 133.07 (d, J = 9.3), 131.71 (d, J = 9.3), 131.49 (d, J = 13.2), 131.36 (d, J = 15.5), 130.71, 124.42 (d, J = 3.1), 124.23 (d, J = 3.1), 122.44 (d, J = 13.3), 122.11 (d, J = 13.9), 116.26 (d, J = 22.5), 115.94 (d, J = 21.8), 46.23 (d, J = 4.6), 43.59 (d, J = 4.4), 29.01, 27.42. | ESI Mass calculated for $C_{23}H_{19}F_2NNaO_4$ $(M + Na)^+$ 434.11, found 434.07 |
| 4.3.2. 4-Oxo-4-[3,5-bis(2-fluoro-benzylidene-4-piperidone-1-yl)-2-butenoic acid] (13): Maleic anhydride (66 mg, 0.67 mmol) was reacted with 1, (200 mg, 0.64 mmol) in triethylamine (0.24 ml, 1.77 mmol) to obtain 13 as yellow foamy solid in 84% yield (220 mg). $R_f = 0.27$ | $^1$H NMR (400 MHz, CDCl$_3$): δ 7.91, 7.80 (2s, 2H, C=CH), 7.42-7.05 (m, 8H, Ar—H), 6.13 (br, 1H, J = 11.1), 4.83, 4.60 (2s, 4H). $^{13}$C NMR (100 MHz, DMSO-d6): δ 185.51, 168.23, 166.62, 161.96 (d, J = 52.2), 158.78 (d, J = 51.9), 132.74 (d, J = 46.7), 131.59 (d, J = 44.3), 131.12 (d, J = 44.9), 130.50 (d, J = 36.6), 124.43 (d, J = 3.9), 124.35 (d, J = 3.9), 123.59 (d, J = 3.9), 122.47 (d, J = 11.6), 122.41 (d, J = 13.2), 122.10 (d, J = 14.0), 116.18 (d, J = 17.1), 115.97 (d, J = 17.1), 115.30 (d, J = 11.6), 47.31, 43.11 | ESI Mass calculated for $C_{23}H_{17}F_2NNaO_4$ 432.10 $(M + Na)^+$, found 432.00 |
| 4.3.3. 5-Oxo-5-[3,5-bis(2-fluoro-benzylidene-4-piperidone-1-yl)-3-oxy-pentanoic acid] (14): Diglycolic anhydride (78 mg, 0.67 mmol) was reacted with 1, (200 mg, 0.64 mmol) in triethylamine (0.24 ml, 1.77 mmol) to obtain 14 as yellow foamy solid in 52% yield (142 mg). $R_f = 0.14$ | $^1$H NMR (400 MHz, CDCl$_3$): δ 7.86 (s, 2H, C=CH), 7.40-7.10 (m, 8H, Ar—H), 4.70, 4.56 (2s, 4H), 4.00 (s, 2H), 3.73 (s, 2H). $^{13}$C NMR (100 MHz, CDCl$_3$): δ 185.55, 173.45, 168.34, 162.39 (d, J = 25.3), 159.98 (d, J = 25.5), 132.82, 131.58 (d, J = 14.7), 131.32 (d, J = 14.7), 130.79, 124.32 (d, J = 11.9), 122.18 (d, J = 11.9), 116.23 (d, J = 14.9), 116.11 (d, J = 14.8), 69.55, 69.18, 43.48 | ESI Mass calculated for $C_{23}H_{19}F_2NNaO_5$ $(M + Na)^+$ 450.11, found 450.13 |
| 4.3.4. 5-Oxo-5-[3,5-bis(2-fluoro-benzylidene-4-piperidone-1-yl) | $^1$H NMR (400 MHz, CDCl$_3$): δ 12.00 (br s, 1H, COOH), 7.72, 7.57 (2s, 2H, C=CH), 7.55-7.50 (m, 4H, Ar—H), 7.40-7.30 (m, 4H, | ESI Mass calculated for |

TABLE 3-continued

Synthesis details for series C compounds

| Particulars | NMR | Mass |
|---|---|---|
| pentanoic acid] (15): Glutaric anhydride (114 mg, 1.01 mmol) was reacted with 1, (300 mg, 0.96 mmol) in triethylamine (0.26 ml, 1.92 mmol) to obtain 15 as yellow crystalline solid in 96% yield (393 mg). $R_f = 0.33$ | Ar—H), 4.72. 4.70 (2s, 4H), 2.16 (t, 2H, J = 7.2), 2.03 (t, 2H, J = 7.3), 1.52 (t, 2H, J = 7.3). $^{13}$C NMR (100 MHz, CDCl$_3$): δ 184.96, 173.96, 170.44, 162.40 (d, J = 45.6), 159.7 (d, J = 45.8), 132.70, 131.19 (d, J = 14.1), 131.46 (d, J = 14.0), 129.68 (d, J = 28.8), 124.19 (d, J = 13.5), 122.14 (d, J = 13.2), 121.25 (d, J = 13.3), 115.53 (d, J = 22.6), 21.9 (d, J = 23.3), 114.40 (d, J = 21.7), 46.05, 42.45, 32.53, 31.14, 19.48 | $C_{24}H_{21}F_2NNaO_4$ $(M + Na)^+$ 448.13, found 448.13 |
| 4.3.5. 2-[3,5-Bis(2-fluorobenzylidene-4-piperidone-1-yl)carbonyl] benzoic acid (16): Phthalic anhydride (100 mg, 0.67 mmol) was reacted with 1, (200 mg, 0.64 mmol) in triethylamine (0.24 ml, 1.77 mmol) to obtain 16 as yellow amorphous solid in 93% yield (247 mg). $R_f = 0.34$ | $^1$H NMR (400 MHz, DMSO-d6): δ 13.11 (br s, 1H, COOH), 7.80 (s, 2H, C=CH), 7.62 (t, 2H, Ar—H, J = 7.6), 7.53 (s, 2H, Ar—H), 7.36 (t, 2H, Ar—H, J = 6.9), 7.23 (t, 2H, Ar—H, J = 7.6), 7.17-7.09 (m, 2H, Ar—H), 7.03-6.92 (m, 2H, Ar—H), 4.84, 4.26 (br, 4H). $^{13}$C NMR (100 MHz, DMSO-d6): δ 185.49, 169.29, 166.77, 161.85 (d, J = 69.9), 159.37 (d, J = 69.3), 137.54, 134.30 (d, J = 19.4), 132.62, 132.37 (d, J = 8.5), 131.81 (d, J = 8.5), 131.39, 130.76, 130.21, 129.05, 128.45, 128.24, 126.62, 125.18 (d, J = 3.8), 124.49 (d, J = 3.9), 122.59 (d, J = 13.2), 121.98 (d, J = 13.2), 116.34 (d, J = 21.8), 115.93 (d, J = 21.0), 47.19, 42.93 | ESI Mass calculated for $C_{27}H_{19}F_2NNaO_4$ $(M + Na)^+$ 482.11, found 482.07 |
| 4.3.6. 2-[3,5-Bis(2-fluorobenzylidene-4-piperidone-1yl)carbonyl] cyclohexane carboxylic acid (17): 1,2-Cyclohexane carboxylic anhydride (104 mg, 0.67 mmol) was reacted with 1, (200 mg, 0.64 mmol) in triethylamine (0.24 ml, 1.77 mmol) to obtain 17 as yellow foamy solid in 88% yield (263 mg). $R_f = 0.48$ | $^1$H NMR (400 MHz, CDCl$_3$): δ 7.94, 7.89 (2s, 2H, C=CH), 7.44-7.30 (m, 4H, Ar—H), 7.29-7.10 (m, 4H, Ar—H), 5.07 (d, 1H, J = 16.4), 4.70-4.40 (m, 4H), 2.78 (t, 1H, J = 3.4), 2.48 (t, 1H, J = 3.4), 2.20-2.10 (m, 1H), 1.70-1.40 (m, 3H), 1.38-1.10 (m, 2H), 1.00-0.08 (m, 1H). $^{13}$C NMR (100 MHz, CDCl$_3$): δ 185.49, 177.02, 173.96, 133.49, 132.8 131.62 (d, J = 29.8), 130.98 (d, J = 29.6), 124.35 (d, J = 14.3), 123.60 (d, J = 14.1), 116.27 (d, J = 14.7), 115.18 (d, J = 14.7), 46.70, 44.06, 42.39, 26.65, 26.24, 23.68, 23.25, 21.92 | ESI Mass calculated for $C_{27}H_{25}F_2NNaO_4$ $(M + Na)^+$ 488.16, found 488.13 |

Figure 3:
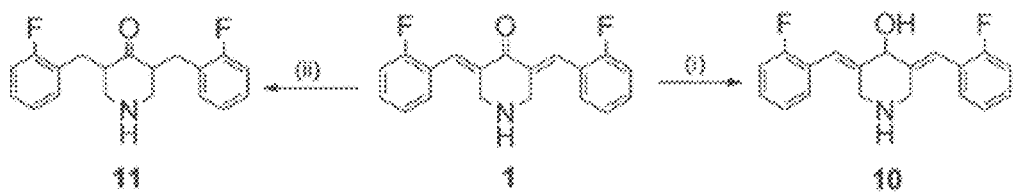
FIG. 3 illustrates the selective reduction of -ene and -carbonyl functionalities in 3,5-bis(2-fluorobenzylidene)-4-piperidone.

Series B compounds (reduction of unsaturated vinyl bonds and ketone group): The conjugated enone (in 1) was modified by selectively reducing either the double bonds, or the ketone group. First, the ketone functional group of 3,5-bis(2-fluorobenzylidene)-4-piperidone was exclusively reduced to the corresponding alcohol using NaBH$_4$ (FIG. 3). Sodium borohydride is a selective reductant for reducing ketone functional group to hydroxyl derivative without affecting the -ene part of enone. [Modzelewska et al., 2006; E1-Subbagh et al. 2000; Rahman et al., 1985] It was observed that the ketone reduction resulted in disappearance of the characteristic yellow color in the precursor compound. The structure of 3,5-bis(2-fluorobenzylidene)-4-hydroxy-piperidine (10) was confirmed by the appearance of a C-4 proton, obtained by reduction of carbonyl group, at δ 4.66 ppm CH NMR).

The selective reduction of olefin functional group of 3,5-bis(2-fluorobenzylidene)-4-piperidone was accomplished by Pd/C/H$_2$ at atmospheric pressure to obtain 3,5-bis(2-fluorobenzyl)-4-piperidone, 11 (FIG. 3).

Figure 4:
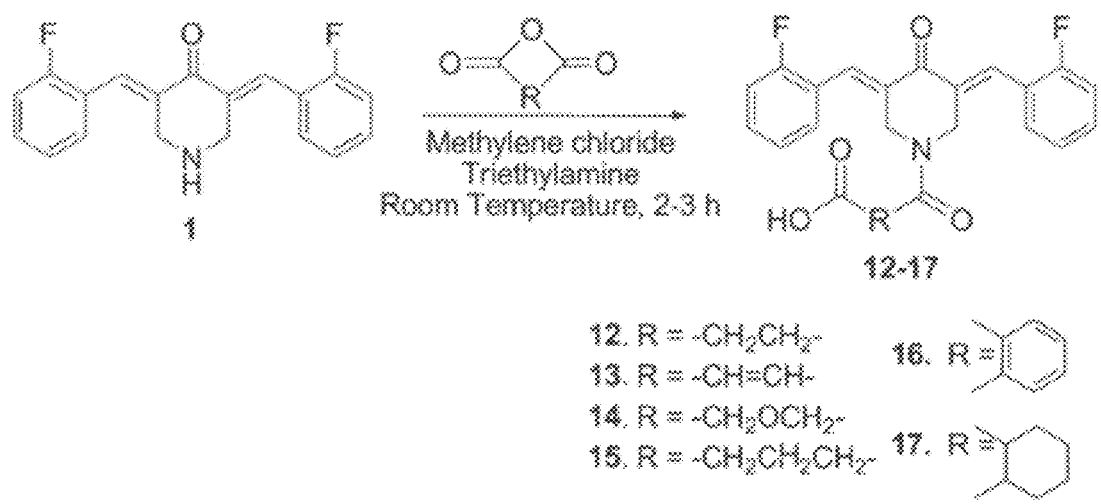
FIG. 4 illustrates a general scheme for the synthesis of N-acyl derivatives of 3,5-bis(2-fluorobenzylidene)-4-piperidone. See Table 2 for details of the numbered compounds 12 to 17.

Series C compounds (N-acyl monocarboxylic acid derivatives): One of the goals was to impart additional reactive sites to the purported 1,5-diary)-3-oxo-1,4-pentadienyl pharmacophore of 1. The additional reactive site could facilitate addition of a linker for targeting, or improving physicochemical properties by enabling conjugation to molecules, such as poly(ethylene glycol). Piperidinyl nitrogen was modified by using anhydrides of various dicarboxylic acids to form N-acyl monocarboxylic acid derivatives. The reaction of 3,5-bis(2-fluorobenzylidene)-4-piperidone (1) with dicarboxylic acid anhydrides in presence of triethylamine in methylene chloride provided the corresponding acid derivatives 12-17 in high yields within 2-3 h at room temperature (FIG. 4). The anhydrides were chosen based on the varying carbon chain-length, aromaticity and unsaturation. For instance, compound 13 (maleic) represents an unsaturated counterpart of compound 12 (succinic). [Sun et al., 2006] Similarly, 14 (diglycolic) is a congener of compound 15 (glutaric). For exploring the effects of saturated vs unsaturated rings of N-acyl monocarboxylic acid derivatives, compounds 16 and 17 were synthesized.

The piperidine methylene (C-2) protons of acid derivatives (12-17) of compound 1 appeared at δ 4.26-4.70 and δ 4.70-4.84 ppm as two singlets. On the other hand, in the precursor compound 1, these protons were at δ 4.40 ppm as one singlet. This difference observed is more likely due to the tertiary amide rotamers in compounds 12-17.

Figure 5:
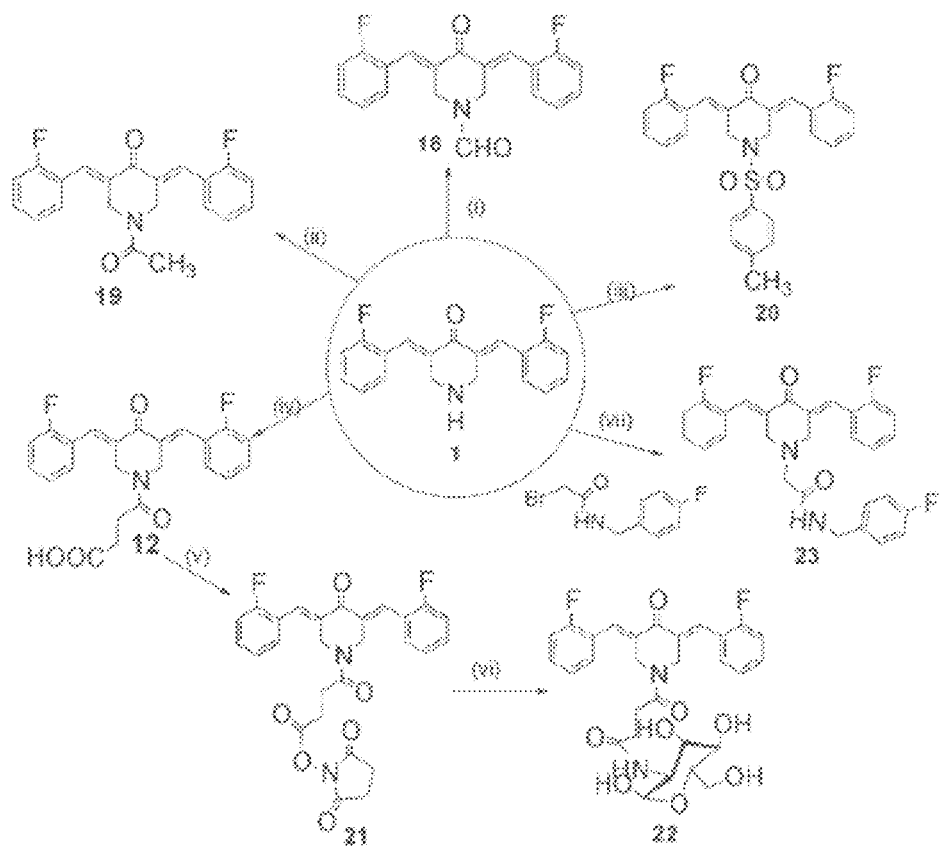
FIG. 5 depicts a synthetic schemes for various N-substituted derivatives of 3,5-bis(2-fluorobenzylidene)-4-piperidone. See Table 3 for details of the numbered compounds 18 to 23.

Series D (N-substitutions on compound 1): The secondary nitrogen of piperidone ring in 1 could be modified to alter the anti-proliferative properties. As such, formylation, acetylation, tosylation and glycation were performed at this nitrogen. Formylation of 1 by a 2:1 mixture of formic acid:acetic anhydride [Reddy et al., et al., 2000; Westerhoff et al., 2001] afforded us an aldehyde derivative, N-formyl-3,5-bis(2-fluorobenzylidene)-4-piperidone (18). The same compound was also obtained by the formylation of compound 1 with ammonium formate, and refluxing in acetonitrile for 16 h (FIG. 5).

N-acetyl derivative of compound 1 was obtained by reacting compound 1 with acetic anhydride in pyridine. Similarly, an N-tosyl derivative, 20, was synthesized by a reaction with tosyl chloride in pyridine.

An addition of glucose moiety at the piperidinyl nitrogen was performed with a goal to achieve higher aqueous solubility, and a possibility of enhanced trans-cellular transport via glucose transporters. This chemical modification was accomplished in a two-step process. First, a reactive succinimidyl ester intermediate of compound 1 was synthesized. Briefly, 12 (succinic acid derivative of 1) was activated to an N-hydroxy succinimide ester derivative (21) by reaction with N-hydroxy succinimide in dichloromethane in presence of dicyclohexyl carbodiimide (DCC). The N-hydroxy esters are known to be reactive towards primary amine group. To add glucose moiety, 2-glucosamine was allowed to react with 21 in pyridine solvent at 90° C. After 3 h, compound 22 was obtained in good yield.

Figure 6:
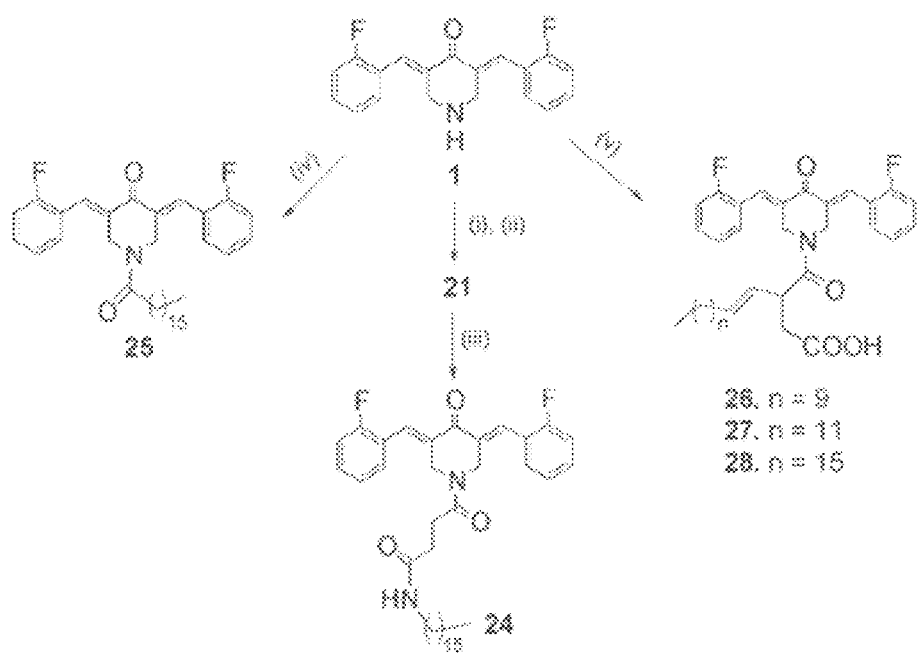
FIG. 6 depicts a synthetic scheme for the lipid derivatives of 3,5-bis(2-fluorobenzylidene)-4-piperidone.

Series E (lipid derivatives of compound 1): The inventors have an additional interest in the incorporation of cytotoxic drugs in lipid drug carriers, such as liposomes. In order to stably incorporate the cytotoxic analogs in such formulations, five lipid derivatives of compound 1 were synthesized. The reaction schemes for these modifications are described in FIG. 6. The hexadecylamine conjugate, 24 was a product of a reaction between 21 and hexadecylamine. To obtain N-stearoyl derivative (25), stearoyl chloride in dichloroethane was allowed to react with compound 1. After 16 h and usual work up, N-stearoyl-3,5-bis(2-fluorobenzylidene)-4-piperidone, 25 was obtained in 67% yield. The other lipid derivatives, 26-28 were obtained by treating 1 with long chain dicarboxylic acid anhydrides, such as dodecenyl succinic anhydride, tetradecenyl succinic anhydride and octadecenyl succinic anhydride. The reactions were accomplished within 2 h, and lipidoyl monocarboxylic acid derivatives were obtained in good yields.

Biology

Cell Proliferation Studies: In order to assess the anti-proliferative activity of the synthesized compounds, an in vitro cell culture system of lung adenocarcinoma cell line H441 was used. The cell detachment and anti-proliferative activity was measured as a decrease in hexosaminidase enzyme activity associated with remainder of the adhered cells. [Landegren, 1984] The concentration of various compounds to inhibit 50% of H441 cell proliferation ($IC_{50}$) was evaluated after 24 h of treatment (1-100 µM). The concentration versus cell proliferation plots were analyzed by an exponential fit (Table 1). The results were compared with the anti-proliferative activity of compound 1. As shown in Table 1, only five of the synthesized compounds 2, 3, 4, 13 and 29 showed anti-proliferative potency exceeding that of compound 1 ($IC_{50}$<30 µM). Compounds 5, 8, 9, 10, 11, 12, 14, 15, 16, 17, 19, 20, 22, 24, 26 and 28 showed significantly lower activity ($IC_{50}$>50 µM), and the rest of the compounds demonstrated more or less no change in activity as compared to that shown by compound 1 (30 µM<$IC_{50}$<50 µM).

Figure 7A:
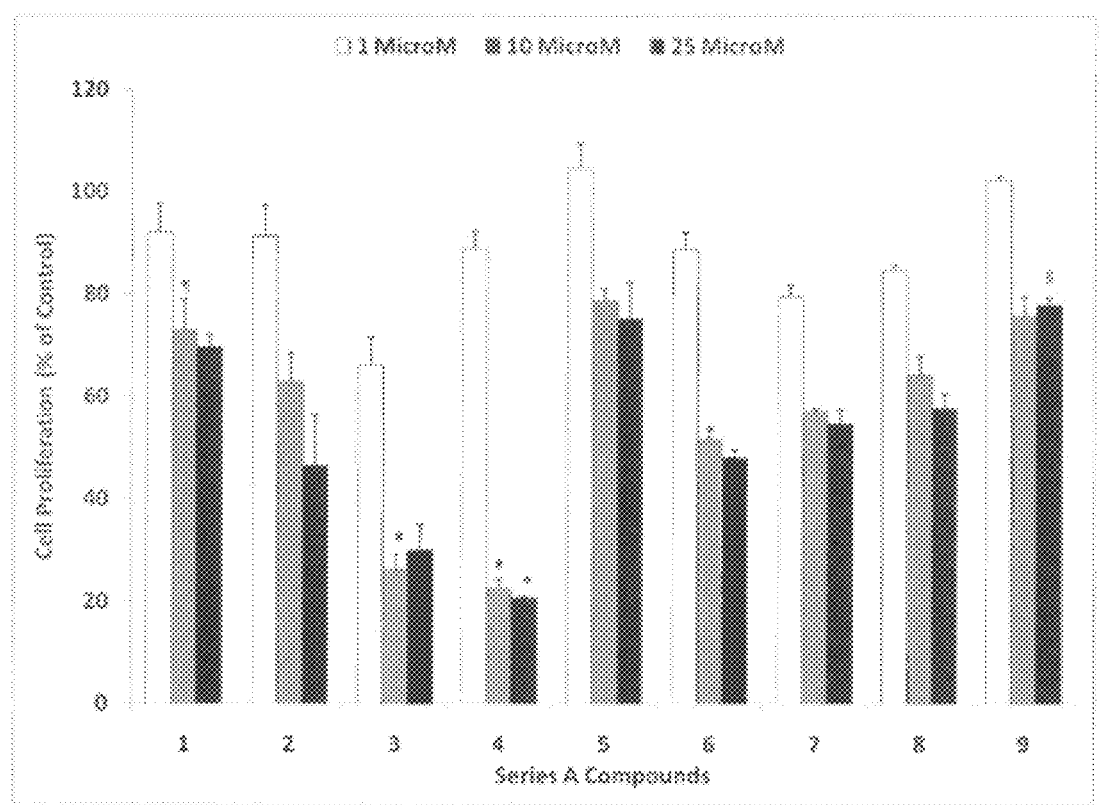
FIG. 7 illustrates the results of a study of anti-proliferative action of various compounds by hexosaminidase assay in lung adenocarcinoma H441 cells. Compound belonging to Series A (a), Series B (b), Series C (c), Series D (d), and Series E (e) were tested. Symbols ¶, *, # and $ indicate p<0.001 compared to control, p<0.05 compared to compound 1, p<0.01 compared to compound 1, and p<0.001 compared to compound 1, respectively.

It has been shown that electron-withdrawing substitutions in the aromatic rings enhances the cytotoxicity of 3,5-bis(benzylidene)-4-piperidones. [Pati et al., 2008; Dimmock et al., 1990; Pati et al., 2009] For instance, chalcones with electron withdrawing groups in the 2- and 6-positions of aromatic rings have been reported to be potent inhibitors for endothelial cell proliferation. [Robinson et al., 2005] Similarly, the compounds with fluorine atoms at ortho-position have been reported to be potent anti-cancer compounds in breast, ovarian and colon cancers. [Subramaniam et al., 2008; Lagisetty et al., 2009; Leyon et al., 2003; Anand et al., 2007; Adams et al., 2004; Selvendiran et al., 2007; Thomas, et al., 2008] Contrary to these observations, it was found that 2-chloro substituted compound 3 is more anti-proliferative than the 2-fluoro substituted compound 1 (FIG. 7a). When a strong electron withdrawing nitro substitution was performed at 2-position of the aromatic rings, 5, the activity remained more or less the same. On the other hand, 3-chloro-substitution (6) showed little change in $IC_{50}$ as compared to that of compound 1. There is only one report about the 2-substituted compound in the published literature. [Snyder et al., 2003]

There are a few accounts of 3,5-bis(benzylidene)-4-piperidones where the aromatic ring carries a substitution at para-position. It has been recently shown that 2-, 3- and 4-fluoro substitutions have good inhibitory effects against the Fanconi anemia pathway responsible for DNA repair in cancer cells. [Landais et al., 2009] Electron-withdrawing substitutions at para-position have been reported to diminish anti-cancer activity of compounds as compared to those that carry no substitution at para-position. [Pati et al., 2008; Dimmock et al., 1990; Pati et al., 2009] However, another report found that 3,5-bis(4-chlorobenzylidene)-N-methyl-4-piperidone possessed most active anti-HIV activity; the activity decreased with para-substitutions with $CH_3$ and $OCH_3$, or without any substitution. [El-Subbagh et al., 2000] In yet another report, 4-hydroxy and 3,4 dihydroxy derivatives of 3,5-bis(benzylidene)-4-piperidones were found to be inhibitors of α-glucosidase and HIV integrase enzymes. [Du et al., 2006; Artico et al., 1998] In the inventors' experience, 4-chloro substitution resulted in no change in the anti-proliferative activity of 8 compared to that of 7 possessing a 4-fluoro substitution. Taken together the results imply that para-substitution with strong electron-withdrawing groups may increase the anti-proliferative activity.

Figure 7B:
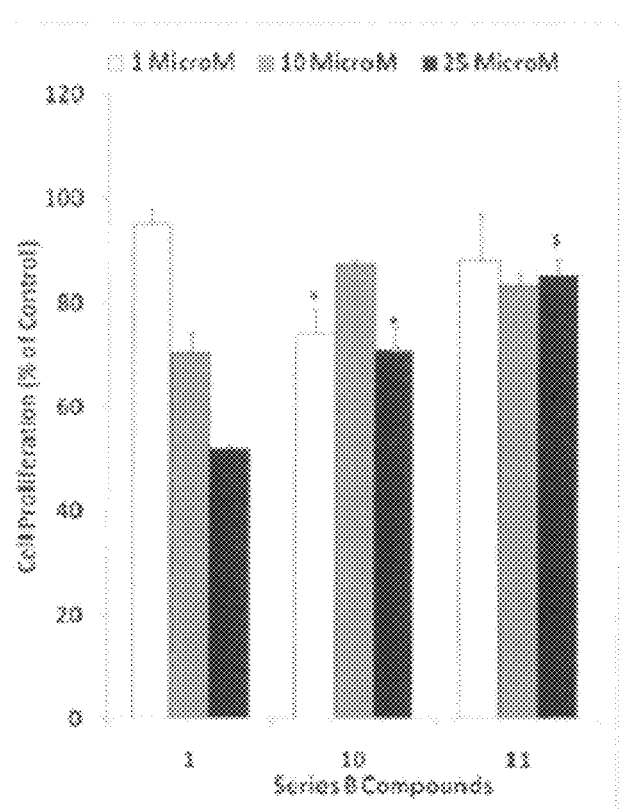

In compounds 10 and 11 (series B), the enone unsaturation is selectively reduced. Both these compounds showed significantly less anti-proliferative activity as compared to compound 1 (FIG. 7b). Apparently, the unsaturation is important for potent activity of compound 1. These results are consistent with previous reports where it has been shown that this structural feature mediates interaction with thiols inside the cell. [Modzelewska et al., 2006; Pati et al., 2008; El-Subbagh et al., 2000; Pati et al., 2009]

Figure 7C:
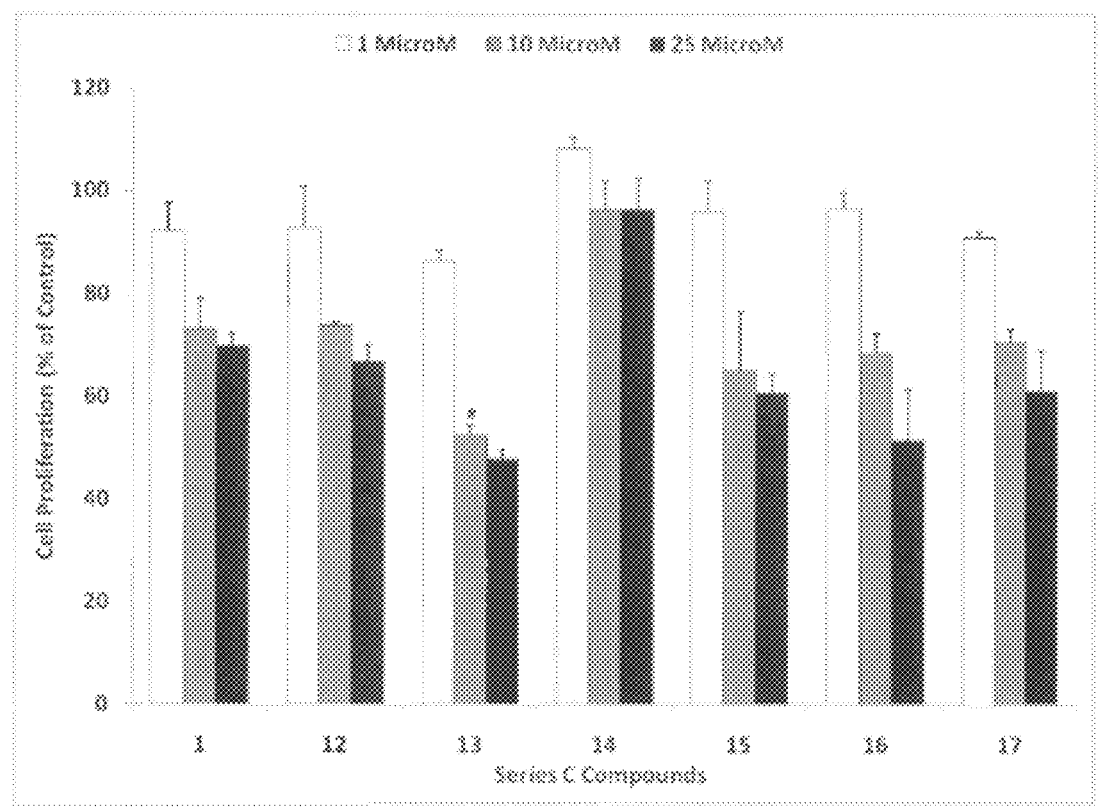

The structural modifications of 3,5-bis(benzylidene)-4-piperidones were extended to the substitutions on piperidinyl nitrogen. In general, N-substituted derivatives have been reported to be less cytotoxic than their precursors. Only, N-acroyl analogs have been shown to be more potent than their precursors. [Das et al., 2007; Das et al., 2008; Das, et al., 2008] It has been suggested that this may be due to the double bond in acroyl moiety which provides an additional site of interaction with intracellular constituents, such as glutathione. [Pati et al., 2008; Das et al., 2007; Das, et al., 2008; Das et al., 2008] N-substituted carboxylic acid derivatives (Series C) were synthesized. All the members of this series were anti-proliferative, and compared to compound 1, the differences in activity at 25 µM dose were not significant. Compound 14 is an oxy-linked congener of compound 15, but is found to be less potent as compared to compound 15. Compound 13 (maleic acid derivative) showed a significant enhancement in potency. Compound 16 was found to be a very potent analog possessing anti-proliferative activity at lower doses similar to that shown by the higher doses of compound 1 (FIG. 7c). These results suggest that by appropriately choosing a carboxylic acid chain, compound 1 can be modified at piperidinyl nitrogen to carry additional functional features, such as an imaging radionuclide, or a cancer-specific ligand for targeted cytotoxicity.

Figure 7D:
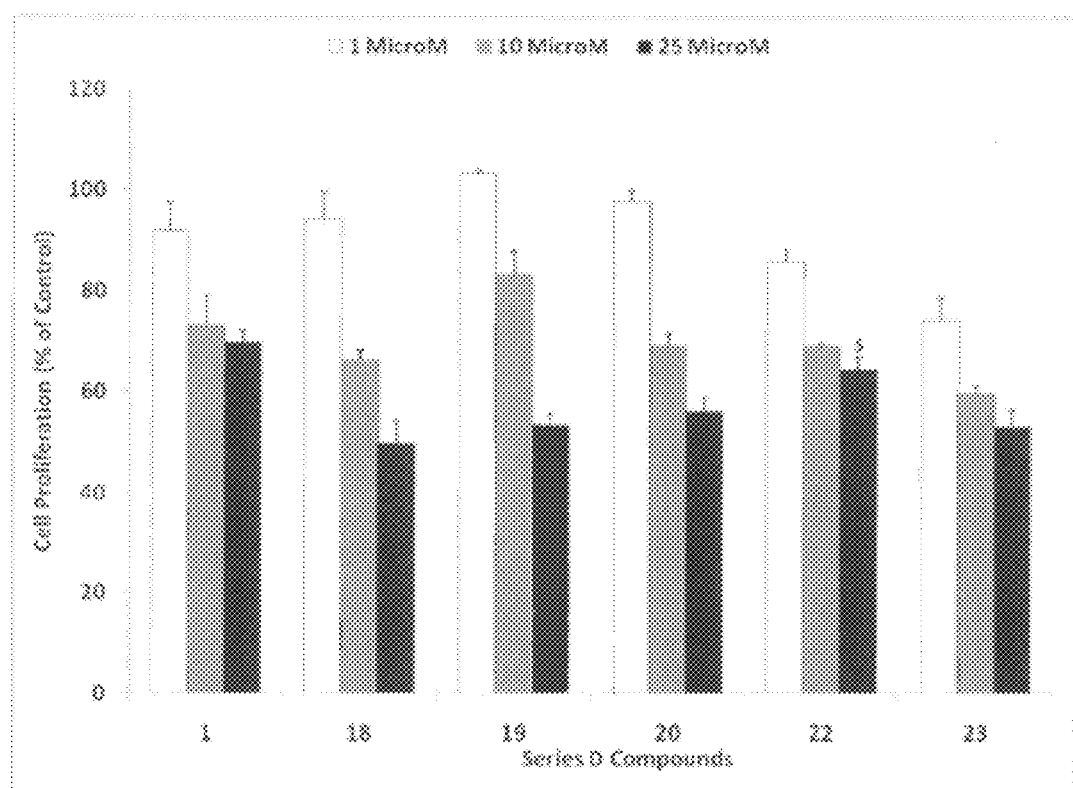
Figure 7E:
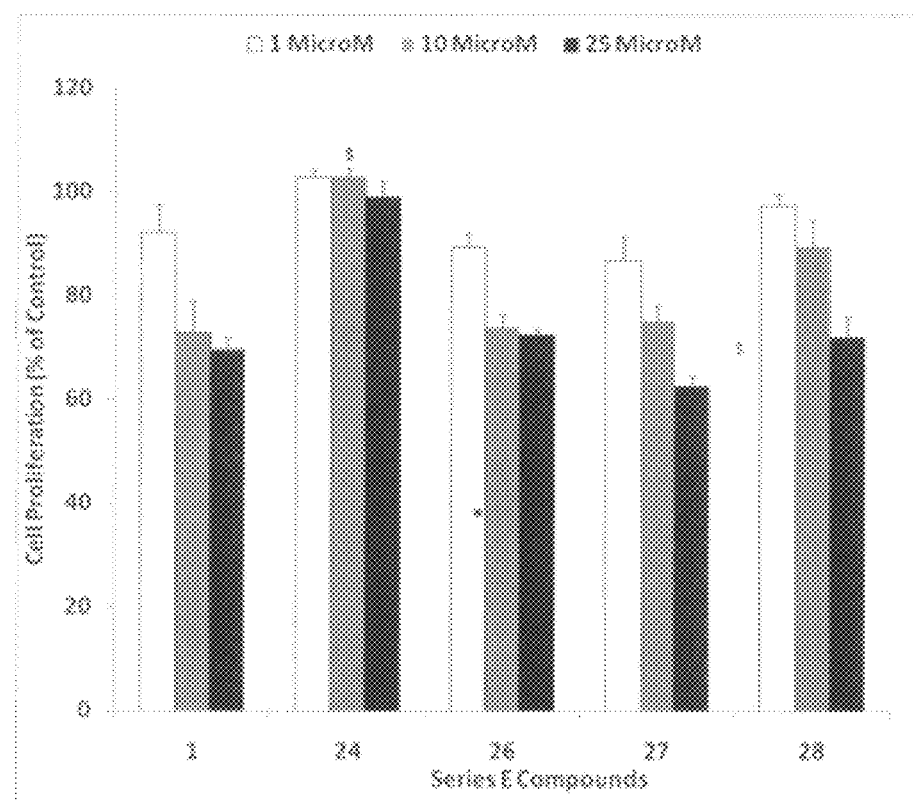

In series D, piperidinyl nitrogen was substituted with more short chain moieties. All compounds, except compound 22, showed anti-proliferative activity comparable to that shown by compound 1. In fact, compounds 18 and 19 performed slightly better than compound 1 (FIG. 7d). This observation re-affirmed the previous observation with carboxylic acid derivatives that short chain substitutions at piperidinyl nitrogen do not compromise anti-proliferative activity of 3,5-bis(benzylidene)-4-piperidones. Compound 22 is a glucosylated analog that was synthesized to impart selectivity to the anti-proliferative action in cells over-expressing GLUT transporters. It remains to be seen if in spite of reduced anti-proliferative activity, this compound shows any selectivity in cell killing. Compound 23 contains a third fluorine atom in the substitution at piperidinyl nitrogen. This compound was prepared to obtain a radioactive positron-emitting F-18-labeled analog of compound 23 for imaging with positron emission tomography.

Since short chain N-substitutions demonstrated minimal impact on the activity of compound 1, it was desired to link longer lipid chains at piperidinyl nitrogen (Series E). The goal was to synthesize compounds that can be inserted into lipid carriers, such as liposomes. It was clear that compounds 26 and 27 containing dodecenyl- and tetradecenyl-modifications had an acceptable anti-proliferative activity, but the substitution with 18-carbon octadecenyl lipid (compound 28) resulted in a total loss of activity. All these compounds were soluble in dimethyl sulfoxide, but another N-stearoyl analog (not shown) was insoluble in all common solvents except chloroform, and was not tested for activity in cell culture. The retention of activity by compounds with 12-14 carbon unsaturated a chain modification is encouraging, for it enables the incorporation of these compounds in a lipid carrier system. It is interesting to note that N-substitution with a saturated hexadecyl amine chain (compound 24) also resulted in a loss of anti-proliferative activity. This appears to be the first report where piperidinyl nitrogen of chalcones has been modified with lipid chains.

From the results described above, a few structural requirements for anti-proliferative action of 3,5-bis(benzylidene)-4-piperidones were determined. A few important characteristics of the synthesized compounds are included in Table 2. It is clear from the results of cell proliferation experiments in lung adenocarcinoma cells that the structural requirements for retaining (or enhancing) anti-proliferative properties in 3,5-bis(benzylidene)-4-piperidones are not rigid. As such, the observations supported the following general conclusions:

1. An ortho-substitution on the aromatic rings with less electronegative halogens compared to fluorine, such as chloro—may increase the activity.
2. The meta-position substitutions have minimal impact on anti-proliferative activity.
3. A para-substitution with electron-donating group, such as $(CH_3)_2NH$-group reduces the activity.
4. The enone moiety is critical for the growth inhibitory activity.
5. The unsaturated short-chain carboxylic substitutions at piperidinyl nitrogen may result in more active compounds.
6. The short lipid modifications at piperidinyl nitrogen do not adversely affect anti-proliferative activity.

Figure 8:
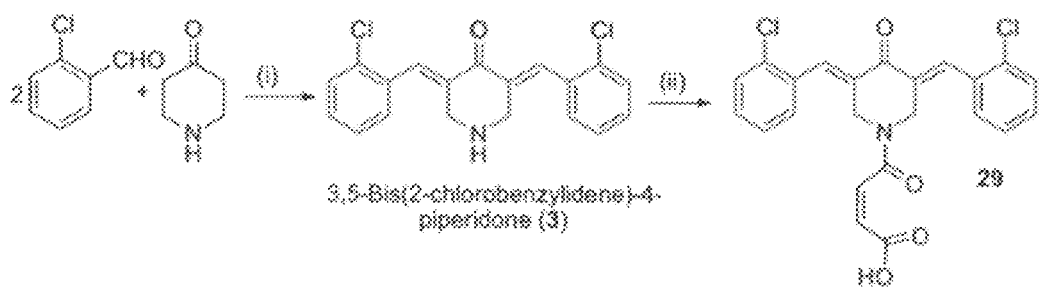
FIG. 8 illustrates a synthesis scheme for the predicated compound 29 or CLEFMA.
Figure 9:
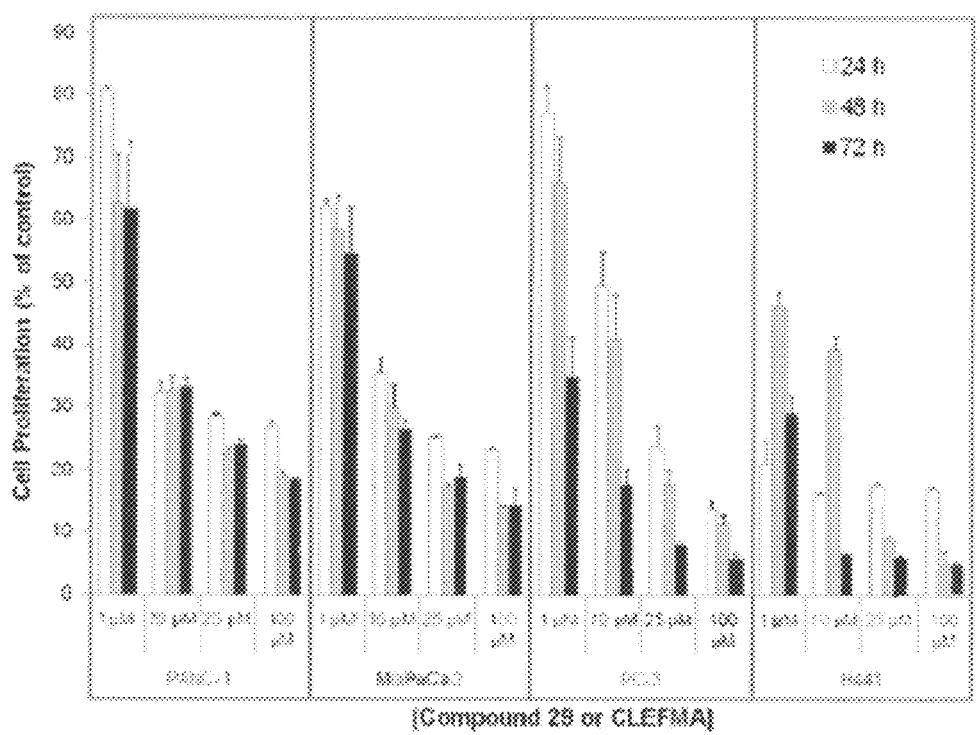
FIG. 9 depicts cell proliferation studies of CLEFMA in pancreatic cancer PANC-1 and MiaPaCa-2 cells, prostate cancer PC-3 cells, and lung adenocarcinoma H441 cells.

Based on this premise, a compound (29, or CLEFMA) carrying N-maleic acid functional group, and 2-chloro substitution on the aromatic rings was synthesized (FIG. 8). From the cell proliferation studies in cancer cell lines, H441 (lung adenocarcinoma), PC-3 (prostate cancer), MiaPaCa-2 and PANC-1 (both pancreatic cancer), it was clear that the predicted structural modifications enhanced the potency of anti-proliferative action (FIG. 9). The light microscopic observations clearly demonstrated the impact of drug treatments on cell number and morphology (not shown). Although the exact mechanism is unclear, the introduction of an additional $\alpha,\beta$-unsaturated carbonyl unit could have aided in the enhanced anti-proliferative activity of CLEFMA.

Figure 10:
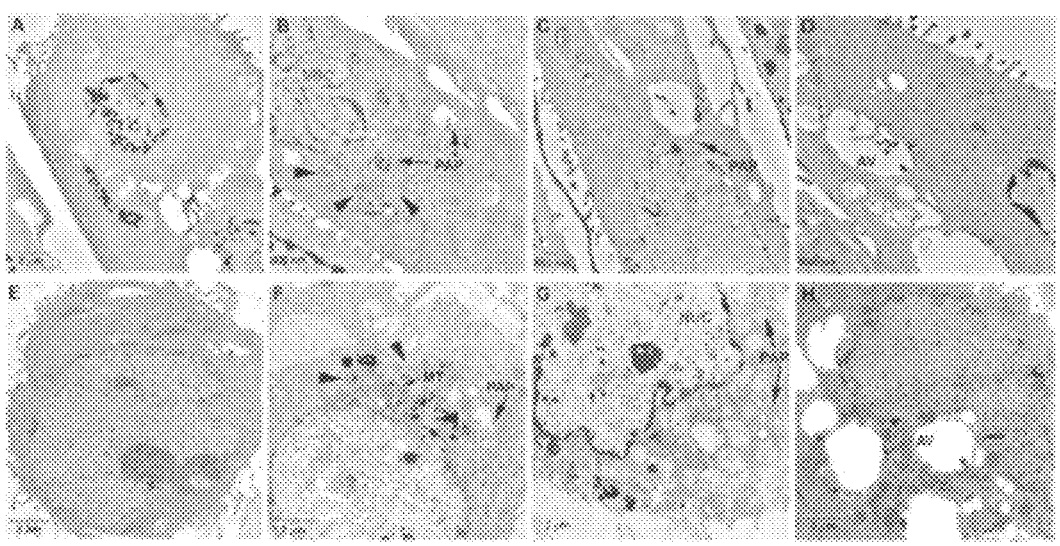
FIG. 10 contains transmission electron micrographs of H441 cells treated with compound 1 (B to D) and compound 29 or CLEFMA (F to G). For comparison, the untreated cells were also micrographed as controls (A and E). The typical features of autophagy were observed. The cells showed nuclear (Nuc) blebbing, and perinuclear accumulation of organelles (arrow head) as well as mitochondria (MT). There were numerous pre-autophagosomes or PAPs, and autophagosomes or AVs. The PAPs and AVs containing cell organelles and cytoplasmic material were widely seen.

CLEFMA (29) induce autophagic death in H441 cells: From the above qualitative cell-cycle analysis of Sub-G1 cell population, it appeared that these compounds do not induce apoptosis in H441 cells. This was also confirmed by immunoblotting of H441 cell lysates for caspase-3 activation where no change in its activation level was observed after CLEFMA treatment. Further, it was also definitively established that CLEFMA does not induce apoptosis by performing Apo-One homogeneous caspase-3/7 assay (Promega, Madison Wis.). Again, no cleavage-based caspase activation was seen (data not shown). Incidentally, the literature provides several reports that the majority of lung cancer cells, including H441 cells are resistant to apoptosis because of mutations in tumor suppressor p53 and pro-oncogenic k-Ras. [Herbst et al., 2008; Huncharet et al., 1999; Heylan et al., 2009] Next, it was investigated if these compounds cause cell death in H441 cells by inducing autophagy. In transmission electron micrographs (FIG. 10), compound 1 and CLEFMA induced a substantial change in cellular architecture. In few views, double-membrane pre-autophagosomal structures (PAP) containing cell organelles existed; large single-walled autophagic vacuoles were widely seen. There was peri-nuclear concentration of cell organelles, including mitochondria. Blebbing of nuclear membrane was evident in few cells, but no chromatin condensation (a sign that apoptosis was not induced) was observed.

Figure 11:
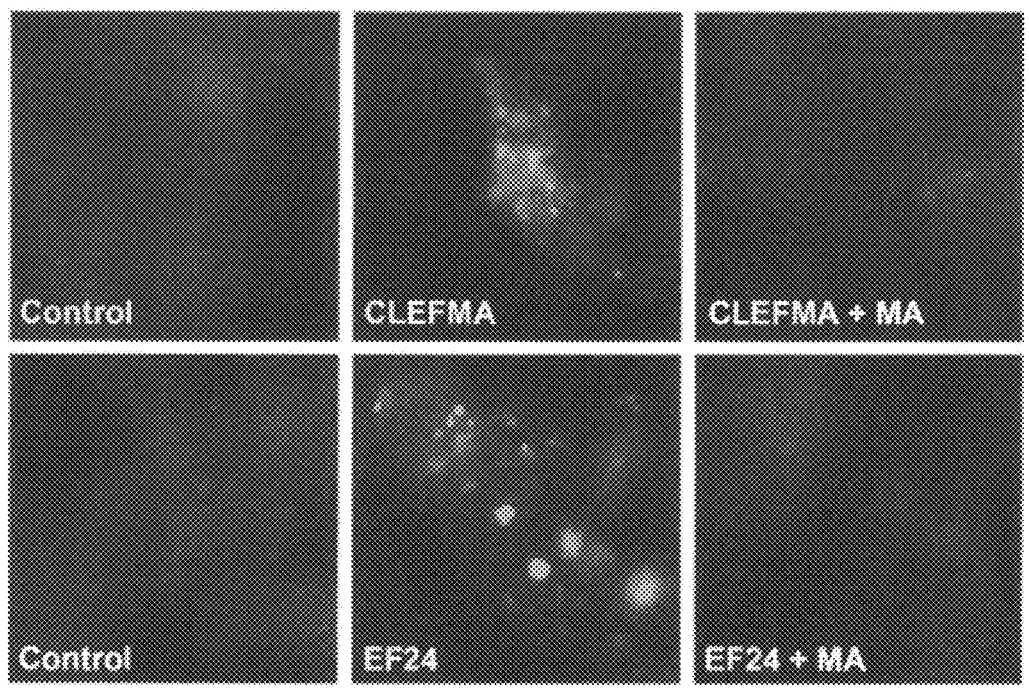
FIG. 11 contains fluorescent microscopic pictures of compound 29 (CLEFMA)- and compound 1(EF24)-induced autophagosome formation in H441 cells. The cells were labeled with an autophagosome marker monodansylcadaverine. The autophagy was inhibited by 3-methyladenine (3-MA).

In a separate fluorescence microscopy-based experiment, it was found that the treatments with compound 1 and CLEFMA were followed by the appearance of intracellular vacuoles or autophagosomes (FIG. 11). Monodansylcadaverine (MDC) is an autofluorescent marker for autophagic vacuoles. [Biederbick et al., 1995] It was found the emergence of intense MDC-fluorescence in the treated cells. The fluorescence vanished when the cells were treated with 3-methyl adenine (3-MA). It has been shown that 3-MA specifically inhibits autophagic/lysosomal pathway by suppressing the formation of autophagosomes. [Seglen et al., 1982]

The original inventors of compound 1 (EF24) have shown that it causes apoptosis in MDA-MB-231 human breast cancer cells and DU-145 human prostate cancer cells via a redox-dependent mechanism. [Adams et al., 2006] EF24 and its analogs containing dienone moiety serve as Michael acceptors; the involvement of cellular redox status in EF24's action was confirmed in a study comparing EF24 with its water-soluble glutathione adducts. [Sun et al., 2009] That EF24 causes apoptotic cell death was also observed in cisplatin-resistant ovarian cancer cells. [Selvendiran et al., 2007] Evidently, this activity in ovarian cancer cells was mediated by induction of PTEN and inhibition of AKT activities. In a more elaborate in vivo study, Subramaniam, et al., EF24 was found to induce caspase-mediated apoptosis in HCT-116 colon cancer xenografts. [Subramaniam et al., 2008] At the same time, marked reduction in AKT activity, as well as decreased cyclooxygenase-2, interleukin-8, and vascular endothelial growth factor mRNA and protein expression was reported. [Subramaniam et al., 2008] A common theme in these studies showing mechanistic details of EF24 action has been the induction of apoptosis following G2-M cell cycle arrest. At molecular level, EF24 has been shown to suppress NF-kB signaling pathway through direct action on IkB kinase in lung, breast, ovarian and cervical cancer cells. [Kasinski et al, 2008] Evidently, NF-kB plays a pivotal role in linking inflammation and oncogenesis, [Mantovani] and an understanding is developing that the anticancer activity of curcumin and its analogs may be mediated primarily by inhibition of NF-kB activity. [Singh et al., 2006]

Contrary to the observation that EF24 induces apoptotic cell death, data is presented herein that in H441 lung cancer cells, CLEFMA induces autophagic cells death. By flowcytometric analysis and caspase-3 immunoblotting also, the characteristic signatures of apoptotic cell death could not be found (data not shown). Although apoptosis is believed to be the primary mechanism of chemotherapy-induced cell death, there is considerable merit in designing drugs that induce a mode of cell death alternative to apoptosis, especially in cells that may be deficient in cellular mediators of apoptosis. For instance, lung cancers are resistant to therapeutic induction of apoptosis because of the mutation in apoptosis regulators p53, bcl-2 and p21WAF1 genes. [Huang et al., 2007; Lee et al., 1995; Niklinski et al., 2001] Interestingly, H441 cells have recently been reported to carry p53 as well as k-Ras mutation to gain survival advantage [Meylen et al., 2009]. Altered expression of these genes renders many of the apoptosis-inducing drugs ineffective in lung cancer. Therefore, therapies that promote other types of death, such as autophagy, may be preferential for use in treating lung cancer. At the same time, current scientific evidence is suggestive of a more heterogeneous model of tumor response to therapy wherein multiple modes of cell death combine to generate an overall tumor response. Perhaps the eventual mechanism(s) of cell death is determined by the drug, the dosing regimen, and the genetic background of the tumor cells [Morse et al., 2005]. This conjecture is supported by the observation that the therapeutic response does not correlate with apoptosis, and that anti-apoptotic mutations or altered expression of genes, such as bcl-2, p21, and p53, are not negative predictors of therapeutic benefits [Lock et al., 1996; Rein et al., 2000; Wouters et al., 1997].

EXPERIMENTAL

All reagents were obtained from commercial sources, and used directly without further purification. The reactions were monitored by thin layer chromatography (TLC) on 250 μm silica plates. $^1$H NMR spectra and $^{13}$C NMR spectra (DMSO-d6 and CDCl$_3$) were recorded at 300 and 75 MHz on Mercury-VX 300 and Varian VNMRS-400 NMR Spectrometers. Spectra were referenced to the residual protonated solvents. Abbreviations s, d, t, m, br, dd and dt used in the description of NMR spectra denote singlet, doublet, triplet, multiples, broad, double doublet, and double triplet, respectively. Chemical shifts and coupling constants were reported in δ parts per million (ppm) and Hertz (Hz), respectively. Mass spectra were recorded by Finnigon Mat LCQ mass spectrometer (San Jose, Calif.). Samples for IR spectroscopic measurements were finely ground, and prepared as KBr pellets in a Bruker IFS 66v spectrometer with a KBr beam splitter. Sixty four scans at a spectral resolution of 1 cm$^{-1}$ were averaged for each spectrum. Melting points were recorded on an Electrothermal MeI-Temp melting point apparatus (Thermo Scientific, Waltham, Mass.). The reported melting points (degree Celsius) are uncorrected. Where applicable, the compounds were purified by column chromatography using 200-300 mesh silica gel columns.

Chemistry

General method for the synthesis of series A compounds: Hydrochloric Acid gas (generated in situ) was bubbled into a solution of 4-piperidone hydrochloride monohydrate (1 eq) in glacial acetic acid until a clear solution was obtained (about 15 min). Aromatic aldehyde (2 eq) was added to the solution, and left at room temperature for 48 h. In the case of compounds 3, 4 and 5, solids were separated by scratching the glass surface for 5 min. The crystals formed were filtered on a Buchner funnel, washed with absolute ethanol (50 ml) and ether (50 ml). The hydrochloride salts of various 3,5-bis(benzylidene)-4-piperidones were obtained as yellow crystalline solids. The free bases were generated by the treating the solids with 10% K$_2$CO$_3$. Specific details of synthesis of series A compounds are described in Table 2 [Adams et al., 2004; Pati et al., 2008; Dimmock et al., 1990; Snyder et al., 2003; Das et al., 2007; Das et al., 2008; Das et al., 2009; Dimmock et al., 2001; Mosley et al., 2007; Snyder et al., 2001; Snyder et al., 2008; Snyder et al., 2008; Youssef et al., 2009].

3,5-Bis(2-fluorobenzylidene)-4-piperidone (1): From 4-piperidone hydrochloride monohydrate (3 gm, 19.5 mmol) and 2-fluorobenzaldehyde (6 ml, 56.5 mmol), compound 1 was obtained as a yellow crystalline solid (5.71 gm, 94% yield). R$_f$(60:40 ethyl acetate:hexanes)=0.46. $^1$H NMR (300 MHz, DMSO-d6): δ 9.94 (s, 1H, NH), 7.88 (s, 2H, C=CH), 7.61-7.54 (m, 2H, Ar—H), 7.51 (t, 4H, Ar—H, J=7.8), 7.39 (q, 2H, Ar—H, J=7.2), 4.37 (s, 4H). $^{13}$C NMR (75 MHz, DMSO-d6): δ 172.09, 160.37 (d, J=249.1), 132.55 (d, J=8.5), 131.79 (d, J=3.8), 131.03 (d, J=1.5), 129.89, 124.95 (d, J=3.2), 121.52 (d, J=13.1), 116.09 (d, J=21.0), 43.85 (d, J=3.1). FT-IR (cm$^{-1}$): 797, 1201, 1243, 1453, 1483, 1616, 1715, 2977, 3025. ESI mass calculated for C$_{19}$H$_{16}$F$_2$NO (M+H)$^+$312.12. found 312.13. [Adams et al., 2004; Landais et al., 2009; Snyder et al., 2001; Snyder et al., 2008; Snyder et al., 2008]

Synthesis of series B compounds: In this series, the enone unsaturation was selectively reduced in 3,5-bis(2-fluorobenzylidene)-4-piperidone.

3,5-Bis(2-fluorobenzylidene)-4-hydroxy-piperidine (10): Sodium borohydride (36 mg, 0.96 mmol) was added to a solution of compound 1 (300 mg, 0.96 mmol) in ethanol at 0° C., in portions. The reaction mixture was stirred at room temperature for 1 h. The solvent was evaporated to dryness. The residue was dissolved in chloroform, and the organic phase was washed with brine and water. The organic layer was dried over sodium sulfate, and concentrated to dryness. The crude product was passed through silica column, and eluted with 70% ethyl acetate in hexanes. The title compound 10 was obtained as colorless thick syrup (296 mg, 98% yield). R$_f$(60:40 ethyl acetate:hexanes)=0.10. $^1$H NMR (300 MHz, CDCl$_3$): δ 7.25 (s, 1H), 7.00 (q, 2H, Ar—H, J=7.4), 6.93 (t, 2H, Ar—H, J=7.8), 6.86 (t, 2H, Ar—H, J=7.0), 6.81 (t, 2H, Ar—H, J=7.6), 6.39 (s, 2H, C=CH), 4.66 (s, 1H), 3.61 (d, 2H, J=14.8), 3.25 (d, 2H, J=14.8). $^{13}$C NMR (75 MHz, CDCl$_3$): δ 161.42 (d, J=246.2), 144.36, 130.74, 128.50, 128.60, 128.49, 124.31, 124.12, 123.64, 115.43, 115.14, 75.62, 45.68. ESI Mass calculated for C$_{19}$H$_{17}$F$_2$NO (M)$^+$ 313.13. found 313.87.

3,5-Bis(2-fluorobenzyl)-4-piperidone (11): To a solution of compound 1 (300 mg, 0.96 mmol) in ethanol, 10 mg of 5% Pd/C was added. The reaction mixture was stirred for 16 h under hydrogen gas at atmospheric pressure. Pd/C was filtered, and the solvent was evaporated to dryness. Compound 11 was obtained as a white solid (285 mg, 95% yield). R$_f$ (30:70 methanol:chloroform)=0.20. $^1$H NMR (300 MHz, CDCl$_3$): δ 7.25-6.90 (m, 8H, Ar—H), 3.60-2.50 (m, 10H, NCH$_2$CHCH$_2$). $^{13}$C NMR (75 MHz, CDCl$_3$): 175.10, 161.05 (d, J=250.0), 131.34 (d, J=4.3), 128.68 (d, J=8.3), 124.28 (d, J=15.5), 115.48 (d, J=21.6), 48.55, 46.54, 25.52. ESI Mass calculated for C$_{19}$H$_{20}$F$_2$NO (M+H)$^+$316.15. found 316.20.

General Procedure for the synthesis of series C compounds: Dicarboxylic acid anhydrides (1.00-1.20 mmol) and triethylamine (2 mmol) were added to a solution of compound 1 (1 mmol) in dry methylene chloride (10 ml). The reaction mixtures were stirred at room temperature for 2-4 h. The reactions were monitored by TLC, and upon consumption of the starting material, the reaction mixtures were diluted with methylene chloride (10 mL). The diluted mixture was washed with saturated sodium bicarbonate followed by a water-wash. The organic layer was dried with anhydrous sodium sulfate and concentrated. The crude reaction products were purified by column chromatography on silica gel (200-300 mesh) using (10:90 methanol:chloroform) system solvent system, except for compound 17 where 5:95 ratio was used. Fractions containing pure product were combined, evaporated and dried under vacuum. TLC was developed in methanol:chloroform system (10:90). The synthetic details about individual compounds belonging to series C are described in Table 3 [Sun et al., 2006].

Synthesis of series D compounds: In series D four N-substituted 3,5-bis(2-fluorobenzylidene)-4-piperidones were synthesized. The substitutions were performed with functionalities containing relatively short carbon chain.

N-Formyl-3,5-bis(2-fluorobenzylidene)-4-piperidone (18): Compound 18 was synthesized by two methods. In the first method, acetic anhydride (3 ml) was added drop-wise to an ice-cold solution of compound 1 (300 mg, 0.96 mmol) in formic acid (6 ml), and the reaction mixture was stirred at room temperature for 16 h. The solvent was distilled-off under vacuum. The solid obtained was recrystallized from chloroform and hexanes to obtain 18 as a yellow solid (148 mg, 45% yield). In the second method, ammonium formate (121 mg, 1.92 mmol) was added to a solution of compound 1 (300 mg, 0.96 mmol) in dry acetonitrile. The mixture was refluxed for 24 h, before evaporating to dryness. The solid was recrystallized from methylene chloride and hexanes to obtain pure 18 as a yellow solid (190 mg, 57% yield). $R_f$ (60:40 ethyl acetate:hexanes)=0.60. $^1$H NMR (400 MHz, CDCl$_3$): δ 8.16 (s, 1H, CHO), 8.09, 8.06 (2s, 2H, C=CH), 7.60-7.22 (m, 8H, Ar—H), 4.87, 4.66 (2s, 4H). $^{13}$C NMR (100 MHz, CDCl$_3$): δ 185.34, 162.14 (d, J=45.6), 160.95, 159.87 (d, J=45.9), 132.85, 132.19 (d, J=25.7), 131.12 (d, J=25.4), 130.78, 124.46 (d, J=3.1), 116.49 (d, J=22.1), 116.18 (d, J=22.3), 46.38 (d, J=5.4), 41.11 (d, J=5.2). ESI Mass calculated for $C_{20}H_{15}F_2NNaO_2$ (M+Na)$^+$362.10. found 362.07.

N-Acetyl-3,5-bis(2-fluorobenzylidene)-4-piperidone (19): Pyridine (1 ml) and acetic anhydride (110 μl, 1.15 mmol) was added to a solution of compound 1 (300 mg, 0.96 mmol) in anhydrous methylene chloride (5 ml). The reaction mixture was stirred at room temperature for 16 h, diluted with methylene chloride, washed with water. The organic phase was separated, dried with anhydrous sodium sulfate, concentrated, and separated on a silica column using 60% ethyl acetate in hexanes. N-acetyl derivative, 19, was obtained as a yellow solid (311 mg, 91% yield). $R_f$ (60:40 ethyl acetate:hexanes)=0.45. $^1$H NMR (300 MHz, CDCl$_3$): δ 7.89, 7.84 (2s, 2H, C=CH), 7.37 (q, 2H, Ar—H, J=7.6), 7.30-7.05 (m, 6H, Ar—H), 4.77, 4.54 (2s, 4H), 1.88 (s, 3H, CH$_3$). $^{13}$C NMR (75 MHz, CDCl$_3$): δ 185.97, 169.16, 162.42 (d, J=40.3), 159.08 (d, J=39.1), 133.39 (d, J=13.8), 131.47 (d, J=8.9), 131.14 (d, J=4.0), 130.21, 124.40 (d, J=3.7), 124.32 (d, J=3.7), 122.55 (d, J=13.5), 122.22 (d, J=14.4), 116.20 (d, J=21.6), 115.95 (d, J=21.6), 47.16 (d, J=5.1), 45.32 (d, J=3.7), 21.01. ESI Mass calculated for $C_{21}H_{18}F_2NO_2$ (M+H)$^+$ 354.13. found 354.13.

N-(4-Methylbenzenesulfonyl)-3,5-bis(2-fluorobenzylidene)-4-piperidone (20): Tosyl (4-methylbenzenesulfonyl)chloride (68 mg, 0.35 mmol) and pyridine (1 ml) were added to a solution of compound 1 (100 mg, 0.32 mmol) in anhydrous methylene chloride (3 ml). The reaction mixture was stirred at room temperature for 16 h, diluted with methylene chloride, and washed with water. The organic phase was dried with anhydrous sodium sulfate, and concentrated to obtain a yellow solid. The crude compound was purified on a silica column using 50% ethyl acetate in hexanes (128 mg, 86% yield). $R_f$ (30:70 ethyl acetate:hexanes)=0.60. $^1$H NMR (400 MHz, CDCl$_3$): δ 7.72 (s, 2H, C=CH), 7.46-7.32 (m, 4H, Ar—H), 7.24-7.10 (m, 8H, Ar—H), 4.49 (s, 4H), 2.40 (s, 3H, CH$_3$). $^{13}$C NMR (100 MHz, CDCl$_3$): δ 184.00, 160.69 (d, J=251.6), 144.28, 134.65, 131.81 (d, J=4.3), 131.76 (d, J=4.3), 130.72, 129.75, 127.58, 124.40 (d, J=4.1), 122.25 (d, J=13.8), 116.16 (d, J=21.8), 47.38 (d, J=4.8), 21.60. ESI Mass calculated for $C_{26}H_{21}F_2NNaO_3S$ (M+Na)$^+$488.11. found 488.07.

NHS ester of compound 12, 4-oxo-4-[3,5-bis(2-fluorobenzylidene-4-piperidone-1-ylcarbonyl)-N-hydroxysuccinimidyl butanoic ester] (21): Compound 21 was synthesized as an intermediate in the synthesis of 22 and 24. N-hydroxy succinimide (88 mg, 0.77 mmol) and dicyclohexyl carbodiimide (158 mg, 0.84 mmol) were added to a solution 12 (290 mg, 0.70 mmol) in dry methylene chloride (4 ml). The reaction was allowed to occur with stirring at room temperature for 16 h. Dicyclohexyl urea was filtered-off on a Buchner funnel, and the filtrate was concentrated to dryness to obtain the NHS ester as a yellow solid (295 mg, 81% yield). $R_f$ (10:90 methanol:chloroform)=0.80. $^1$H NMR (300 MHz, CDCl$_3$): δ 7.92, 7.88 (2s, 2H, C=CH), 7.39 (t, 4H, Ar—H, J=7.0), 7.27-7.10 (m, 4H, Ar—H), 4.81 (s, 2H), 4.57 (s, 2H), 2.86 (t, 2H, J=6.7), 2.90-2.75 (m, 6H, CH$_2$, NHS). ESI Mass calculated for $C_{27}H_{22}F_2N_2NaO_6$ (M+Na)$^+$531.13. found 531.00.

Glucosamine conjugate, 4-oxo-4-[3,5-bis(2-fluorobenzylidene-4-piperidonylcarbonyl)-2-glucose butanamide] (22): Glucosamine (13 mg, 0.06 mmol) was added to a solution (30 mg, 0.06 mmol) of 21 in dry pyridine (0.3 ml), and stirred at 90° C. for 3 h. The compound was eluted with (20:80 methanol:chloroform) on a silica column to obtain 22 as a yellow solid (23 mg, 68% yield). $^1$H NMR (300 MHz, CDCl$_3$): δ 8.67 (br, 1H, NH), 7.73 (s, 2H, C=CH), 7.65-7.50 (m, 4H, Ar—H), 7.40-7.30 (m, 4H, Ar—H), 7.20 (d, 1H, H-1', J=4.5), 5.59 (br, 1H, OH), 5.17 (t, 1H, H-2', J=4.3), 4.75 (s, 4H), 3.80-3.50 (m, 4H, H-3', 4', CH$_2$), 3.15 (t, 2H, CH$_2$, J=5.8), 2.90-2.75 (m, 5H, H-5', 6', 6", 2*OH). ESI Mass calculated for $C_{29}H_{31}F_2N_2O_8$ (M+H)$^+$573.20. found 573.00.

2-[3,5-Bis(2-fluorobenzylidene-4-piperidone-1-yl)-N-(4-fluorobenzyl)acetamide] (23): Commercially available 4-fluorobenzylamine (500 mg, 3.99 mmol) was reacted with bromoacetyl bromide (380 μl, 4.39 mmol) in presence of triethylamine (600 μl, 4.39 mmol) at room temperature for 20 min. The progress of the reaction was monitored by a faster moving spot in silica TLC (60% ethyl acetate in hexanes). At the end of the reaction, the mixture was filtered, and the solvent was dried to obtain 2-bromo-N-[4-fluorobenzyl]acetamide. Potassium iodide (166 mg, 1 mmol) and Cs$_2$CO$_3$ (325 mg, 1 mmol) and 2-bromo-N-(4-fluorobenzyl)acetamide (270 mg, 1.20 mmol) were added to the compound 1 (311 mg, 1 mmol) in DMF (2 ml). The reaction mixture was heated at 95° C. for 60 min. The solvent was evaporated to dryness, and the residue was dissolved in chloroform. After brine and water wash, the organic phase was dried over anhydrous sodium sulfate, and concentrated to obtain a crude yellow solid. The crude compound was recrystallized from chloroform and hexanes to get the title compound 23 as a yellow crystalline solid (252 mg, 53% yield). $^1$H NMR (300 MHz, CDCl$_3$): 7.93 (s, 1H), 7.83 (s, 2H, C=CH), 7.75-7.02 (m, 8H, Ar—H), 6.97 (dd, 2H, Ar—H, J=7.2, 2.1), 6.68 (t, 2H, Ar—H, J=7.2), 4.19 (s, 2H, benzylic), 4.17 (s, 2H, benzylic), 3.76 (s, 4H). ESI Mass calculated for $C_{28}H_{23}F_3N_2NaO_2$(M+Na)$^+$499.16. found 499.91.

Synthesis of series E compounds: In this series a few conjugates of compound 1 containing a long lipid chain at piperidinyl nitrogen were synthesized.

4-[3,5-Bis(2-fluorobenzylidene)-4-oxo-piperidin-1-yl]-N-hexadecyl-4-oxo-butyramide (24): Hexadecylamine (14 mg, 0.06 mmol) was added to a solution of compound 21 (30 mg, 0.06 mmol) in dry pyridine (0.3 ml) and stirred at 90° C. for 3 h. After completion of the reaction, the solvent was dried, and the crude compound was eluted with (20:80 methanol:chloroform) on a silica column to obtain compound 24 as a yellow solid (22 mg, 59% yield). $^1$H NMR (300 MHz, CDCl$_3$): δ 7.89, 7.87 (2s, 2H, C=CH), 7.53-7.10 (m, 8H, Ar—H), 6.11 (t, 2H, J=4.9), 4.75, 4.62 (2s, 4H), 3.11 (q, 2H, J=6.6), 2.48 (t, 2H, J=5.6), 2.36 (t, 2H, J=6.2), 1.87 (br, 2H), 1.71-1.64 (m, 2H), 1.40-1.08 (m, 22H), 0.85 (t, 3H, J=6.6, $CH_3$). ESI Mass calculated for $C_{39}H_{52}F_2N_2O_3(M+H)^+$ 635.40. found 635.20.

N-Stearoyl-3,5-bis(2-fluorobenzylidene)-4-piperidone (25): Triethylamine (0.4 ml, 2.85 mmol) was added to a solution of compound 1 (300 mg, 0.96 mmol) in ice-cold 1,2 dichloroethane. A solution of stearoyl chloride (450 mg, 1.49 mmol) in 1,2-dichloroethane was added drop-wise to the ice-cold solution of compound 1. The reaction mixture was stirred at room temperature for 16 h. After completion of the reaction, 10% potassium carbonate solution (10 ml) was added, and stirred for 30 min. The organic phase was separated, dried with anhydrous sodium sulfate, and concentrated to obtain a shiny solid of 25 (373 mg, 67% yield). $^1$H NMR (300 MHz, $CDCl_3$): δ 7.92, 7.89 (2s, 2H, C=CH), 7.50-7.35 (m, 4H, Ar—H), 7.30-7.14 (m, 4H, Ar—H), 4.79, 4.55 (2s, 4H), 2.44 (td, 2H, J=7.3, 2.3), 2.09 (t, 2H, J=7.6), 1.65 (t, 2H, J=7.0), 1.41 (t, 2H, J=7.3), 1.40-1.05 (m, 24H), 0.87 (t, 3H, J=6.7, $CH_3$). $^{13}$C NMR (75 MHz, $CDCl_3$): δ 172.05, 133.77, 133.40, 133.48, 130.76, 130.23, 124.29, 116.39, 116.09, 115.81, 46.45, 43.48, 35.26, 33.08, 31.92, 29.69, 29.37, 28.86, 25.06, 24.21, 22.69, 14.12. ESI Mass calculated for $C_{37}H_{50}F_2NO_2(M+H)^+$578.38. found 578.40.

3-[3,5-Bis-(2-fluorobenzylidene)-4-oxo-piperidine-1-carbonyl]-pentadec-4-enoic acid (26): Dodecenyl succinic anhydride (179 mg, 0.67 mmol) and triethylamine (0.18 ml, 1.29 mmol) were added to a solution of compound 1 (200 mg, 0.64 mmol) in dry methylene chloride and stirred at room temperature for 2 h. The mixture was chromatographed on a silica column, and the title compound 26 was eluted from the column using 10% methanol:chloroform as eluant. The compound 26 was obtained as yellow thick syrup (352 mg, 95% yield). $R_f$(10:90 methanol:chloroform)=0.26. $^1$H NMR (300 MHz, $CDCl_3$): δ 7.90-7.80 (m, 3H, 2C=CH, vinyl-H), 7.42-7.00 (m, 9H, Ar—H, vinyl-H), 5.30-5.05 (m, 4H), 5.00-4.95 (m, 2H), 4.82-7.78 (m, 2H), 4.65-4.40 (m, 4H), 2.85-2.70 (m, 2H), 2.50-2.40 (m, 2H), 2.30-2.10 (m, 4H), 2.08-1.90 (m, 4H), 1.90-1.70 (m, 2H), 0.91 (t, 3H, J=6.4, $CH_3$). $^{13}$C NMR (75 MHz, $CDCl_3$): δ 185.81, 173.27, 170.15, 161.96 (d, J=55.2), 159.45 (d, J=53.7), 135.38, 134.29, 133.30, 133.10, 131.52, 130.78, 130.51, 125.33, 124.78, 124.23 (d, J=3.1), 122.47 (d, J=13.3), 122.22 (d, J=14.8), 116.32 (d, J=18.9), 116.22 (d, J=21.8), 115.93 (d, J=25.7), 46.45 (d, J=3.2), 46.48 (d, J=3.1), 35.27, 33.08, 31.92, 29.9, 29.19, 29.44, 29.16, 28.86, 25.05, 24.21, 22.67, 14.13. ESI Mass calculated for $C_{35}H_{41}F_2NNaO_4$ $(M+Na)^+$600.29. found 600.20.

3-[3,5-Bis-(2-fluorobenzylidene)-4-oxo-piperidine-1-carbonyl]-heptadec-4-enoic acid (27): Tetradecenyl succinic anhydride (198 mg, 0.67 mmol) and triethylamine (0.18 ml, 1.29 mmol) were added to a solution of compound 1 (200 mg, 0.64 mmol) in methylene chloride. The reaction mixture was stirred at room temperature for 2 h. The crude compound was passed through silica column, and using 10% methanol:chloroform as eluant, compound 27 was obtained as yellow thick syrup (357 mg, 92% yield). $R_f$(10:90 methanol:chloroform) =0.31. $^1$H NMR (300 MHz, $CDCl_3$): δ 7.90-7.80 (m, 3H, 2C=CH, vinyl-H), 7.45-7.00 (m, 9H, Ar—H, vinyl-H), 5.40-4.50 (m, 9H), 2.70-1.70 (m, 9H), 1.40-1.20 (m, 12H), 0.93 (t, 3H, J=6.6, $CH_3$). $^{13}$C NMR (75 MHz, $CDCl_3$): δ 186.10, 174.03, 170.76, 162.6 (d, J=51.2), 133.75, 133.55, 132.36, 130.75, 126.68, 124.22 (d, J=9.8), 115.98 (d, J=21.2), 44.75, 32.46, 31.90, 22.67, 14.12. ESI Mass calculated for $C_{37}H_{45}F_2NNaO_4$ $(M+Na)^+$628.32. found 628.27.

3-[3,5-Bis-(2-fluorobenzylidene)-4-oxo-piperidine-1-carbonyl]-heneicos-4-enoic acid (28): Octadecenyl succinic anhydride (235 mg, 0.67 mmol) and triethylamine (0.18 ml, 1.29 mmol) were added to a solution of compound 1 (200 mg, 0.64 mmol) in methylene chloride. Compound 28 was purified as described above, and was obtained as yellow syrup (395 mg, 93% yield). $R_f$(10:90 methanol:chloroform)=0.32. $^1$H NMR (300 MHz, $CDCl_3$): δ 7.88-7.82 (m, 3H, 2C=CH, vinyl-H), 7.40-7.05 (m, 9H, Ar—H, vinyl-H), 5.21-5.14 (m, 2H), 5.01-4.90 (m, 2H), 4.68-4.50 (m, 8H), 2.80-2.70 (m, 2H), 2.66-2.41 (m, 4H), 2.28-2.19 (m, 2H), 1.85-1.77 (m, 2H), 1.30-1.05 (m, 16H), 0.78 (t, 3H, J=6.7, $CH_3$). $^{13}$C NMR (75 MHz, $CDCl_3$): δ 186.09, 179.02, 176.63, 174.01, 170.76, 162.41 (d, J=30.8), 159.08 (d, J=30.5), 133.63 (d, J=9.2), 133.53 (d, J=9.3), 131.58, 130.18, 126.45, 125.53, 122.48, 115.98, 46.32, 44.77, 43.33, 41.79, 37.98, 35.08, 33.58, 32.47, 32.42, 31.90, 29.70, 29.29, 22.67. ESI Mass calculated for $C_{41}H_{53}F_2NNaO_4$ $(M+Na)^+$684.38. found 684.40.

4-[3,5-Bis-(2-chlorobenzylidene)-4-oxo-piperidin-1-yl]-4-oxo-2-butenoic acid (29): This compound was synthesized in a manner similar to that of the series C compounds. From compound 3 (547 mg, 1.59 mmol), maleic anhydride (171 mg, 1.75 mmol) and triethylamine (670 μl, 4.76 mmol), the title compound 29 was obtained as yellow solid (661 mg, 94% yield). $R_f$(10:90 methanol:chloroform)=0.42. $^1$H NMR (300 MHz, $CDCl_3$): δ 10.42 (br s, 1H, COOH), 7.97, 7.89 (2s, 2H, C=CH), 7.50-7.05 (m, 8H, Ar—H), 6.28 (d, 1H, CH=CH, J=11.7), 5.86 (d, 1H, CH=CH, J=11.7), 4.77, 4.55 (2s, 4H). $^{13}$C NMR (75 MHz, $CDCl_3$): δ 185.67, 167.20, 167.17, 135.92, 135.18, 135.04, 134.75, 132.51, 130.76, 129.99, 126.93, 118.13, 110.00, 46.79, 42.87. ESI Mass calculated for $C_{23}H_{18}Cl_2NO_4$ 442.06 $(M+H)^+$. found 442.08

Biology

Cell Culture and drug treatment: Human lung adenocarcinoma cell line NCI-H441 (ATCC Number: HTB-174) was obtained from the American Type Culture Collection (Manassas, Va.). H441 cells were maintained at 37° C. with 5% $CO_2$ in McCoy's 5A Medium (Invitrogen, Carlsbad, Calif.) supplemented with 5% heat-inactivated fetal bovine serum (FBS). All media contained gentamicin at 50 μg/ml (GIBCO Laboratories, Grand Island, N.Y.). Other cells lines (PANC-1, MiaPaCa-2 and PC-3) were also similarly maintained, except that the cell culture medium was RPMI 1640 instead of McCoy's.

To evaluate the anti-proliferative activity of synthesized bis(2-fluorobenzylidene)-4-piperidone and its derivatives, the cells were seeded in 96-well flat-bottom tissue culture plates at a density of $10 \times 10^3$ cells per well. The cells were allowed to attach and grow overnight. The test compounds were solubilized in dimethyl sulfoxide (DMSO), filtered through 0.2 μm nylon filter and added to cells at 1, 10, 25 and 100 μM concentrations in culture medium supplemented with 5% FBS. The DMSO concentration was maintained at 0.1% per well. Control wells received equivalent volume of DMSO without any test compounds. The cells were allowed to remain in the treatment medium for 24, 48 and 72 hours.

Cell Proliferation: The total number of cells after the treatment period was estimated by the hexosaminidase assay. [Landegren, 1984] Briefly, the medium was removed and hexosaminidase substrate solution in citrate buffer pH 5 (7.5 mM), p-nitrophenol-N-acetyl-beta-D-glucosaminidase (Calbiochem, San Diego, Calif.) was added at 60 μl per well. The plate was incubated at 37° C. in 100% humidity for 30 minutes, before stopping the reaction with 90 μl of 50 mM glycine containing 5 mM of EDTA (pH 10.4). The absorbance was measured at 405 nm. The experiments were conducted in triplicate, and repeated at least twice. The data were analyzed as percent of control, where the control wells were treated with equivalent amounts of DMSO alone, and the analyzed data was presented as average±standard error of mean. The differences among mean values were deemed significant at p<0.05.

For $IC_{50}$ calculations, a plot between the drug concentration and hexosaminidase activity was generated and the data was fitted either linearly or exponentially. The best fit was used for further processing of data. $IC_{50}$ was obtained by determining the concentration of compounds (µM) resulting in 50% of cell death after 24 h of treatment.

Transmission Electron Microscopy (TEM): TEM was performed after 24 hour treatment with 1 and 10 µM of compound 1 or compound 29 (CLEFMA). The cells were fixed in 0.1M sodium cacodylate buffer containing 4% paraformaldehyde (PFA) and 2% glutaraldehyde for 4 h at room temperature. The samples were post-fixed in 1% osmium tetroxide for 1.5 h and washed with 0.1M sodium cacodylate buffer, followed by dehydration in an ethanol series of 50%, 60%, 75%, 85%, and 95% for 15 minutes each. The cells were washed twice in 100% Ethanol and passed through a series of epon-araldite (6.2 g epon+4.4 g araldite+12.4 g of dodecenyl succinic anhydride+0.8 g N,N-dimethylbenzylamine) solution in ethanol, [Matsko et al., 2005] before embedding the cells in epon-araldite resin. Finally, 100 nm sections were cut using a microtome, and the sections were placed on glow-discharged 300 mesh Copper grids. The ultrasections were stained with Sato's lead (mixture of calcinated lead citrate, lead nitrate, lead acetate and sodium citrate), and observed by a Hitachi H-7600 Transmission Electron Microscope at 2500× (Oklahoma Medical Research Foundation Imaging and core facility, Oklahoma City).

Actin and Hoechst 33342 nuclear staining: H441 cells were grown for 24 h in an 8-well Lab-Tek chamber slide (Nalgene Nunc, Rochester, N.Y.), and treated with compound 1 or 29 (CLEFMA) for 24 h. After washing the cells twice with phosphate-buffered saline (PBS), the cells were fixed with 4% paraformaldehyde for 20 min at room temperature. The fixed cells were twice washed with PBS, and permeabilized for 10 min with 0.5% Triton X-100 in PBS. The cells were incubated for 20-30 min with rhodamine phalloidin solution (500 µl, 100 nM) made by diluting 3.5 µl of methanolic stock (14 µM in methanol) to 500 µl with PBS. After washing with PBS, the cell layer was stained with Hoechst dye (2 µg/ml in PBS) for 15 min. The stained cells were washed again, air dried, and mounted in Vectashield medium (Vector Laboratories, Burlingame, Calif.). The cell mounts were visualized with a DM4000B fluorescent microscope (Leica Microsystems Inc, Bannockburn, Ill.) using a filter cube A4 equipped with excitation filter BP 360/40 and BP 560/40 for Hoechst and phalloidin, respectively.

EXAMPLE 2

Lung cancer is one of the leading causes of cancer-related deaths in the world. According to the report from the U.S. Cancer Statistics Group, 158,683 people in the United States died from lung cancer in the year 2007 [Available at http://cdc.gov/uscs]. About 60% people with lung cancer die within one year of being diagnosed with the disease. In non-small cell lung carcinoma (NSCLC), surgery is the only curative treatment modality [Burdett et al., 2007]. Meta-analysis of clinical data suggests that up to 85% of the NSCLC patients depend on systemic chemotherapy as part of the overall management [Akerley et al., 1999]. However, despite advances in understanding of cancer biology and potential molecular targets, lung cancer chemotherapy remains palliative in nature. The poor clinical response to anticancer drugs in lung cancer patients has led to a continuous search for newer and more potent compounds. A novel synthetic second generation curcumin analog, CLEFMA, was synthesized, and its efficacy as a potent anti-proliferative agent in various cancer cell lines was demonstrated above in Example 1. CLEFMA is a derivative of a previously reported diphenyldifluoroketone called EF24 [Adams et al., 2004], and is chemically named as 4-[3,5-bis(2-chlorobenzylidene-4-oxo-piperidine-1-yl)-4-oxo-2-butenoic acid].

The pre-formulation studies on CLEFMA depicted it as a highly hydrophobic drug with octanol-water partition coefficient of 5.66. It was hypothesized that liposomes might serve as a vehicle for CLEFMA preparation meant for parenteral administration. Parenteral liposome formulations of lipophilic drugs are challenging. Incorporation of a lipid-partitioning drug in liposomes may produce structurally instable liposomes, resulting in burst-release of drug, rapid clearance from the body, and/or overall poor efficacy. The entrapment of cyclodextrin (CD)-based inclusion complexes (IC) inside the liposomes can be a reliable and effective method of encapsulation of hydrophobic drugs. This strategy was first reported by Gregoriades [McCormack et al., 1994], and has recently been used for the encapsulation of isotretinoin [Kaur et al., 2010].

Arguably, the CD-based IC themselves could be used as a water soluble product for intravenous administration. However, encapsulating drug-CD IC inside liposomes has several potential advantages. Encapsulation not only modifies the biodisposition of IC, but also prolongs its clearance. If desired, the outer lipid layer of liposomes could be used to attach ligands to target drug delivery. Liposomes are relatively benign drug delivery vehicles, and many liposomal products are in clinical use [Samad et al., 2007; Schwendener, 2007]. An enhanced permeability and retention (EPR) effect enables liposomes to be selectively trapped in the tumor tissue for an extended period because of high vascular density, larger intracellular space and high vascular permeability [Kaasgaard et al.; Maeda et al., 2006]. Besides EPR-mediated accumulation in tumor, liposomal carriers modify the pharmacokinetics and tissue distribution of incorporated drugs. Evidently, the size, surface charge and composition of lipid bilayer have strong influences on liposome kinetics [10]. The altered behavior of liposome-encapsulated drug in biological system is often manifested as enhanced efficacy as well as reduced side-effects of drugs [Huwyler et al., 2008].

Recently, the inventors reported optimization of the drug-in-CD-in-liposome approach for EF24, a close analog of CLEFMA [Agashe et al., 2010]. The liposomes were designed to facilitate labeling with single photon-emitting radionuclide Tc-99m for imaging of their biodistribution after administration. In this Example, the in vivo efficacy of CD-enabled liposomal CLEFMA was investigated in a lung cancer xenograft model in nude rats. Positron emission tomography (PET) was employed as a non-invasive imaging tool for confirming anti-proliferative efficacy of CLEFMA liposomes. At the same time, CLEFMA liposomes were labeled with Tc-99m for single photon emission tomography (SPECT). The results of this investigation suggest that liposomal formulation provides an acceptable platform for parenteral delivery of curcuminoids such as CLEFMA.

Materials and Methods of Example 2

Formation of CLEFMA Inclusion Complex (IC).

CLEFMA was synthesized and characterized according to the methods described in Example 1. A phase solubility analysis of CLEFMA was performed according to the published method [Higuchi et al., 1965], and ICs of CLEFMA with HPβCD in the solution phase were prepared as reported previously [Agashe et al., 2010]. Briefly, an excess of CLEFMA was added to 5 ml of HPβCD solution (1 g/ml). The mixture was continuously agitated on a shaker incubator at 25° C. for 72 h. After allowing settling of coarse particulate matter for 6 h, the supernatant was centrifuged at 14,000 rpm for 15 min to obtain a clear supernatant free of any insoluble material. The solution was passed through a sterile 0.22 μm cellulose acetate filter, and the amount of HPβCD-solubilized CLEFMA was estimated spectrophotometrically at 320 nm. The phase solubility diagram was constructed by plotting the estimated CLEFMA concentration against HPβCD concentrations. The stability constant was calculated from the phase diagram using the following equation—

$$K_{1:1} = \text{Slope}/[S_0(1-\text{Slope})], \text{ where } S_0 \text{ is CLEFMA solubility in the absence of HPβCD}$$

The complexation efficiency (CE) was calculated as a product of $S_0$ and $K_{1:1}$ Preparation of Liposomes.

CLEFMA liposomes were prepared by high pressure homogenization [Agashe et al., 2009]. A lipid composition of 1,2-disteroyl-sn-glycero-3-phosphatidylcholine:cholesterol:dipalmitoylphosphatidyl glycerol (DSPC:CHO:DMPG as 50:50:5 mol %) was dissolved in a mixture of chloroform:methanol (2:1) and transferred to a round bottom flask. The solvent mixture was evaporated at 58° C. on an R-210 rotavapor (Buchi Corporation, New Castle, Del.) to obtain a thin film of lipids. Any residual traces of organic solvent were removed by keeping the film under high vacuum for 12 h. The phospholipid film was rehydrated with Hypure™ endotoxin-free, cell culture grade water (Hyclone, Logan, Utah), maintaining the total phospholipid concentration to 12 mM (total lipid 2 g/dL). The resulting suspension of multilamellar vesicles was subjected to eight freeze-thaw (FT) cycles. An FT cycle consisted of snap-freezing the suspension in liquid nitrogen followed by immediate thawing in a 58° C. water bath. The liposome suspension was lyophilized for 48 h in a Triad lyophilizer (Labconco, Kans. city, MO). The dried mass was rehydrated with sterile aqueous solution of CLEFMA-HPβCD IC.

To enable Tc-99m labeling, the rehydration mixture also contained glutathione (100 mM, pH 6.8); the lipid concentration during rehydration was maintained at approximately 12 mM. The liposome suspension thus formed was homogenized in Emulsiflex C3 homogenizer (Avestin Inc, Canada). A three-step homogenization process was adopted, where the mixture was subjected to pressures of 15K PSI (1 cycle), 20K PSI (2 cycles), and 23K PSI (1 cycle). Each step was separated by a cooling period of 15 min during which the preparation was kept at 4° C. The liposomes were separated from any un-entrapped material by ultracentrifugation at 50,000 rpm and 4° C. for 40 min (Beckman Optima L-100 XP, Fullerton, Calif.). The liposome pellet was washed three times with PBS (pH 7.4), before re-suspending in PBS. Strict aseptic conditions were maintained during the entire processing.

A control preparation of liposomes was also prepared identically, except that the rehydration solution was devoid of CLEFMA, but contained HPβCD and glutathione.

Characterization of CLEFMA Liposomes.

CLEFMA inside the liposomes was determined by digesting a measured aliquot of liposome suspension in methanol, and spectrophotometrically estimating CLEFMA at 310 nm after appropriate dilution with methanol. Control liposomes (liposomes identical to the CLEFMA-liposomes in all respects but devoid of CLEFMA) were also digested in methanol and used as estimation blank.

Phospholipid concentration in the liposomes was determined by Stewart assay [Stewart, 1980]. A 10 μl aliquot of liposomes was vigorously mixed with a binary system consisting of 2 ml each of chloroform and ferrothiocyanate reagent. The aqueous ferrothiocyanate reagent contained 27.03 g/L ferric chloride hexahydrate and 30.4 g/L ammonium thiocyanate. The color in the chloroform phase was measured at 485 nm and compared to a set of DSPC standards treated in an identical fashion.

The particle size of the liposomes was determined by photon correlation spectroscopy using a Brookhaven particle size analyzer equipped with Mas Option software. Zeta potential of preparations was measured in a Zeta PLUS Zeta potential analyzer (Brookhaven Instruments Corp, Holtsville, N.Y.). For zeta potential, the liposomes (~40 μg of phospholipid) in 1.5 ml of 0.22 μm filtered de-ionized water were scanned at 25° C. for 10 runs, each run consisting of 20 cycles. Zeta potential values were obtained as millivolt±standard error of mean.

The Transmission Electron Microscopy (TEM) was performed at the University of Oklahoma (Norman, Okla.). An ultradilute liposome suspension was stained with a solution consisting of 2.5% phosphotungstic acid and 2.5% trehalose (pH 7). A drop of liposome suspension was first applied to the copper grid, allowed to adsorb on the grid for 2 min, and then blotted with a filter paper. A drop of the stain was added to the wet grid and immediately blotted. TEM images were recorded on a Zeiss 10 electron microscope.

In Vitro Anti-Proliferative Activity of CLEFMA and Liposomes.

Human lung adenocarcinoma cell line NCI-H441 (ATCC # HTB-174) and normal lung fibroblasts LL-24 (ATCC #CCL-151) were obtained from American Type Culture Collection (Manassas, Va.). The cells were maintained at 37° C. with 5% $CO_2$ in RPMI 1640 medium (Invitrogen, Carlsbad, Calif.). The medium was supplemented with 10% heat-inactivated fetal bovine serum and 50 μg/ml of gentamicin (GIBCO Laboratories, Grand Island, N.Y.). For cell proliferation assay, the cells were seeded in 96-well flat-bottom tissue culture plates at a density of $0.5-1\times10^4$ cells per well. The cells were allowed to adhere and grow overnight, followed by treatment with CLEFMA or CLEFMA-liposomes. The concentration of CLEFMA was maintained in the range of 0.1-25 μM in 100 μl of RPMI 1640 medium. For comparison, the cells were also treated with 1 and 10 μM natural curcumin and EF24. EF24 is a potent synthetic curcuminoid and a close analog of CLEFMA [Adams et al., 2004]. All solutions of plain drugs were made in dimethylsulfoxide (DMSO). The concentration of DMSO in the treatment medium was maintained at 0.1%. The control wells received equivalent amounts of DMSO or phospholipid-matched control liposomes. Inhibition of cell proliferation was determined by measuring a decrease in hexosaminidase activity as described by Landegren [Landegren, 1984]. Para-nitrophenol-N-acetyl-beta-D-glucosaminide (60 μl per well) was used as the substrate for the hexosaminidase enzyme. The results of hexosaminidase assay were also confirmed by visualization of cultured cells under a microscope.

Rat Model of Xenograft Lung Cancer.

The animal experiments were performed according to the NIH Animal Use and Care Guidelines and were approved by the Institutional Animal Care Committee of the University of Oklahoma Health Sciences Center. Athymic nude rats (n=12, 200-225 g) were obtained from Harlan Laboratories (Indianapolis, Ind.), and housed in controlled environment with 12 h day/night cycle. The animals were allowed to acclimatize at least one week before inoculation of H441 cells. On the day of tumor implantation, the rats were anesthetized with 2-3% isoflurane in oxygen stream. H441 cell suspension in PBS (0.2 ml, 50 million cells/ml) was subcutaneously injected in the left dorsal thigh region. The rats were returned to their cages, and the tumor was allowed to grow until a visible and palpable tumor was observed in about 15 days post-implantation (Table 4).

Drug Treatment.

The tumor bearing rats were randomized in two groups of six animals each. Intravenous treatment with CLEFMA liposomes was started 15 days post-implantation. The animals were treated with CLEFMA liposomes (treated) or control liposomes (control) every fourth day for a total of six injections (Table 4). The CLEFMA dose was maintained at 40 µg per administration (approximately 0.2 mg/Kg body weight). The control animals received equivalent amounts of phospholipid as control liposomes. On each injection day, the tumor growth was determined by measuring two dimensions using the Vernier calipers to obtain tumor volume=(Length× Width$^2$)/2. Finally, the percent tumor growth inhibition as of 20$^{th}$ day of treatment was determined by using the following formula—% Tumor Growth Inhibition=[(1-T/C)*100], where T and C are mean tumor volume in the treated and control groups, respectively.

Positron Emission Tomography.

After the treatment schedule, the animals were recruited for PET using F-18-fluorodeoxyglucose (FDG) as a biomarker of tumor growth (Table 4). The PET imaging was performed on day 22 of the treatment. FDG (100 µCi, 0.3 ml) was intravenously injected in the tail vein of the rats anesthetized with 2-3% isoflurane in oxygen. The animals were allowed to wake up and returned to their cages for distribution of FDG to take place and the background radioactivity to clear. After 2 h, the animals were anesthetized again and placed inside the PET detector of X-O-PET machine (Gamma Medicaddeas, Northridge, Calif., USA). Static images of FDG accumulation were acquired for 20 min, followed by a fly-mode computed tomography (CT). The PET image was reconstructed using filtered back projection algorithm and fused with the CT image. The fused image was employed for visualization using Amira 3.1 software (Visage Image Inc., San Diego, Calif., USA).

Biodistribution of CLEFMA Liposomes.

After the PET imaging, the rats were allowed to go back into their cages in order to let the F-18 radioactivity ($T_{1/2}$ 110 min) decay completely. The next day, the rats were recruited for a biodistribution study (Table 4). For biodistribution, CLEFMA liposomes were labeled with Tc-99m radionuclide. The radiolabeling was performed using a lipophilic chelate Tc-99m-hexamethyl propylene amine oxime or HMPAO (OUHSC-Nuclear Pharmacy, Oklahoma City, Okla.) and according to the method described previously [Phillips et al., 1992; and Awasthi et al., 2003a and b]. Approximately 0.2 ml liposomes were mixed with equal volume of Tc-99m-HMPAO and allowed to stand at room temperature for 30-45 min. Lipophilic Tc-99m-HMPAO partitions into the liposomes and gets entrapped secondary to its glutathione-mediated conversion into a hydrophilic species [Phillips et al., 1992; and Awasthi et al., 2003a and b]. The Tc-99m-labeled CLEFMA liposomes were separated from any free Tc-99m-HMPAO by gel exclusion chromatography using a PD-10 column.

The Tc-99m-labeled CLEFMA liposomes were evaluated for distribution in tumor bearing nude rats (n=10). On the day of the experiment, the rats were anesthetized with isoflurane gas (2% in oxygen at 2 L/min). A 25G butterfly was secured in the tail vein for administration of radiolabeled preparation. Tc-99m-CLEFMA liposomes (250 µCi, 0.15 ml, 0.26 mg phospholipid) were infused through the tail vein. The rats were randomized into two groups (5 rats each) to study biodistribution at 6 and 24 h post-injection. After specific times, the rats were euthanized by an intraperitoneal overdose of Euthasol (Virbac Corp., Fort Worth, Tex.). Various organs were excised, washed with saline and weighed, and appropriate tissue samples were counted in an automated gamma counter (Perkin-Elmer, Boston, Mass.). Total blood volume, bone and muscle mass were estimated as 5.7%, 10% and 40% of body weight, respectively [Frank et al., 1976; Petty, 1983]. A diluted sample of injected Tc-99m-CLEFMA liposomes served as a standard for comparison. The accumulation of injected preparation in various organs was also calculated as percent of injected radioactivity. All data were corrected for decay of Tc-99m radioactivity ($T_{1/2}$=6 h) and background-subtracted.

For imaging of Tc-99m-CLEFMA liposomes distribution in vivo, single photon emission tomography (SPECT) was used. The tumor-bearing rats were intravenously injected with 1 mCi of Tc-99m-CLEFMA liposomes. Longitudinal images were acquired in a NanoSPECT machine (Bioscan, Washington D.C.) over a 12 h-duration.

Histopathology.

After the animals were euthanized, a part of the liver, lung and kidney were fixed in 10% formalin. The formalin-preserved tissues were used for histology by staining 5 µm sections of paraffin-embedded tissues with H&E stain. The sections were read by a veterinary pathologist (OUHSC, Oklahoma City) in a blinded fashion for the presence of necrosis, hemorrhage, inflammation or any other pathological changes.

Data Analysis.

The biological data was analyzed for significance of difference at p<0.05 using Prism 5.0 (GraphPad Software, Inc., La Jolla, Calif.). The biodistribution data was presented as percent injected dose per gram tissue. Both control and treated groups lost one rat each during the course of investigation. Therefore, the data were censored to allow the dead rats to contribute to the overall results for the entire length of time they were followed, but to statistically remove them after the death was recorded.

Results of Example 2

CLEFMA Inclusion Complex and Liposomes.

Figure 12:
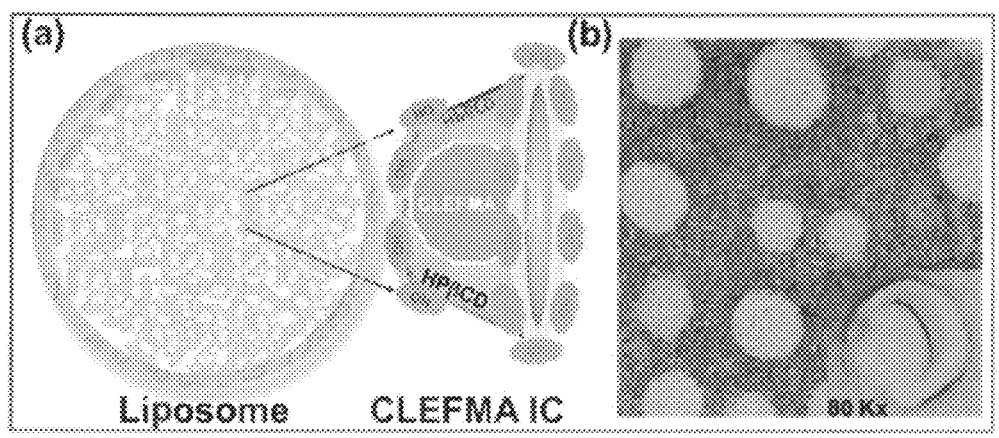
FIG. 12(a) provides a schematic illustration of CLEFMA liposomes using a 'Drug-in CD-in liposome' approach. The inclusion complex of CLEFMA with 2-hydroxypropyl-beta-cyclodextrin (referred to herein as "HPβCD" or "HPBCD") was encapsulated inside the liposomes consisting of distearoylphosphatidylcholine:cholesterol:dimyristoylphosphatidyl glycerol (50:50:5 mol %).
FIG. 12(b) contains a transmission electron micrograph of CLEFMA liposomes (inset, 80,000×).

The phase solubility analysis of CLEFMA in the presence of HPβCD revealed that CLEFMA forms a 1:1 complex with HPβCD on a molar basis. The stability constant of the complex was found to be 0.0126 M$^{-1}$ and the complexation efficiency was approximately 0.57. A stable inclusion complex was obtained with a HPβCD:CLEFMA molar ratio of 53:74. A liposome preparation was formulated using CLEFMA-in CD-in liposome approach (FIG. 12a). The liposomes were prepared using an aqueous solution of the inclusion complex to hydrate the dry lipid powder. The final liposome preparation had approximately 8.05 mM CLEFMA; the CLEFMA: phospholipid molar ratio was 0.133. The phospholipid concentration in the final preparation was 60.3 mg/ml. The % of CLEFMA encapsulated was approximately 19.4%. The size of the liposomes was measured to be 310.3±4.7 and the zeta potential was −43±1.91 mV. The transmission electron micrographs of the liposomes carrying ICs showed uniformly-dispersed spherical structures of liposomes (FIG. 12b).

In Vitro Activity of CLEFMA and Liposomes in Cultured Cells.

Figure 13A:
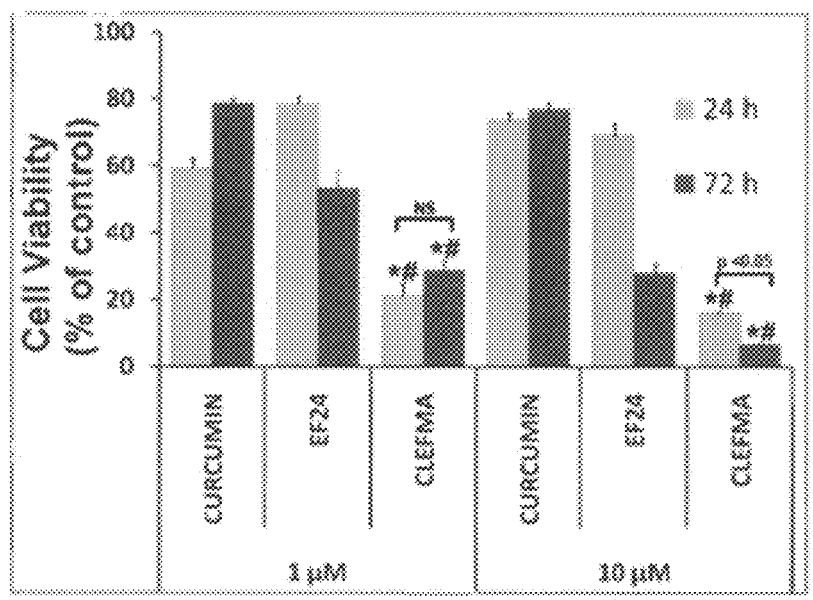
FIG. 13 illustrates cell viability of H441 cells treated with various preparations. (a) CLEFMA, EF24 and curcumin were compared for anti-proliferative efficacy (* and # are p<0.05 against curcumin and EF24, respectively). (b) CLEFMA potently suppresses growth of H441 cells, but not that of normal lung fibroblasts LL-24 (* p<0.05 against respective normal lung fibroblast cells). (c) Liposomal CLEFMA retains the antiproliferative activity of free CLEFMA while remaining non-toxic to normal lung fibroblasts. (d) Presence of glutathione (GSH) inside the liposomes does not have significant impact on anti-proliferative activity of CLEFMA. The data is presented as the mean±sem of results from at least 3 individual experiments performed in triplicates.
Figure 13B:
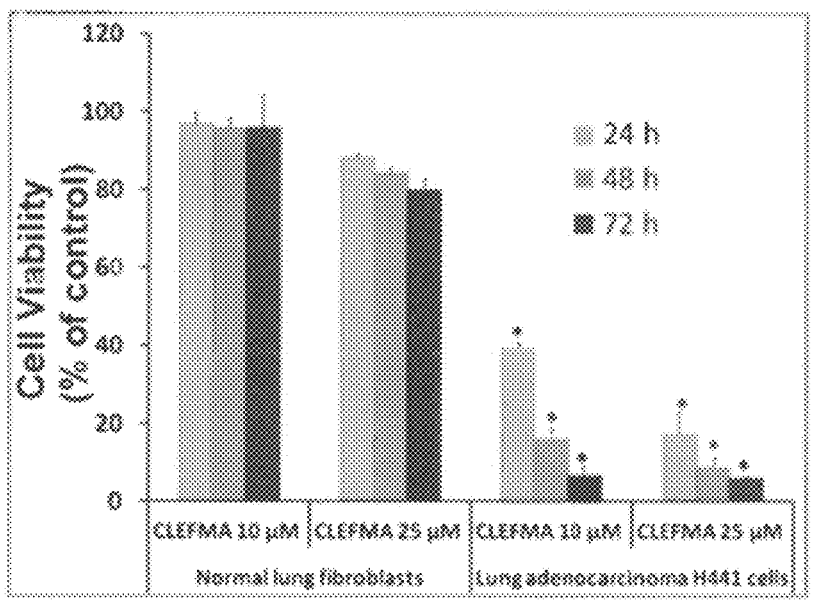
Figure 13C:
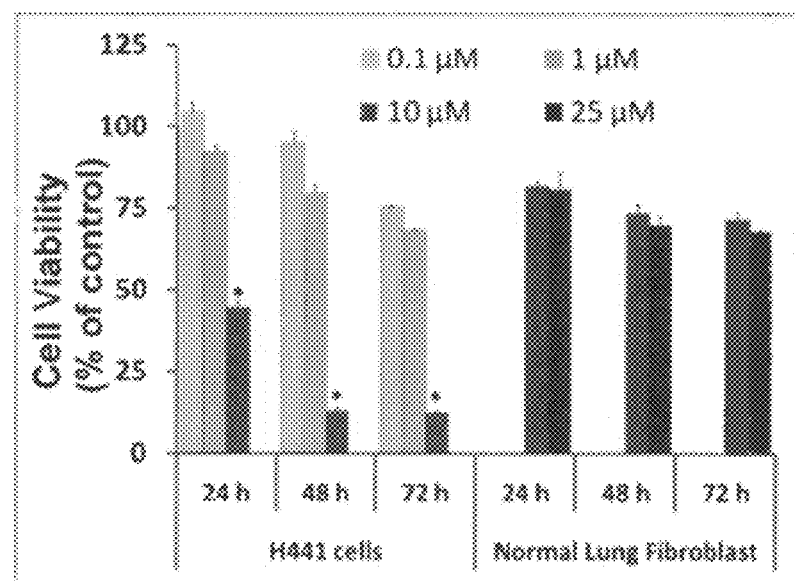
Figure 13D:
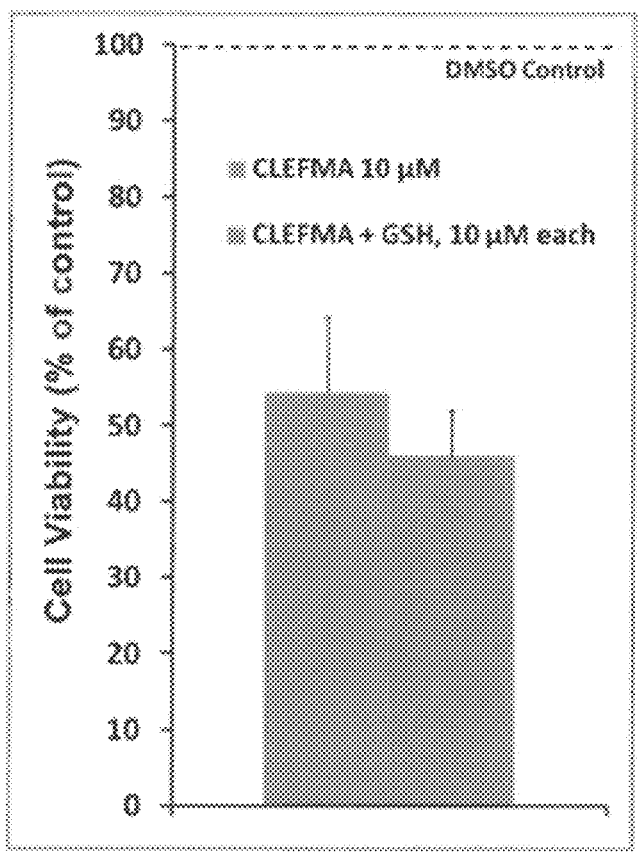

As shown in FIG. 13a, CLEFMA is more potent than curcumin and another synthetic curcuminoid EF24 in suppressing the proliferation of H441 cells. It was further investigated whether CLEFMA is selective in its action on cancer cells. It is clear from the data in FIG. 13b that CLEFMA is antiproliferative to the H441 cancer cells, but is substantially less active against normal lung fibroblasts. Less than 40% of H441 cells survived the 24 h treatment with 10 μM CLEFMA. On the other hand, normal lung fibroblasts essentially remained unscathed under the identical treatment conditions. Liposomal CLEFMA retained the potency of CLEFMA against cancer cells, and maintained the relative innocuousness toward normal lung fibroblasts (FIG. 13c). Since CLEFMA liposomes contained glutathione as a constituent, the effect of glutathione on the activity of CLEFMA in H441 cells was also investigated. Glutathione was not anti-proliferative by itself, but it potentiated CLEFMA activity in a statistically insignificant manner (FIG. 13d).

In Vivo Efficacy of CLEFMA Liposomes in Xenograft Tumor Model.

Figure 14A:
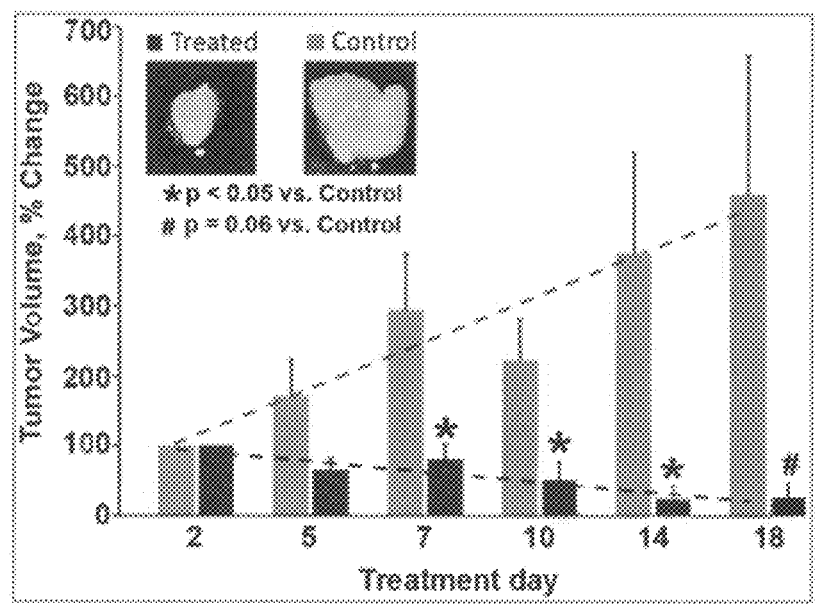
FIG. 14(a) illustrates the change in tumor volume in response to liposomal CLEFMA therapy. The insets show the representative pictures of excised tumors upon necropsy. The dashed lines are the trend line fits to the plotted data. The data is presented as the mean±sem of results from experiments on n=4 (treatment) and n=3 (control) rats.
Figure 14B:
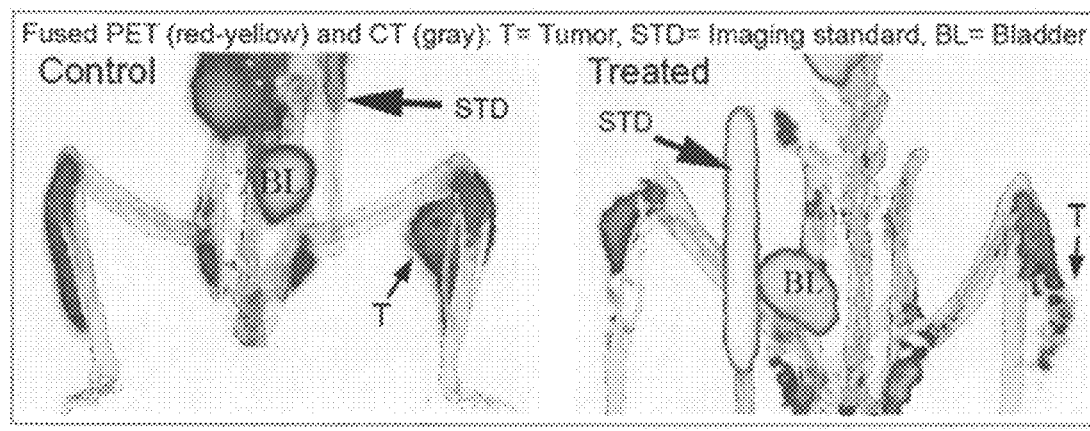
FIG. 14(b) contains a representative set of fused PET/CT images of F-18-FDG accumulation in control and treated rats. The images clearly show that the treated rat has significantly less accumulation of FDG than the control animal.

The anti-proliferative efficacy of CLEFMA liposomes was investigated in a nude rat model of xenografted tumor. FIG. 14a shows the effect of CLEFMA liposome treatment on tumor volume as measured by Vernier calipers. Because of the variability in the initial size of the tumor, the data were calculated as a percent reduction in size compared to the initial tumor size in the same animal. Over a period of 20 days, the tumor volume almost quadrupled in control rats, but reduced to approximately half the initial size in rats receiving CLEFMA liposomes. The percent tumor inhibition was calculated to be approximately 94%. After the last scheduled treatment, the rats were subjected to PET imaging with F-18-FDG. A higher accumulation of FDG signifies a growing tumor. As shown in a representative picture (FIG. 14b), the rat treated with control liposomes accumulated significant amounts of FDG in tumor, but the rat treated with CLEFMA liposomes showed minimal FDG uptake in the tumor.

Biodistribution.

Figure 15A:
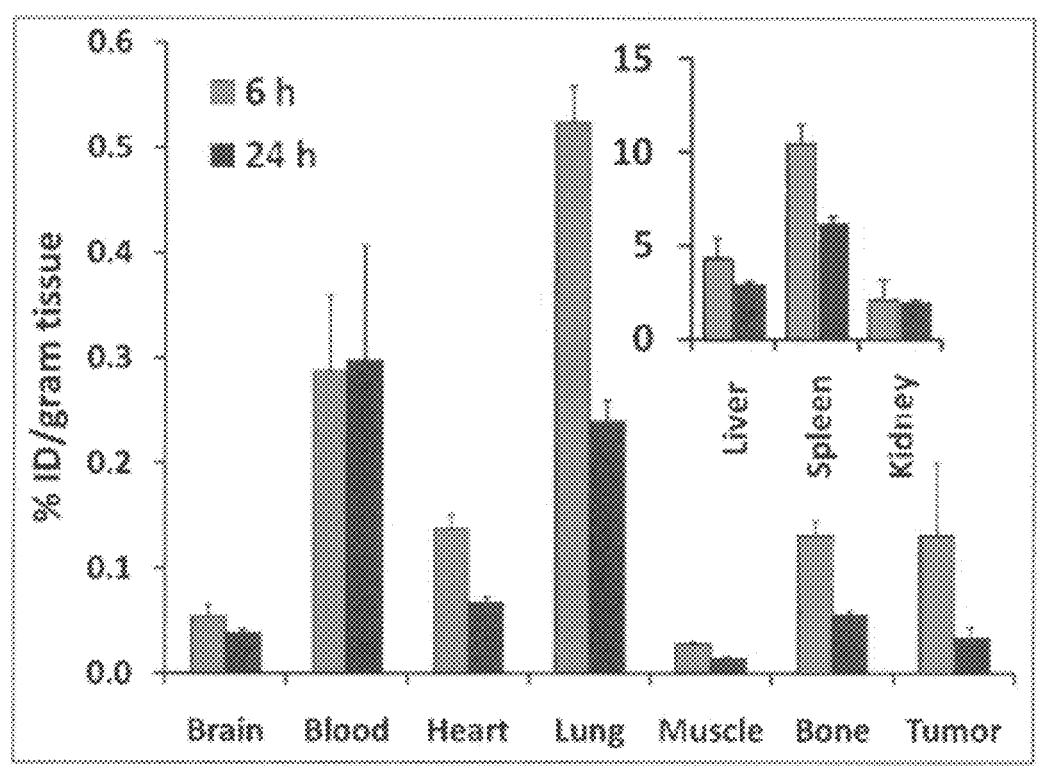
FIG. 15 illustrates biodistribution of Tc-99m-labeled CLEFMA liposomes in rats. (a) Injected dose per gram of tissue. The data is presented as the mean±sem of results from experiments involving n=5 each at 6 h and 24 h. (b) SPECT images of a tumor-bearing rat injected with Tc-99m-labeled CLEFMA liposomes. H441 cells were injected in this rat in the left flank (arrow).
Figure 15B:
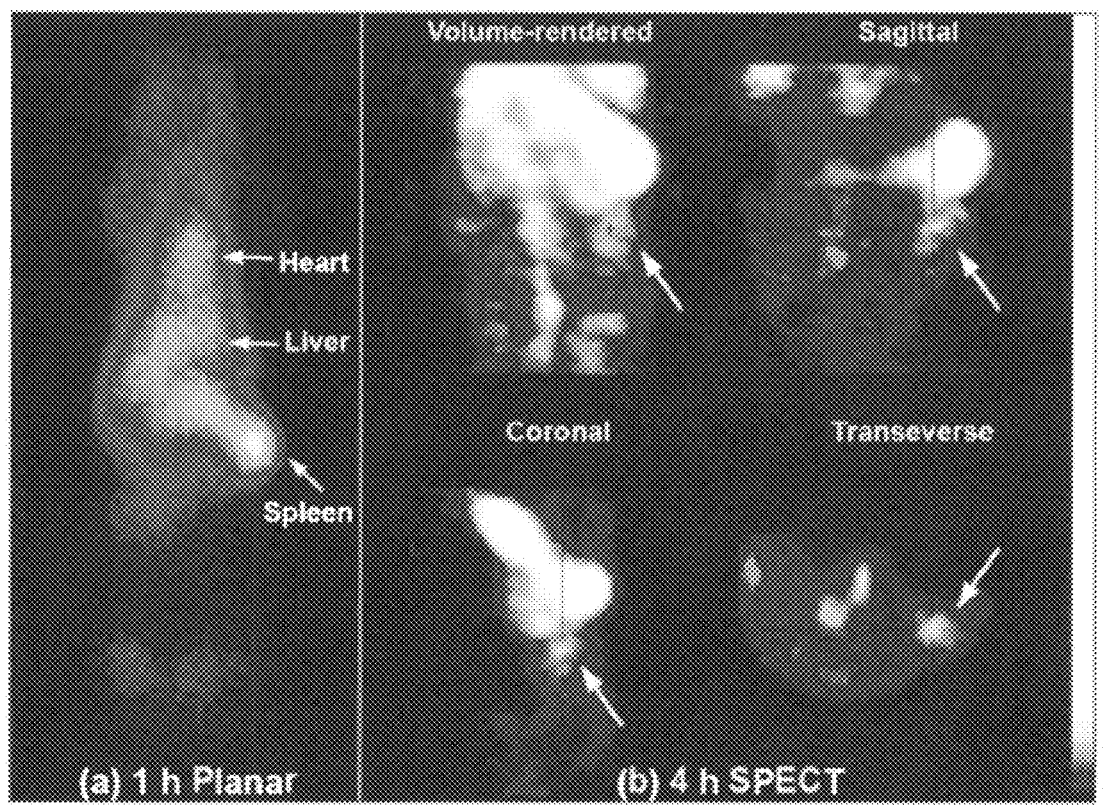

After PET imaging, the rats were subjected to a biodistribution study of CLEFMA liposomes labeled with Tc-99m radionuclide. The labeling efficiency of CLEFMA liposomes exceeded 70% before column separation. After gel exclusion chromatography, more than 95% of radioactivity was found associated with the liposomes. Tc-99m-CLEFMA liposomes were intravenously injected and the rats were euthanized after 6 and 24 h (n=5 each) to collect various organs for counting tissue-associated radioactivity. FIG. 15 shows the accumulation of CLEFMA liposomes in various organs of the rats, suggesting liver as the organ of major uptake. Substantial amounts of injected dose were also found in spleen. There was measurable accumulation of CLEFMA liposomes in the tumors, but the tumor-to-blood ratio was found to be less than unity. Because of the non-stealth nature of the CLEFMA liposomes, it was not surprising to observe their rapid elimination from blood circulation; approximately 5% of injected dose remained in circulation by 6 h post-injection. The differences in 6 and 24 h uptake values of Tc-99m-CLEFMA liposomes in blood, liver and kidney were not significant. FIG. 15b demonstrates the application of imaging in drug delivery. Tc-99m-CLEFMA liposomes were seen accumulating in tumor tissue in the left flank of the rat. The images also confirmed the biodistribution data that the majority of administered liposomes accumulate in liver and spleen.

The weight of the excised tumor also decreased after the treatment with CLEFMA liposomes; the average weight of tumor in treated rats was 0.28±0.14 g compared to 0.49±0.25 g in control rats. Upon necropsy, it was observed that much of the weight and volume in treated tumors was contributed by the accumulation of necrotic fluid because of potent cell death induced by CLEFMA.

Histopathology.

Figure 16:
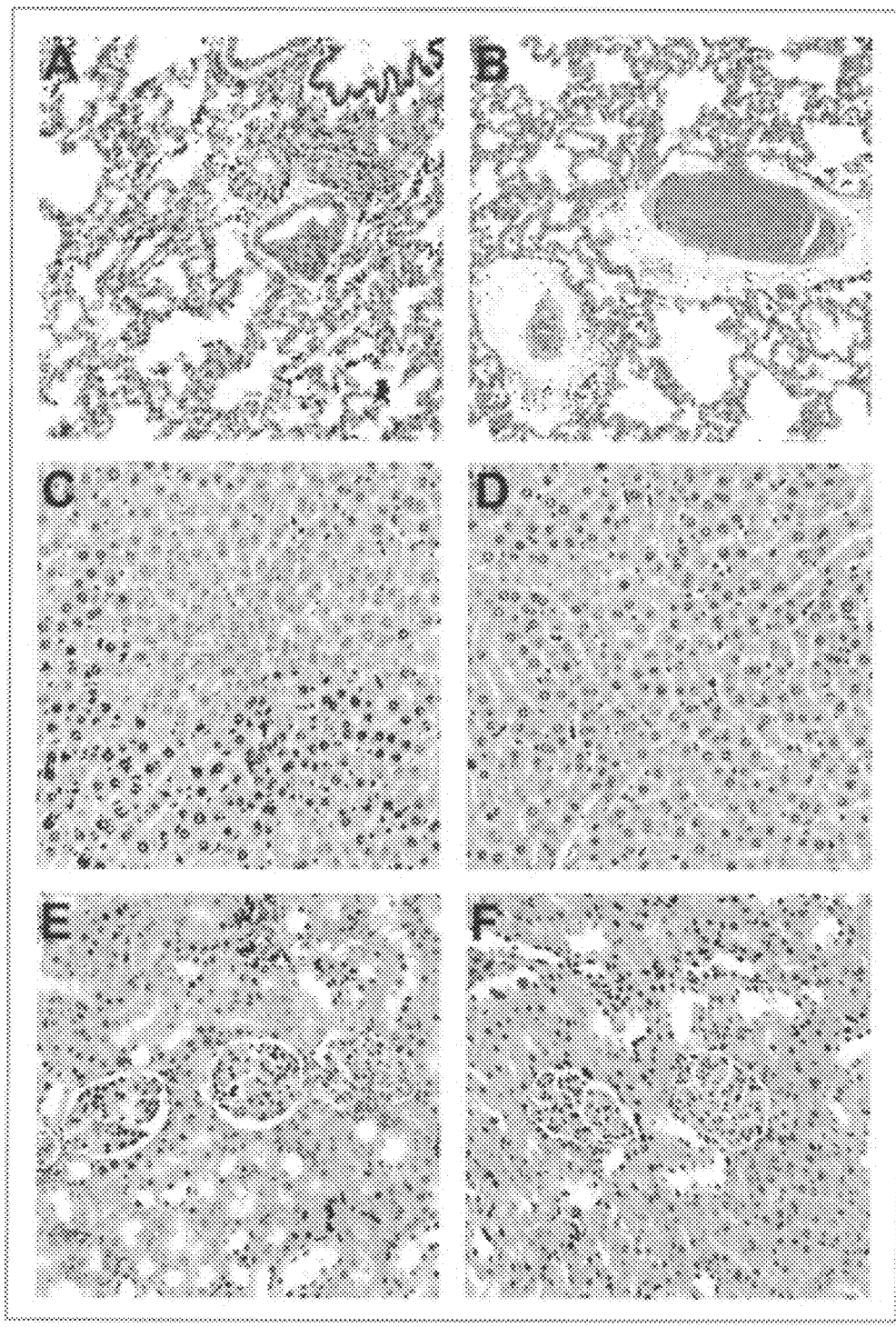
FIG. 16 depicts the histology of lung (A and B), liver (C and D) and kidney (E and F) from control (A, C and E) and treated (B, D and F) rats. As described in the text, no significant observations differentiating treated from control rats were made by the veterinary pathologist.

Histopatholgical examination of lung, liver and kidney showed insignificant differences between the control and treated groups (FIG. 16). Both control and treated rats had moderate to marked pulmonary congestion with no evidence of capillary leakage or acute inflammation, with occasional intra-alveolar macrophage present. Mild intra-alveolar edema and perivascular edema was evident in one rat belonging to the treatment group. These mild changes in lung might have been caused by prolonged gaseous anesthesia before the rats were euthanized. The liver sections of both control and treated rats showed no mitotic figures or apoptotic bodies within the 50 high-power fields. Mild to moderate diffuse hepatocellular vacuolation with mild congestion was occasionally seen in both control and treated liver sections. Similarly, in kidney sections mild corticomedullary congestion with no evidence of tubular or glomerular damage or acute inflammation was observed in either of the groups.

Discussion of Example 2

Chemotherapy has definite palliative benefits in symptomatic relief and improvement in quality of life in lung cancer. A small window of survival and short life-expectancy often necessitates aggressive therapy with a cocktail of highly toxic drugs, radiotherapy and surgery. Availability of medicines with absolute selectivity to cancer is ideal, but an elusive goal. Molecularly-targeted drugs (such as Bevacizumab, Erlotinib, etc.) show promise, but are riddled with their own genuine problems [Danesi et al., 2009]. For instance, heterogeneity in the expression of selective target resulted in the failure of clinical trials of epidermal growth factor receptor inhibitors [Ricciardi et al., 2009]. Even if tumor heterogeneity and emergence of resistance are disregarded, targeted therapies succeed only when patient population is segregated into target-selective subpopulations in a timely fashion [Dempke et al., 2010]. Not surprisingly, a consensus is building that targeted therapies do not dramatically change clinical outcome for most patients [Gridelli et al., 2010; Thomas et al., 2010]. In this Example, a liposome formulation of CLEFMA for lung cancer therapy is described.

CLEFMA is a curcumin analog, and it has its origin in a systematic structure activity relationship performed on a potent anticancer curcuminoid 3,5-bis-(2-fluorobenzylidene)-4-piperidone or EF24 (Example 1). EF24 was first created in Emory University (Atlanta, Ga.) [Adams et al., 2005; Kasinski et al., 2008; Selvendiran et al., 2007; Subramaniam et al., 2008; Sun et al., 2006], and it has been shown to inhibit IkappaB kinase [Kasinski et al., 2008]. It induces apoptosis in A549 lung cancer cells; the apoptosis was synergistically increased by inhibition of p38 MAPK [Thomas et al., 2010]. Compared to EF24, CLEFMA appears to possess more potent anti-proliferative activity in H441 cells (FIG. 13a). The experimental data collected also demonstrates that CLEFMA is comparable to other clinical anticancer drugs in potency, such as doxorubicin, paclitexal and gemcitabine (data not shown). In a parallel investigation, the molecular basis of CELFMA's anti-proliferative action was investigated, and evidence that CLEFMA induces autophagy in H441 cells was found (Example 1). For the cells with deficient apoptotic machinery, alternative modes of cell death, including macroautophagy, assume importance [Bergmann, 2007]. Like the majority of lung cancer cells, H441 cells carry k-Ras mutation that confers anti-apoptotic advantage to the cells [Meylen et al., 2009].

In order to enable intravenous administration of poorly water soluble CLEFMA, an approach where CLEFMA was first solubilized in aqueous HPβCD solution as 1:1 IC was employed, and the IC was then encapsulated within the liposomes. Using EF24 as a model drug, the inventors recently reported standardization of encapsulation parameters and stability of resultant preparation in an accompanying report [Agashe et al., 2010]. The strategy was successful for CLEFMA also, because even after several days of storage at 4° C., there was no sign of liposome destabilization. The instability of liposomes would have resulted in the leakage of co-encapsulated glutathione, culminating in a significant drop in Tc-99m labeling efficiency. No decrease in efficiency of Tc-99m-labeling was found over the storage period of >20 days.

An intravenous parenteral preparation of CLEFMA could also be accomplished simply by the use of aqueous HPβCD-CLEFMA IC. It was chosen to form liposomes of IC because of several reasons, most importantly the propensity of HPβCD IC towards rapid renal clearance. In a separate work in a rat model, renal clearance of IC accounting for >50% elimination was observed within the first 10 min after administration (data not shown). Liposomes on the other hand are eliminated through a relatively slower reticuloendothelial route—a metabolic pathway that can be delayed by altering the liposome composition [Awasthi et al., 2004]. Potentially, CLEFMA liposomes could be modified to circulate in blood and make drugs bioavailable over a prolonged time without affecting the efficacy of the encapsulated drug. The inventors have previously shown the utility of poly(ethylene glycol) or PEG for prolonging circulation as well as reducing its toxicity [Awasthi et al., 2004; Awasthi et al., 2007]. Once encapsulated, the innate pharmacokinetic and metabolic profiles of the liposomes take precedence over that of the drug. Other beneficial features of liposomes are the generic liposome characteristics, such as biodegradability, preferential EPR-dependent accumulation in tumor and potential for targeting.

Although not targeted for delivery, CLEFMA appears to possess selective anti-proliferative activity in cancer cells. Histopatholgical examination of liver lung and kidney showed no toxicities in these tissues. This observation was in agreement with the in vitro observation that CLEFMA was not anti-proliferative to the normal lung fibroblasts. While the fundamental basis of this selectivity towards cancer cells is not clear, CLEFMA has been found to be equally potent in controlling proliferation of other cancer cells, such as pancreatic (MiaPaCa-2 and Panc-1), colon (HCT-116) and prostate (PC-3) cancer cells (Example 1). In this Example, it was found that liposome-encapsulated CLEFMA not only retained the potency of free CLEFMA, but was also effective in curtailing the growth of H441 tumor when administered in rats carrying xenografts of human lung adenocarcinoma H441 cells (FIG. 14). In 2/6 treated animals, there was complete remission of tumor. These observations were confirmed by PET imaging of FDG accumulation in tumor. Relative to untreated tumors in control rats, the reduced FDG uptake in tumors of CLEFMA liposome-treated rats is a molecular indicator of suppressed tumor growth.

An attractive aspect of CLEFMA liposomes is the ability to radiolabel them with an imageable probe without affecting the availability, kinetics and efficacy of the encapsulated drug [Agashe et al., 2010; Awasthi et al., 2003; Awasthi et al., 2004; Awasthi et al., 1998; Awasthi et al., 2002; Awasthi et al., 2007]. In a Critical Path Initiative, the FDA and NCl have emphasized the role of imaging in hastening drug development [Altar, 2008; Woodcock et al., 2008]. Imaging has the ability to provide drug accumulation profile in a non-invasive and longitudinal fashion under physiologic conditions. Indeed, this capability of CLEFMA liposomes was shown by imaging their accumulation in various organs and tumor (FIG. 15). From the biodistribution studies, it was clear that most of the CLEFMA-liposomes accumulated in liver. In SPECT images, the spleen also appears to carry large amount of administered dose. As a member of reticuloendothelial system, splenic and hepatic macrophages are specialized for particle uptake. These observations are in line with the inventors' previous observations in experiments involving liposomes without a PEG-linked lipid in the bilayer [Awasthi et al., 2004]. The circulation persistence of these liposomes was also relatively short because of the absence of PEG-lipid.

In summary, this Example demonstrates that CLEFMA can be encapsulated inside the liposomes using aqueous HPβCD as a solubilizing agent. The resultant liposomes appear to be stable upon storage under refrigerated conditions. In vitro and in vivo efficacy results of this study, coupled with the absence of any apparent toxicity, demonstrate the potential of CLEFMA as an effective drug against lung cancer. The presented liposome formulation not only carries an anticancer drug, but can also be monitored by imaging using non-invasive SPECT. The potency of CLEFMA liposomes may be enhanced further by incorporating poly(ethylene glycol)-linked phospholipid in the liposome formulation. The potent efficacy, histopathologic non-toxicity, and selective anti-proliferative action in cancer cells are beneficial outcomes of CLEFMA therapy.

TABLE 4

Treatment schedule of xenograft tumor in nude rats.

| Procedure | 1 to 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|
| Tumor implant | Implant | | | | | | | | | | | | | | | | | | | | | | |
| Treatment | T | | | | T | | T | | | | T | | | | T | | | | T | | | | |
| PET imaging | | | | | | | | | | | | | | | | | | | | | | PET | |
| Biodistribution | | | | | | | | | | | | | | | | | | | | | | | BIO |

The tumor was implanted on day 1 and allowed to grow for 15 days. Intravenous treatment (T) with CLEFMA liposomes was started on day 15 and continued up to day 33. PET imaging of FDG accumulation was carried out on day 36, followed next day by the biodistribution study.

EXAMPLE 3

Despite a growing understanding about the molecular basis of oncogenesis, the prevention and cure of cancer remains a challenge. Chemotherapeutic drugs are the mainstay in managing patients diagnosed with any form of cancer. The emergent chemoresistance, morbid toxicities and overall inefficacy of current drug portfolios in many cancers necessitate the development of new drugs with novel mechanisms of action and therapeutic selectivity in cancer cells. Taking a cue from the recent findings that curcumin has a tumor-suppressive activity in a variety of cancers [Lev-Ari et al., 2006; Subramaniam et al., 2008], a structure-activity relationship on several synthetic diphenyldihaloketone analogs was performed [Subramaniam et al., 2008; Lagisetty et al., 2009]. As a chemical class, such compounds belong to chalcones, in which two aromatic rings flank a three-carbon enone fragment on either side. Several synthetic molecules, purportedly belonging to this class, have recently been synthesized as antiproliferative and anti-infective agents [Adams et al., 2004; Du et al., 2006; Modzelewska et al., 2006; Robinson et al., 2005]. The lead compound is 3,5-Bis(2-fluorobenzylidene)-4-piperidone (also known as EF24), which was first reported by Adams, et al. [Adams et al., 2004] and possesses potent antiproliferative activity against a number of cancer cell lines, such as colon, [Subramaniam et al., 2008] breast [Sun et al., 2006] and ovarian cancer cell lines [Selvendiran et al., 2007]. The exact mechanism of action of EF24 is unclear, but it appears to suppress cancer cell proliferation and angiogenesis by downregulating various cancer-promoting genes, such as COX-2, IL-8 and VEGF [Subramaniam et al., 2008]. EF24 has also been found to induce G2/M cell cycle arrest and apoptosis in cisplatin-resistant human cancer cells [Selvendiran et al., 2007], and a recent study suggests that EF24 suppresses NF-kB signaling by directly inhibiting I-kB kinase [Kasinski et al., 2008]. Chemically, it has been proposed that conjugated enones inhibit glutathione-S-transferase, which enhances the cytotoxicity of these compounds [O'Dwyer et al., 1994]. The enones permit a Michael addition of intracellular thiol compounds, such as glutathione, to the olefinic double bond. The addition products are capable of releasing the conjugated drug based on a reversible equilibrium between the conjugate and the free drug [Adams et al., 2005; Costi et al., 2004; Pati et al., 2008; Sun et al., 2009].

It is now well established that oxidative stress is involved in the initiation and progression of many diseases and disorders, including cancer and inflammation [Fang, et al., 2009; Behrend et al., 2003]. The constitutively enhanced levels of cellular oxidative stress in cancer cells and their dependence on mitogenic and anti-apoptotic reactive oxygen species (ROS) enable the maintenance of a cancer phenotype [Gibellini et al., 2010], intuitively suggesting that further elevation of ROS will promote cancer growth. However, certain agents generating ROS preferentially kill cancer cells while sparing the normal cells from significant toxicity, as demonstrated in several in vitro and in vivo models [Wondrak, 2009]. For instance, 2-methoxyestradiol is toxic to human leukemia cells but does not cause cytotoxicity in normal lymphocytes [20]. Although cancer cells are characterized as oxidatively stressed [Chen et al., 2008; Trachootham et al., 2009], they have a unique ability of maintaining ROS at levels conducive to growth and proliferation. However, a further increase in ROS can promote cell death secondary to the widespread oxidative damage of macromolecules. Therefore, modulating oxidative stress may be one of the triggering mechanisms of cell death, especially in cancer and transformed cells [Chen et al., 2008; Scherz-Shouval et al., 2007]. The disruption of ROS homeostasis by exogenous drugs may be a selective way of killing cancer cells without causing significant toxicity to the normal cells.

Figure 17:
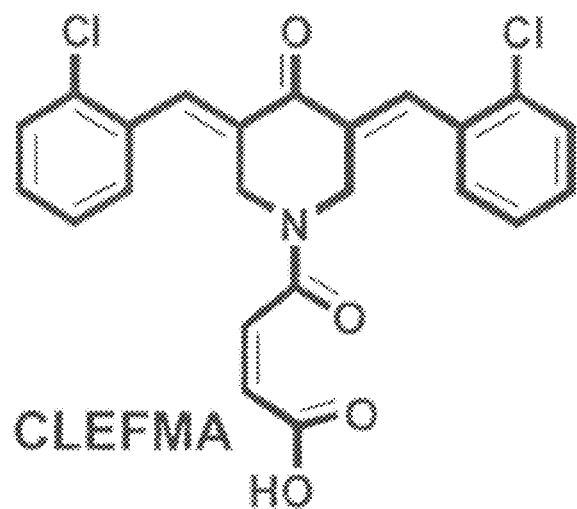
FIG. 17 contains the molecular structure of CLEFMA. The synthesis of CLEFMA is described in Example 1.

In the previous Examples, the inventors reported the synthesis of a modified derivative of EF24 by replacing fluorine atoms with chlorine and adding a maleic acid moiety at the piperidinyl nitrogen (FIG. 17). The compound 4-[3,5-bis(2-chlorobenzylidene-4-oxo-piperidine-1-yl)-4-oxo-2-butenoic acid] is referred to as CLEFMA, signifying its structural peculiarities (Example 1). As shown in Example 1, CLEFMA potently inhibited the proliferation of H441, MiPaCa-2, Panc-1 and PC-3 cancer cells, and evidence was found that CLEFMA induced autophagic cell death in H441 lung adenocarcinoma cells. This is important because the lung cancers are typified by the downregulation of the apoptotic pathway resulting in an inherent chemoresistance. Specifically, pro-oncogenic mutations in the tumor suppressor p53 are found in ~50% of non-small cell lung carcinomas [Herbst et al., 2008], and K-Ras is mutated in approximately 30% of lung adenocarcinomas [Huncharek et al., 1999]. Both the PTEN-PI3K-AKT-mTOR and the Ras-RAF-MEK-ERK pathways bear mutations conferring anti-apoptotic and survival advantages in lung cancer cells [Furuta et al., 2004; Meylan et al., 2009]. Other molecular prognostic markers, such as p53, bcl-2, p21WAF1 and their associated pathways, are also defective in lung cancer [Lee et al., 1995; Huang et al., 2007; Niklinski et al., 2001]. The altered expression of these apoptosis regulators renders many apoptosis-inducing drugs ineffective in lung cancer. Therefore, there is considerable merit in designing drugs to induce the alternate modes of cell death.

In this Example, a biochemical basis of CLEFMA-induced cell death in the H441 cell model is revealed. For preliminary work, H441 cells were chosen because they originate from a typical lung adenocarcinoma and carry p53 and K-Ras mutations to gain a survival advantage [Meylan et al., 2009]. Due to the complexity of the genetic pathways and their cross talk, a comprehensive screen of transcript profiles is useful to address the changes associated with drug action. The present study uses microarray analysis to study gene expression in a model of H441 cells in response to CLEFMA. These data indicate that the expression of genes involved in oxidative stress pathways is altered by CLEFMA treatment in H441 cells. The microarray data were then supported by functional assays demonstrating increased oxidative stress in H441 cells resulting in cell death.

Material and Methods for Example 3

Cell culture: The human lung adenocarcinoma cell line NCl-H441 (ATCC Number: HTB-174) and normal lung fibroblasts CCL-151 were obtained from American Type Culture Collection (Manassas, Va.). H441 cells were maintained at 37° C. with 5% $CO_2$ in McCoy's 5A Medium (Invitrogen, Carlsbad, Calif.) supplemented with 5% heat-inactivated fetal bovine serum (FBS). All media contained gentamicin at 50 µg/ml (GIBCO Laboratories, Grand Island, N.Y.).

Cell proliferation assay: CLEFMA was synthesized and analyzed for purity by the methods detailed elsewhere [24]. Doxorubicin (DOX, GBiosciences, Maryland Heights, Mo.), Paclitexal (PAX, EMD Chemicals, Gibbstown, N.J.), Curcumin (CUR, Sigma, St. Louis, Mo.) and Gemcitabine (GMCB, Acros Organics, Morris Plains, N.J.) were obtained from commercial sources. For cell proliferation assays, the cells were seeded in 96-well, flat-bottom tissue culture plates at a density of 5,000 cells per well. The cells were allowed to adhere and grow overnight, followed by their treatment with drugs (0-20 µM). All drugs were added as solutions in dimethylsulfoxide (DMSO) filtered through 0.2-µm nylon filters; control wells received identical amounts of DMSO without any drugs. The inhibition of cell proliferation was determined after 24-48 h by measuring the decrease in hexosaminidase activity as described by Landegren [Landegren, 1984]; para-nitrophenol-N-acetyl-beta-D-glucosaminide was used as a substrate for the hexosaminidase enzyme. To assess the effect of antioxidants, the cells were simultaneously treated with catalase (CAT, 1000 U), superoxide dismutase (SOD, 500 U) and N-acetylcysteine (NAC, 1 mM). A non-toxic concentration of CAT (Worthington, N.J.), SOD (Sigma, St. Louis, Mo.) and NAC (Enzo Life Sciences, Plymouth Meeting, Pa.) was established in H441 cells prior to these experiments.

RNA Extraction and microarray sample processing: H441 cells were seeded in E-well tissue culture plates at a density of $1\times10^6$ cells per well. The cells were allowed to attach and grow overnight and then treated with CLEFMA (n=5) at 1 µM in culture medium supplemented with 5% FBS. The DMSO concentration was maintained at 0.1% per well. Control wells (n=5) received equivalent volumes of DMSO without any test compound. The cells were kept in the treatment medium for 12 hours, after which the cells were washed twice with ice-cold Dulbecco's phosphate buffered saline (PBS). The total RNA was extracted using the RNAeasy kit (Qiagen, CA) as per the manufacturer's instructions. The quality of RNA was ascertained by the Nanodrop 2000 spectrophotometer (Nano-Drop products, Wilmington, Del.).

The expression of >48,000 genes were compared using Illumina Human WG-6 v3 arrays. Hybridization to Illumina microarrays was performed at the Oklahoma Medical Research Foundation (Oklahoma City, USA). RNA (250 ng) from each sample was labeled using the Illumina Total Prep RNA Amplification Kit following the manufacturer's directions (Ambion, Austin, Tex.). Briefly, cDNA was reverse transcribed from RNA after priming with T7-oligo-dT, and cRNA was synthesized from the T7 promoter while incorporating biotinylated UTP. The cRNA was then hybridized overnight to Illumina BeadChips, and the microarray chips were washed with high stringency and labeled with streptavidin-Cy3 (Amersham Biosciences; Piscataway, N.J.) prior to scanning on an Illumina BeadArray Reader.

Microarray Data Analysis: The Illumina WG-6_v3 array data for each experimental condition were exported from the BeadStudio Software for further analysis. The data were normalized as described previously [Dozmorov et al., 2004; Dozmorov et al., 2009] using the variability of low-expressing genes as a reference point. In order to find genes expressed above the level of technical noise, a frequency histogram of raw expression values was examined for each array. The histogram yielded a right-skewed unimodal distribution curve with a mode of approximately 75. A normal distribution curve representing the variability of the data around zero was then fitted around the mode, mirroring the Gaussian profile of the left part of the histogram. Its parameters were then defined (mean and standard deviation (SD)) and the data were normalized to the standard deviation of the noise after subtraction of the mean. The arrays were $Log_{10}$-transformed and adjusted by robust linear regression under the assumption that the expression of most genes does not change. The data were then filtered to remove genes with an expression value less than 3.0. This is equivalent to setting a threshold at 3 SD above the noise level. The genes that expressed below the noise level under all experimental conditions (approximately 1,600) were excluded from consideration, as their expression could not be reliably assessed. Full microarray data were deposited in the Gene Expression Omnibus (GEO, GSE23420) and are accessible on the GEO web site.

To identify differentially expressed genes between two experimental groups, the associative analysis as described elsewhere [Dozmorov et al., 2009] was used. Briefly, a reference group of genes expressed above background with low variability of expression in pooled microarray datasets was identified by an F-test. It was assumed that because most genes do not change expression in any experiment, the variability in expression among this group was due to random, technical factors alone. For the genes with statistically significant variability above the random, the variations were assumed to have biological reasons. An associative t-test was applied to investigate if a given gene belongs to a certain group. To identify an evaluable number of differentially expressed genes, a stringent criterion was applied: only the genes that expressed below the noise level in one group and greater than 5 SD above the noise level in another group were selected for further analysis. For the genes that were expressed above noise level in both conditions, the genes that showed greater than a 1.5-fold difference in their expression level and expressed greater than 10 SD above the noise level in at least one condition were also selected. These genes were considered to be the "beacons" that pointed to the affected pathways or gene networks.

To classify each group of genes by their ontological properties, the Database for Annotation, Visualization and Integrated Discovery (DAVID) [Dennis et al., 2003] was used. The Gene Functional Classification tool in DAVID builds clusters of genes with significantly similar ontologies, as tested against the whole list of genes in the ILLUMINA® WG-6 (v3) array (San Diego, Calif.). A medium stringency was used to yield a comprehensive set of ontological groups and to group the genes with similar functions. Increasing or decreasing the stringency resulted in the identification of fewer or more groups of genes with similar functions but did not provide any additional information.

The lists of genes from individual clusters were submitted to Ingenuity Pathway Analysis (IPA; INGENUITY® Systems, Redwood City, Calif., http://www.ingenuity.com); Ingenuity maps gene IDs to its database and performs statistical computing to identify the most significant ontologies, canonical pathways, and networks over-represented in a given gene list, as compared with the whole list of genes in the Illumina WG-6_v3 array. By default, $p<0.05$ was used in all calculations. Gene lists from each group were analyzed for over-represented general functions, canonical pathways, and the networks that could be assembled from them.

Reactive oxygen species (ROS) assay: The CLEFMA-induced generation of ROS in H441 and CCL-151 cells was measured using the OxiSelect assay kit (Cell Biolabs, Inc., San Diego, Calif.). Briefly, the cells were cultured in 96-well plates, and the cell-permeable fluorogenic probe 2',7'-dichlorodihydrofluorescin diacetate (DCFH-DA) was added to the wells and the plate was incubated for 30-60 min. The wells were washed thrice with PBS and treated with CLEFMA in culture medium for 24 and 48 h. After the incubation period, the medium was removed and the cells were gently washed 2-3 times with PBS, and the fluorescence, indicating ROS activity, was measured at 480 nm/530 nm (excitation/emission wavelengths) using the Cytoflour 2300 (Millipore, Billerica, Mass.).

MitoSOX Red mitochondrial superoxide imaging: Cells were grown to 70% confluency in 24-well tissue culture plates and treated with CLEFMA (0-20 µM) for 12-48 h; treatment with hydrogen peroxide ($H_2O_2$, 10 µM) served as a positive control. At the end of the incubation period, both the non-adherent and adherent cells were incubated with 5 µM MitoSOX Red solution (Invitrogen, Carlsbad, Calif.) for 30 min at 37° C. For flow cytometric analysis, the MitoSOX-loaded cells were trypsinized and collected in HBSS (with Ca/Mg) containing 1% BSA and suspended at a density of $1-2\times10^7$ cells/ml. Approximately 5-10 million cells were aliquoted into a binding buffer and run through an automated dual-laser-excited FACS Calibur (Flow and Imaging Core Facility, OUHSC, Oklahoma City) measuring at 488 nm excitation wavelength. The data were collected at the FSC, FL2 and FL3 channels for at least 10,000 events, and the histogram and dot-plot charts were obtained and analyzed using Summit V4.3 software (Dako Colorado Inc, Carpinteria, Calif.). For microscopy, the MitoSOX-loaded cells were counterstained with 1 µg/ml Hoechst 33342 dye (Molecular Probes, Carlsbad, Calif.). Digitized microscopic images were acquired using an inverted epifluorescent microscope (Nikon TE2000-E) equipped with a 40× Plan Fluor NA 0.60 dry objective and using a 568 nm band-pass filter specifications for MitoSOX and 360/40 for Hoechst 33342.

Glutathione-to-glutathione disulfide (GSH/GSSG) assay: In order to assess the effect of CLEFMA on cellular GSH levels, a kit from Oxford Biomedical Research (Oxford, Mich.) was used and followed a modification of the method reported elsewhere (NCL Method GTA-3, Nanotechnology Characterization Lab, Frederick, Md.). H441 were seeded in a 12-well plate (1 million cells/well) and treated with CLEFMA for 12 and 24 h. The medium was removed and the cell layer was washed twice with ice-cold PBS. After adding 100 µl of ice-cold 5% m-phosphoric acid, the cells were scraped into a microfuge tube and centrifuged at 1000×g at 4° C. for 10 min. The supernatant was removed to a fresh tube for the GSSG and GSH assays. For the GSSG determination, approximately 30 µl supernatant was mixed with 20 µl thiol scavenger and 130 µl ice-cold assay buffer, and for the GSH assay, approximately 5 µl of the supernatant was diluted in 180 µl with ice-cold assay buffer. The diluted GSSG and GSH samples (50 µl) were reacted with 5,5'-dithiobis-2-nitrobenzoic acid (DTNB) solution in the presence of glutathione reductase and NADPH. The plate was read in a microplate reader at 405-414 nm at 0 and 10 min after DTNB was added. The GSH and GSSG concentrations were determined following a linear regression analysis and normalized to total protein. The ratio (GSH−2GSSG)/GSSG was calculated and expressed as the percent of untreated control cells.

Nuclear extract and immunoblotting: Nuclear extract was prepared using a kit from Active Motif (Carlsbad, Calif.) following the manufacturer's instructions. Briefly, H441 cells were allowed to grow for 24 h in 6-well plates before treatment with CLEFMA. After 12 or 24 h, the cells were scraped into ice-cold PBS and centrifuged at 300×g for 5 min to obtain a pellet. The pelleted cells was resuspended in a hypotonic buffer (20 mM HEPES, pH 7.5, 5 mM NaF, 0.1 mM EDTA, and 0.01 mM Sodium molybdate) and allowed to swell for 15 min on ice. The cells were lysed by adding 50 µl 10% Nonidet P-40 and centrifuged for 30 sec to separate the cytoplasmic and nuclear fractions. The nuclear fraction was extracted after 30 min in an ice-cold complete lysis buffer obtained with the kit. The nuclear extract was separated by centrifugation for 10 min at 14,000×g at 4° C. To immunoblot nuclear factor-erythroid 2-related factor 2 (Nrf2), the nuclear protein (10 µg) was separated on a 4/20% SDS-PAGE gel, transferred onto nitrocellulose membrane and probed with rabbit anti-phospho-Nrf2 antibody and HRP-conjugated goat anti-rabbit IgG antibody. The chemiluminescence signal was developed by Pierce SuperSignal West Femto reagent (Thermo Scientific, Rockford, Ill.). Equal protein loading was confirmed by stripping the blot and re-probing it with anti-actin antibody. Nrf2 antibodies were obtained from Epitomics (Burlingame, Calif.), and the anti-actin antibody was purchased from Sigma.

Data analysis: The results, expressed as the mean±standard error of the mean, are either representative or the average of at least three independent experiments.

Results of Example 3

Figure 18:
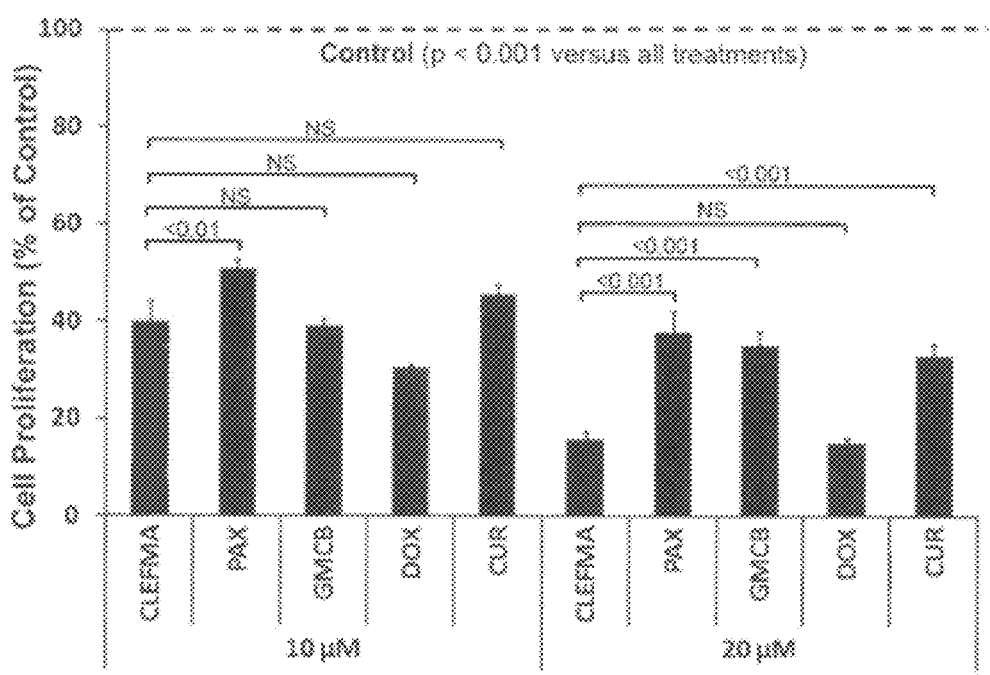
FIG. 18 illustrates that the antiproliferative action of CLEFMA in H441 cells (5,000 cells/well) is comparable to that exhibited by other anticancer drugs. The extent of cell proliferation after 48 h of treatment was assayed by measuring hexosaminidase activity. PAX=Paclitexal, GMCB=Gemcitabine, DOX=Doxorubicin, and CUR=Curcumin.

The antiproliferative action of CLEFMA is comparable to that of other major anticancer drugs: The antiproliferative capability of CLEFMA was compared to anticancer drugs that are commonly used for the treatment of lung cancer, such as paclitexal (PAX), gemcitabine (GMCB), and doxorubicin (DOX); CLEFMA was also compared to curcumin (CUR), the natural congener of the curcuminoid CLEFMA. H441 cells were treated with 10 and 20 µM of various drugs; at both concentrations, CLEFMA appeared to exhibit antiproliferative activity comparable to that shown by these drugs (FIG. 18).

CLEFMA upregulates genes related to cellular oxido-reductive status: 95 genes that were stably upregulated (>1.5-fold) and 59 genes that were downregulated were identified in cells treated with CLEFMA. The complete lists of genes are provided in Tables 5-7. The main ontology over-represented in 95 upregulated genes was oxidation/reduction, containing 23 genes (Table 5). These genes were parts of more specific ontologies, namely, aldo-keto reductase, NADP or NADPH binding, and glutathione metabolism. It was observed that nearly complete sets of Phase I and II enzymes were upregulated by CLEFMA. The Phase I enzymes included several members of the aldo-keto reductase family: AKR1B1, AKR1B10, and AKR1C2-4. Phase II enzymes included glutathione peroxidase (GPX2), glutathione reductase (GSR), glutamate cysteine ligase (GCLC, GCLM), glutathione S-transferase (GSTA4), NAD(P)H:quinine oxidoreductase 1 (NQO1), and UDP glucoronyl transferase (UGDH). Other known antioxidants were also upregulated either to a lesser extent or not stably enough to pass the strict criteria of associative analysis. These enzymes included superoxide dismutase (SOD1, 1.3-fold increase), heme oxygenase 1 (HMOX1, 5.3-fold), and sulfotransferases (SULTA1, 3.8-fold and SULTA2, 8.5-fold) [Nguyen et al., 2003]. An increase in glyceraldehyde-3-phosphate dehydrogenase (GAPDH, 1.3-fold increase), the redox-sensitive activity of which indirectly leads to increased NADPH production [Raiser et al., 2007], as also observed.

Figure 19:
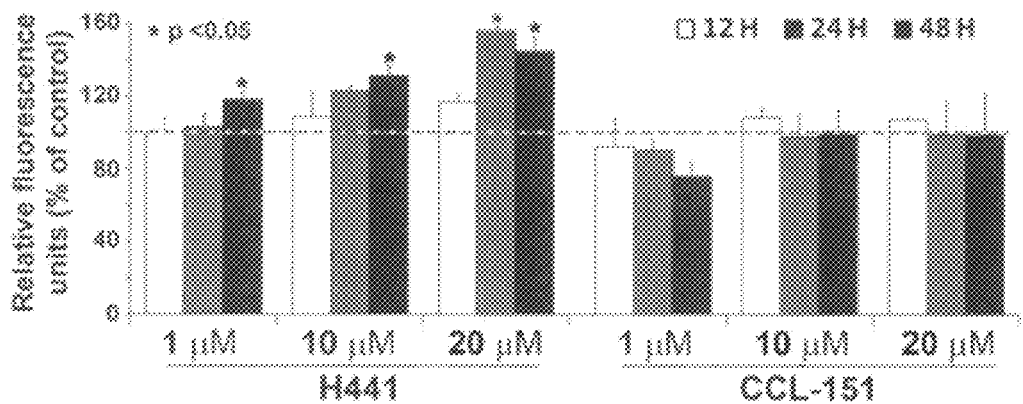
FIG. 19 illustrates that treatment with CLEFMA induces the generation of reactive oxygen species (ROS) in H441 cells but not in CCL-151 normal lung fibroblasts. ROS generation was estimated based on the fluorescence intensity of the cell-permeable, fluorogenic 2',7'-dichlorodihydrofluorescin diacetate.
Figure 20:
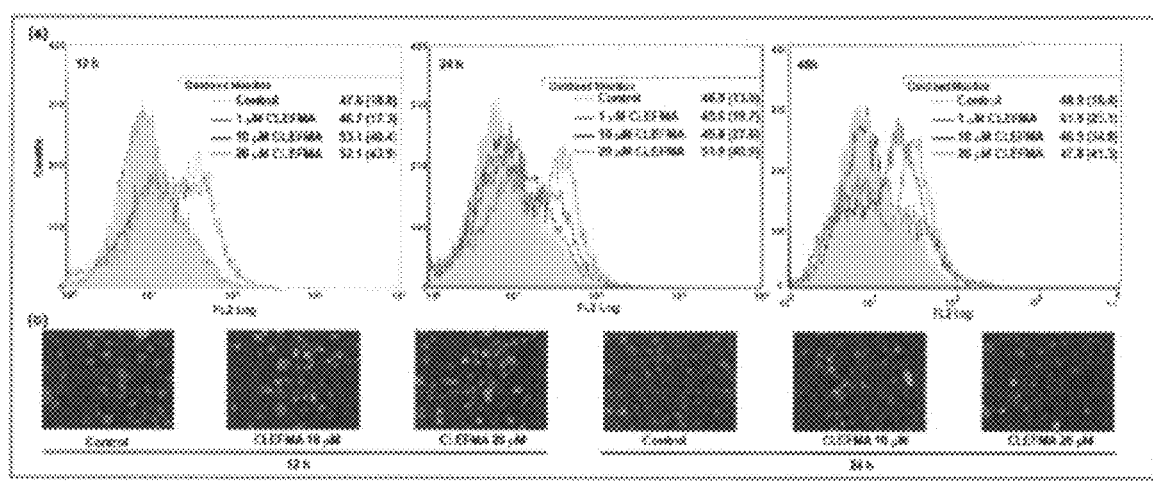
FIG. 20 illustrates that CLEFMA-induced ROS generation is mitochondrial in origin. A mitochondria-specific indicator of ROS (MitoSOX) was loaded into H441 cells for (a) flow cytometry and (b) inverted microscopy. In both assays, there was a clear time- and dose-dependent increase in red fluorescence in CLEFMA-treated H441 cells.

ROS production is specifically induced in cancer cells: The inventors hypothesized that the upregulation of the oxido-reductive pathway was due to the enhanced production of ROS by H441 cells in response to CLEFMA. As shown in FIG. 19, CLEFMA treatment generated ROS in a dose- and time-dependent fashion. Importantly, CLEFMA did not increase ROS production in normal lung fibroblasts (FIG. 19). Thus, it was further tested whether CLEFMA-induced ROS was generated in mitochondria using MitoSOX, a mitochondria-selective fluorescent reporter of ROS. Both flow cytometric data as well as inverted micrographs of MitoSOX-loaded cells confirmed the mitochondrial origin of CLEFMA-generated ROS in H441 cells; a time- and dose dependent increase in mitochondrial ROS production was observed (FIG. 20).

Figure 21:
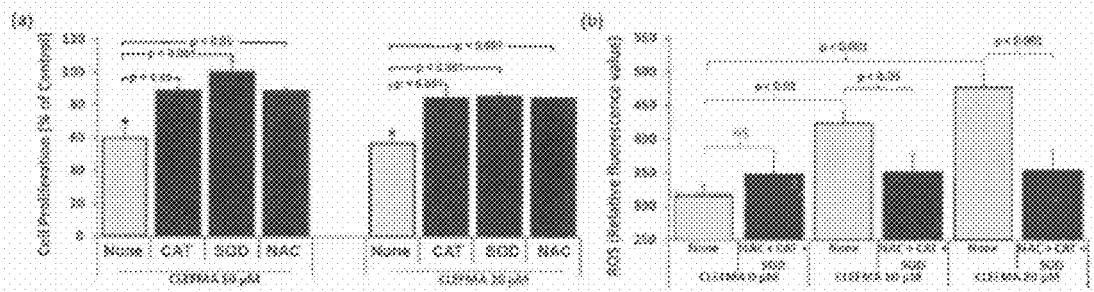
FIG. 21 illustrates that ROS scavengers rescue H441 cells from CLEFMA-induced cell death. (a) The simultaneous treatment with CLEFMA and various ROS scavengers rescues H441 cells from cell death. Cells were treated with CLEFMA (10 and 20 µM) in the presence of catalase (CAT, 1000 Units), superoxide dismutase (SOD, 200 Units), and N-acetylcysteine (NAC, 1 mM). Cell proliferation was measured by hexoaminidase assay. (b) The ROS scavengers (CAT 500 U, SOD 100 U, and NAC 0.5 mM) also inhibit ROS generation in H441 cells. Asterisk (*) denotes p<0.001 compared to control (100%).

Antioxidant supplementation rescues H441 cells from CLEFMA-induced cell death: Although the upregulation of several antioxidant and detoxifying molecules was observed in response to CLEFMA, their amounts may be insufficient to effectively combat excessive ROS production. The inventors hypothesized that antioxidant supplementation, when co-administered with CLEFMA, would counteract its antiproliferative effect. Together with CLEFMA, non-toxic amounts of catalase (CAT), superoxide dismutase (SOD) and N-acetylcysteine (NAC) were added to H441 cells. Each of these supplements was able to partially rescue CLEFMA-induced cytotoxicity (FIG. 21a), presumably by counteracting $H_2O_2$ and $O_2$ ROS production. A simultaneous reduction in CLEFMA-induced ROS generation was also observed in the presence of these free radical scavengers.

CLEFMA depletes glutathione in H441 cells: The Ingenuity Pathway Analysis (IPA) of up- and downregulated genes separately confirmed the aforementioned findings and identified a close interplay among them. The IPA identified two main functional annotations over-represented by up- and downregulated genes (Table 5), namely, glutathione metabolism and cell death.

Figure 22:
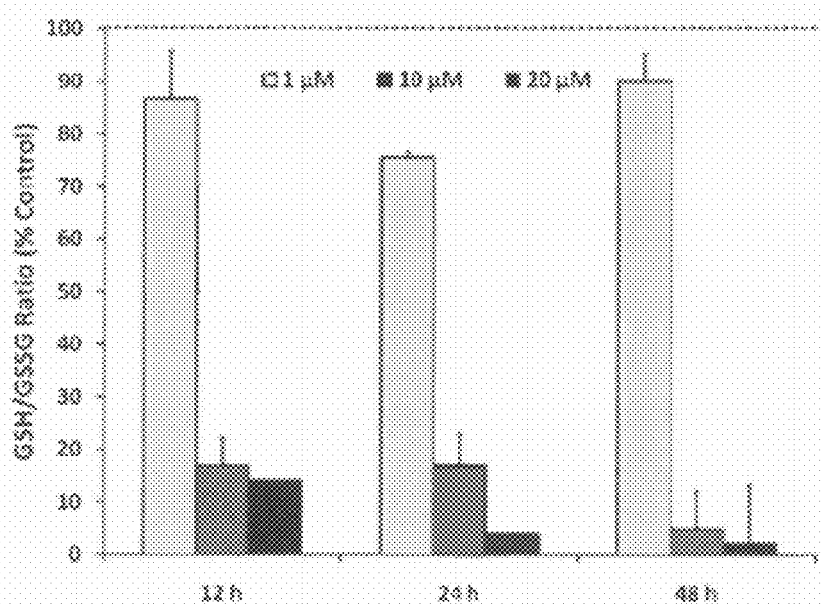
FIG. 22 illustrates that CLEFMA reduces the GSH/GSSG ratio in H441 cells. The GSH and GSSG levels were assayed as described in Materials and Methods of Example 3.

Free radicals are reduced by glutathione (GSH) in the presence of selenium-dependent GSH peroxidase, which is highlighted by the induction of glutathione peroxidase 2 (GPX2). In this process, GSH is oxidized to GSSG, and the enzyme that reverts GSSG back to reduced GSH, glutathione reductase (GSR), is inducible by oxidative stress; GSR is highly upregulated in the presence of CLEFMA. The ratio of reduced glutathione to oxidized glutathione within cells is often used as a measure of cellular toxicity [Pastore et al., 2001]. In order to support the gene expression data, the GSH/GSSG ratio was analyzed in H441 cells treated with CLEFMA, and a strong dose-dependent reduction of the GSH/GSSG ratio upon CLEFMA treatment was identified (FIG. 22).

Figure 23:
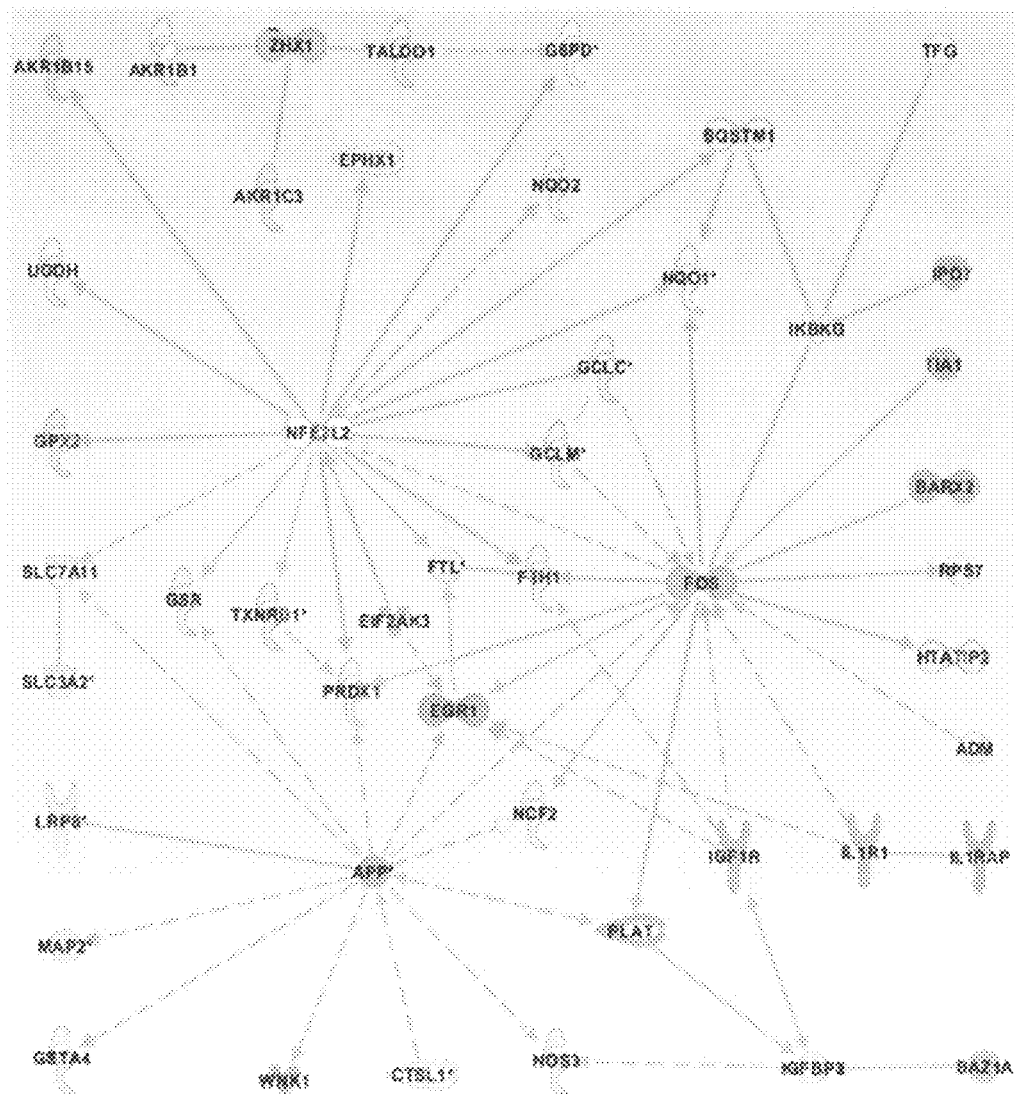
FIG. 23 illustrates that CLEFMA alters the expression of genes involved in oxido-reductive pathways. Red and green highlight up- and downregulated genes, respectively. The full microarray data have been deposited in the Gene Expression Omnibus (GEO, GSE23420) for access on the GEO web site.
Figure 24:
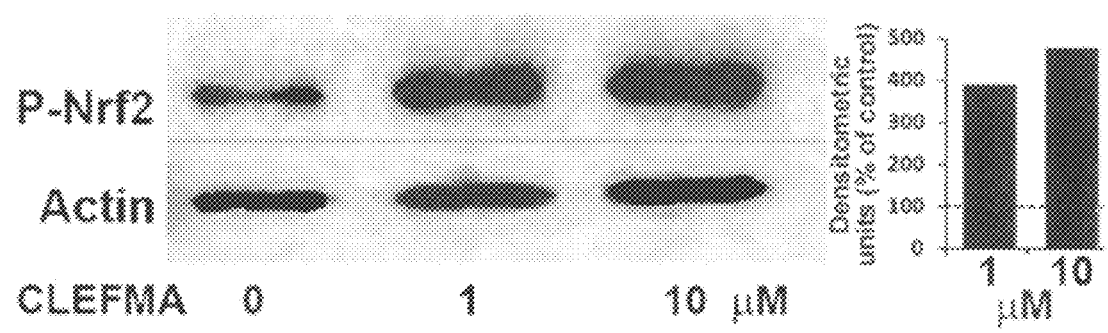
FIG. 24 illustrates that CLEFMA induces nuclear translocation of phosphorylated Nrf2 in H441 cells. A representative immunoblot is shown from two sets of experiments at multiple time points.

CLEFMA activates Nrf2: The canonical pathway analysis in H441 cells treated with CLEFMA identified an Nrf2-mediated oxidative stress response; Nrf2 is one of the main pathways in the cellular stress and injury category. Other pathways included glutathione metabolism, pyruvate and glycerolipid metabolism, and xenobiotic metabolism (Table 6). It was found that Nrf2 is highly expressed in this system; although its expression did not significantly change at the mRNA level, it appears to be a major regulator of genes affected by CLEFMA treatment. Network analysis identified Nrf2, also called NF2E2L, as a central player regulating the majority of oxidative stress-related genes (FIG. 23). Nrf2 is a well-known regulator of oxidative stress, and it was tested whether the protein was activated upon CLEFMA treatment. As shown in FIG. 24, CLEFMA treatment activated Nrf2 and caused its translocation into the nuclear fraction. It may be noted that Nrf2 translocation is dependent on its phosphorylation status for activation (FIG. 24).

Discussion of Example 3

An Nrf2-mediated oxidative stress response was identified as a major mechanism of cell death induced by CLEFMA in H441 lung cancer cells. CLEFMA was found to induce increased ROS production in cancer cells but not in normal cells. The activation of protective oxido-reductive mechanisms was insufficient to combat this overwhelming ROS production, leading to cell death. It is known that moderate oxidative stress can trigger apoptosis, whereas more intense stresses may cause necrosis [Lennon et al., 1991] via ATP depletion [Lelli et al., 1998] and/or the prevention of controlled apoptotic death [Lee et al., 1999].

The detoxification and metabolism of xenobiotics occurs in two phases: Phase I consists of functionalization and Phase II involves conjugation reactions. The activation of both Phase I and Phase II enzymes by CLEFMA treatment was identified. The oxidative Phase I reactions typically involve cytochrome P450 monooxygenase, NADPH, and oxygen. However, the members of the large cytochrome P450 family were either not expressed or did not change in their expression upon CLEFMA treatment. The engagement of oxido-reductive mechanisms explains the subtle antioxidant effect of CLEFMA in normal cells (FIG. 19). However, in cancer cells, the observed increase in ROS production (FIG. 19) appears to overcome these protective oxido-reductive mechanisms, resulting in cell death. Counterintuitively, the Phase I reactions may promote the conversion of a relatively non-toxic molecule into a toxic species (toxification). Several aldo-keto reductases (AKRs) that convert carbonyl groups to primary or secondary alcohols were identified. AKRs are soluble NAD(P)(H) oxidoreductases responsible for the turnover of a vast range of substrates, including drugs, carcinogens, and reactive carbonyl compounds. In CLEFMA-treated H441 cells, the upregulation of two aldo-reductases (AKR1B1 and AKR1B10) and three hydrosteroid dehydrogenases (AKR1C2-4) was identified. It appears that these enzymes introduce reactive groups in CLEFMA, a process that is responsible for ROS production.

The Phase II conjugation reactions are generally detoxifying in nature and involve reactions between the polar functional groups of Phase I metabolites and endogenous conjugating molecules, such as GSH. The GSH conjugation reactions are catalyzed mostly by glutathione-S-transferase (GST). GSH is an important cellular antioxidant, and severe oxidative stress depletes the level of intracellular glutathione. GST is synthesized from cysteine by glutamate cysteine ligase (GCL). These microarray data indicate that CLEFMA induces glutathione synthesis in H441 cells. Both catalytic as well as modifier subunits of the GCL heterodimer (GCLC and GCLM, respectively) [Yang et al., 2001; Yang, et al., 2001] were highly induced upon CLEFMA treatment. GSR reduces GSSG back to GSH at the expense of NADPH, forming a redox cycle. In cells undergoing oxidative stress, up to 10% of the glucose consumption may be directed to the pentose phosphate pathway for the production of NADPH needed for this reaction. In this system, the upregulation of pentose and glucoronate interconversion pathways was identified (Table 6). In addition, glucose-6-phosphate dehydrogenase (G6PD), whose main function is to produce NADPH, is highly expressed upon CLEFMA treatment. Similarly, CLEFMA induces the expression of glyceraldehyde 3-phosphate dehydrogenase (GADPH), which is known to increase NADPH production under oxidative stress conditions [Raiser et al., 2007]. These observations suggest that the CLEFMA-induced oxidative stress results in the rapid activation of cellular mechanisms responsible for GSH synthesis. It appears that the GSH-GSSG redox cycle is the primary response of H441 cells to CLEFMA-induced oxidative stress. Several members of the AKR family represent an alternative GSH-independent, NADPH-dependent route for the reductive elimination of CLEFMA, as in the case of 4-hydroxynonenal [Burczynski et al., 2001].

The two members of the NAD(P)H dehydrogenase (quinone) family, NQO1 (NAD(P)H dehydrogenase, quinone 1) and NQO2, were also highly induced in this system. NQO1 is a ubiquitous cytosolic flavoenzyme that catalyzes the two-electron reduction of various quinones, with NADH or NADPH as electron donors. The NQO1-mediated reduction mechanism is responsible for the cellular defense against various damaging quinones [Joseph et al., 2000]; however, some nontoxic quinones are reduced to free radical-generating and toxic semiquinones via one electron transfer by NQO1. For instance, NQO1 induces the semiquinone form of 3-lapachone, depleting the cell of NAD(P)H in the process and resulting in the generation of DNA-damaging hydroxyl radicals [Pink et al., 2000]. It has also been shown that NQO1 stabilizes p53, especially under oxidative stress [Asher et al., 2002].

Other Phase II xenobiotic-metabolizing enzymes that were upregulated in this system are mainly involved in driving a network of interconnected metabolic reactions that eliminate reactive species at the sites of origin. Such cellular antioxidants included GPX2, peroxiredoxin (PRDX1), and GSTA4. The upregulation of thioredoxin reductase 1 (TXNRD1) was also observed. Several other well-known Phase II enzymes that did not pass rigorous statistical criteria include SOD1, HMOX1 or HO-1, epoxide hydrolase (EPHX1), and sulfuredoxin 1 (SRNX1). HO-1 catalyzes the first, and rate-limiting, step in the catabolism of the pro-oxidant heme to carbon monoxide, biliverdin, and free iron. Importantly, biliverdin reductase B (BLVRB) was identified as a focus molecule in this system. HO-1 mRNA and protein expression are commonly upregulated following oxidative stress and cellular injury [Guo et al., 2001]. EPHX1 converts epoxides from the degradation of aromatic compounds to trans-dihydrodiols. SRNX1 catalyzes the reduction of the active site of peroxiredoxin, converting it to an active state. Interestingly, PRDX1 was highly upregulated by CLEFMA treatment. This observed interplay among these enzymes and detoxification systems is summarized in FIG. 25. However, as noted above, the activation of the oxidative stress response in H441 cells appears to be insufficient to overcome CLEFMA-induced ROS production. A significant decrease in the GSH/GSSG ratio (FIG. 22) indicates the failure of the GSH-GSSG cycle and other detoxification systems.

The conjugates and their metabolites can be excreted from the cells in the third phase of their metabolism, with the anionic groups acting as affinity tags for a variety of MDR class membrane transporters [Homolya et al., 2003]. The upregulation of ABCB6 and ABCC3 transporters, which are members of the family of ATP-binding cassette transporters and catalyze the ATP-dependent transport of a large variety of hydrophobic anions [Konig et al., 1999], were observed.

Figure 25:
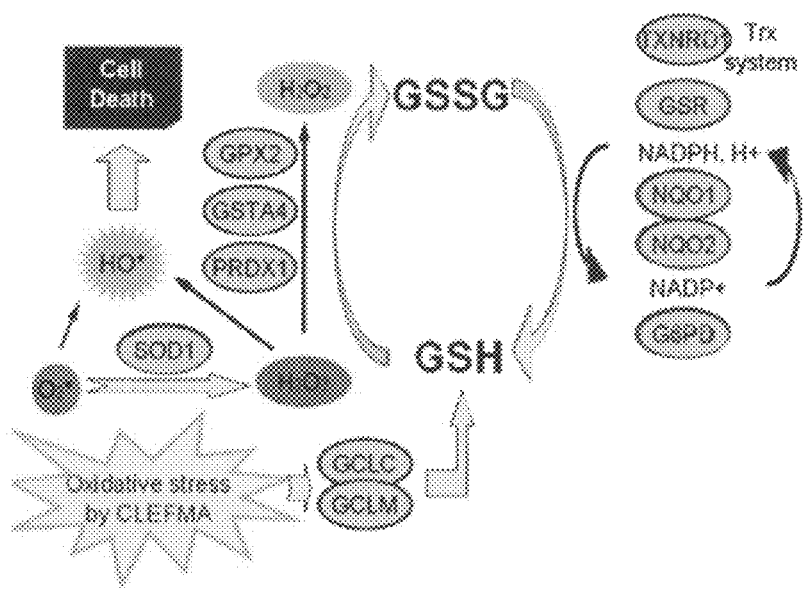
FIG. 25 illustrates a proposed mechanism of action of CLEFMA in H441 cells. G6PD—glucose-6-phosphate dehydrogenase; GCL—glutamate cysteine ligase; GCLC—GCL catalytic subunit; GCLM—GCL modifier subunit; GPX2—glutathione peroxidase 2; GSH—glutathione; GSR—glutathione reductase; GSSG—disulfide-oxidized form of glutathione; GSTA4—glutathione S-transferase; NQO1/2—NAD(P)H dehydrogenase, quinone 1/2; PRDX1—peroxiredoxin; SOD1—superoxide dismutase; TXNRD1—thioredoxin reductase.

The majority of the Phase I and II genes identified in this system were found to be regulated by the Nrf2 transcription regulator. Nrf2 binds to the antioxidant response elements (ARE) within the promoter region of these enzymes and activates their transcription [Jaiswal, 2004]. Inactive Nrf2 is retained in the cytoplasm by association with Kelch-like ECH-associated protein 1, but under oxidative stress, Nrf2 is phosphorylated and translocates to the nucleus. Once in the nucleus, Nrf2 heterodimerizes with a small musculo-aponeurotic fibrosarcoma (MAF) protein, binds to AREs [Itoh et al., 1997; Jaiswal, 2000], and transactivates detoxifying and antioxidant enzymes. The immunoblot results unequivocally show that CLEFMA treatment induces Nrf2 phosphorylation and translocation into the nucleus (FIG. 24). It may be noted that most of the genes induced by CLEFMA share ARE sequences in their promoter region. These genes include GST, NQO1/NQO2 [Jaiswal, 2000; Rushmore, et al., 1990], GCLC and GCLM [Mulcahy et al., 1995], members of AKR family [Burczynski et al., 1999; Penning et al., 2007], and SRNX1 [Singh et al., 2009]. Besides Nrf2-mediated transcriptional activation, the levels of certain antioxidant enzymes may be regulated post-transcriptionally in a redox-sensitive manner. For example, the stability of both the GCLC and GCLM mRNAs is redox-regulated, and their half-lives could be doubled when cells are challenged with pro-oxidants [Sekhar et al., 1997; Liu et al., 1998]. Recently, GCL was identified as a redox-sensing system that is rapidly induced by oxidative stress [Krejsa et al., 2010], which may represent an alternative mechanism for the CLEFMA-induced response (FIG. 25).

Among the genes downregulated by CLEFMA treatment, FOS was the most notable. Members of the FOS family (FOS, FOSB, Fra1 or FOSL1, and Fra2 or FOSL2) are main constituents of the AP-1 heterodimer, acting in conjunction with the JUN family of proteins. AP-1 is a critical transcription factor complex involved in cell proliferation, differentiation, stress, apoptosis, and tumor promotion. Oxidative stress imposed by $H_2O_2$ and the depletion of intracellular GSH may increase AP-1 DNA binding [Meyer et al., 1993]. In contrast, oxidized thioredoxin interferes with this binding [Gaiter et al., 1994]. Whereas Nrf1 and Nrf2 positively regulate the ARE-mediated expression of the NQO1 gene, c-Fos and Fra1 are the negative regulators [Jaiswal, 2004; Venugopal et al., 1996]. Sulforaphane inhibits FOS and upregulates Nrf2 in the chemoprevention of UVB-induced skin cancer [Dickinson et al., 2009]. Taken together, it is plausible that the downregulation of FOS may present a causal mechanism to CLEFMA-induced cell death.

In summary, these results suggest that CLEFMA induces ROS-mediated oxidative stress in H441 cells. Nrf2 appears to drive the oxidative stress response against CLEFMA, but its failure leads to cancer cell death. Genetic signatures similar to those observed in this study have also been noted in other systems. For example, a cinnamon-derived Michael acceptor cinnamic aldehyde has been shown to induce HO-1, SRNX1, and TXNRD1, which leads to a reduction in melanoma cell proliferation, invasiveness, and tumor growth [Cabello et al., 2009; Rahman et al., 2000]. Similarly, 4-hydroxynonenal, a product of oxidative stress, causes significant increases in the expression of the antioxidant enzymes GCLC, AKR1C1, and GSTA4 [Malone et al., 2007].

TABLE 5

The ontologies affected in H441 cells treated with CLEFMA.

| Functional Annotation | Genes in ontology | p-value* |
|---|---|---|
| Oxidation reduction | AKR1B1, AKR1C2, AKR1C3, AKR1C4, ALDH3A2, BLVRB, FTHL3, FTL, G6PD, GCLM, GPX2, GSR, HTATIP2, LOC441282, ME1, NOS3, NQO1, NQO2, PRDX1, SEPX1, TP53I3, TXNRD1, UGDH | 3.50E−12 |
| Aldo/keto reductase | AKR1B1, AKR1C2, AKR1C3, AKR1C4, GCLM, LOC441282 (AKR1B10) | 1.30E−06 |
| NADP or NADPH binding | G6PD, GSR, ME1, NOS3, TP53I3, TXNRD1 | 4.50E−05 |
| Glutathione metabolism | G6PD, GCLC, GCLM, GPX2, GSR, GSTA4 | 1.30E−03 |

*Benjamini-Hochberg corrected

TABLE 6

The ontologies over-represented by up-and downregulated genes affected in H441 cells treated with CLEFMA. Upregulated genes are in bold font.

| Functional Annotation | Genes in ontology | p-value |
|---|---|---|
| Metabolism of glutathione | G6PD, GCLC, GCLM, GSR | 2.99E−05 |
| Cell death | ADM, EPHX1, FTH1, G6PD, GCLC, GCLM, GPC1, GPX2, GSR, HTATIP2, IGFBP3, IKBKG, NCF2, NOS3, NQO1, NQO2, PLEKHF1, PRDX1, RAP1GAP, RASD1, SLC7A11, TXNRD1, ALDH1A3, APP, CDC42EP3, DUSP10, DUSP6, EGR1, EIF2AK3, FOS, IGF1R, IL1R1, LMNB1, PEG10, PLAT, RNF19A, SNX33, TAF9B, TIA1, TNFRSF6B | 9.36E−05 |

TABLE 7

The canonical pathways affected by CLEFMA treatment.
The upregulated genes are in bold font.

| Ingenuity Canonical Pathways | Molecules | p-value |
|---|---|---|
| Nrf2-mediated Oxidative Stress Response | EPHX1, FTH1, FTL, GCLC, GCLM, GPX2, GSR, GSTA4, NQO1, NQO2, PRDX1, SQSTM1, TXNRD1, FOS, EIF2AK3 | 1.00E−11 |

TABLE 7-continued

The canonical pathways affected by CLEFMA treatment.
The upregulated genes are in bold font.

| Ingenuity Canonical Pathways | Molecules | p-value |
|---|---|---|
| Glutathione Metabolism | G6PD, GCLC, GCLM, GPX2, GSR, GSTA4 | 9.33E−06 |
| Pyruvate Metabolism | AKR1B1, AKR1B10, AKR1B15, ALDH3A2, ME1, ALDH1A3 | 3.16E−05 |
| Metabolism of Xenobiotics by Cytochrome P450 | AKR1C2, AKR1C3, AKR1C4, EPHX1, GSTA4, ALDH1A3 | 1.41E−04 |
| Glycerolipid Metabolism | AKR1B1, AKR1B10, AKR1B15, ALDH3A2, GLA, ALDH1A3 | 1.48E−04 |
| Xenobiotic Metabolism Signaling | ABCC3, ALDH3A2, FTL, GCLC, GSTA4, NQO1, NQO2, ALDH1A3, EIF2AK3 | 2.63E−04 |
| Pentose and Glucuronate Interconversions | AKR1B1, AKR1B10, AKR1B15, UGDH | 4.37E−04 |

Thus, in accordance with the present inventive concept(s), there have been provided antiproliferative compositions and methods of making and using same that fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Adams B K, Cai J, Armstrong J, Herold M, Lu Y J, Sun A, Snyder J P, Liotta D C, Jones D P, Shoji M (2005) Anticancer Drugs 16:263-275.
Adams B K, Ferstl E M, Davis M C, Herold M, Kurtkaya S, Camalier R F, Hollingshead M G, Kaur G, Sausville E A, Rickles F R, Snyder J P, Liotta D C, Shoji M (2004) Bioorg Med Chem 12:3871-3883.
Adams, B. K., E. M. Ferstl, M. C. Davis, M. Herold, S. Kurtkaya, R. F. Camalier, M. G. Hollingshead, G. Kaur, E. A. Sausville, F. R. Rickles, J. P. Snyder, D. C. Liotta, M. Shoji, Bioorg. Med. Chem., 12 (2004) 3871.
Agashe, H., P. Lagisetty, K. Sahoo, D. Bourne, B. Grady, V. Awasthi, J. Nanopart. Res., In press (2010) DOI 10.1007/s11051-010-0154-5.
Agashe, H., P. Lagisetty, S. Awasthi, V. Awasthi, Colloids Surf., B, 75 (2009) 573.
Akerley, W., H. Choy, Semin. Radiat. Oncol., 9 (1999) 85.
Altar, C. A., Clin. Pharmacol. Ther., 83 (2008) 361.
Anand, P.; Kunnumakkara, A. B.; Newman, R. A.; Aggarwal, B. B. Mol Pharm 2007, 4, 807.
Artico, M.; Di Santo, R.; Costi, R.; Novellino, E.; Greco, G.; Massa, S.; Tramontano, E.; Marongiu, M. E.; De Montis, A.; La Colla, P. J Med Chem 1998, 41, 3948.
Asher G, Lotem J, Kama R, Sachs L, Shaul Y (2002) Proc Natl Acad Sci USA 99:3099-3104.
Awasthi, V., B. Goins, L. McManus, R. Klipper, W. T. Phillips, Nucl. Med. and Biol., 30 (2003) 159.
Awasthi, V., B. Goins, R. Klipper, R. Loredo, D. Korvick, W. T. Phillips, J. Nucl. Med., 39 (1998) 1089.
Awasthi, V., S. H. Yee, P. Jerabek, B. Goins, W. T. Phillips, J. Appl. Physiol., 103 (2007) 28.
Awasthi, V. D., B. Goins, R. Klipper, W. T. Phillips, J. Drug Targeting, 10 (2002) 419.
Awasthi, V. D., B. Goins, W. T. Phillips, Am. J. Pharmacol. Toxicol., 2 (2007) 98.
Awasthi, V. D., D. Garcia, B. A. Goins, W. T. Phillips, Int. J. Pharm., 253 (2003) 121.
Awasthi, V. D., D. Garcia, R. Klipper, B. A. Goins, W. T. Phillips, J. Pharmacol. Exp. Ther., 309 (2004) 241.
Behrend L, Henderson G, Zwacka R M (2003) Biochem Soc Trans 31:1441-1444.
Bergmann, A., Cell, 131 (2007) 1032.
Biederbick, A.; Kern, H. F.; Elsasser, H. P. EurJ Cell Biol 1995, 66, 3.
Burczynski M E, Lin H K, Penning T M (1999) Cancer research 59:607-614.
Burczynski M E, Sridhar G R, Palackal N T, Penning T M (2001) J Biol Chem 276:2890-2897.
Burdett, S. S.; Stewart, L. A.; Rydzewska, L. Cochrane Database Syst Rev (2007), CD006157.
Cabello C M, Bair W B, Lamore S D, Ley S, Bause A S, Azimian S, Wondrak G T (2009) Free Radic Biol Med 46:220-231.
Chen Y, McMillan-Ward E, Kong J, lsraels S J, Gibson S B (2008) Cell death and differentiation 15:171-182.
Costi R, Santo R D, Artico M, Massa S, Ragno R, Loddo R, La Colla M, Tramontano E, La Colla P, Pani A (2004) Bioorg Med Chem 12:199-215.
Danesi, R., G. Pasqualetti, E. Giovannetti, F. Crea, G. Altavilla, M. Del Tacca, R. Rosell, Adv. Drug Delivery Rev., 61 (2009) 408.
Das, S.; Das, U.; Selvakumar, P.; Sharma, R. K.; Balzarini, J.; De Clercq, E.; Molnar, J.; Serly, J.; Barath, Z.; Schatte, G.; Bandy, B.; Gorecki, D. K.; Dimmock, J. R. ChemMedChem 2009, 4, 1831.
Das, U.; Alcorn, J.; Shrivastav, A.; Sharma, R. K.; De Clercq, E.; Balzarini, J.; Dimmock, J. R. Eur J Med Chem 2007, 42, 71.
Das, U.; Das, S.; Bandy, B.; Stables, J. P.; Dimmock, J. R. Bioorg Med Chem 2008, 16, 3602.
Das, U.; Molnar, J.; Barath, Z.; Bata, Z.; Dimmock, J. R. Bioorg Med Chem Lett 2008, 18, 3484.
Dempke, W. C., T. Suto, M. Reck, Lung Cancer, 67 (2010) 257.
Dennis G, Sherman B T, Hosack D A, Yang J, Gao W, Lane H C, Lempicki R A (2003) Genome Biol 4:P3.
Dickinson S E, Melton T F, Olson E R, Zhang J, Saboda K, Bowden G T (2009) Cancer research 69:7103-7110.
Dimmock, J. R.; Arora, V. K.; Wonko, S. L.; Hamon, N. W.; Quail, J. W.; Jia, Z.; Warrington, R. C.; Fang, W. D.; Lee, J. S. Drug Des Deliv 1990, 6, 183.
Dimmock, J. R.; Kandepu, N. M.; Nazarali, A. J.; Kowalchuk, T. P.; Motaganahalli, N.; Quail, J. W.; Mykytiuk, P. A.; Audette, G. F.; Prasad, L.; Perjesi, P.; Allen, T. M.; Santos, C. L.; Szydlowski, J.; De Clercq, E.; Balzarini, J. J Med Chem 1999, 42, 1358.
Dimmock, J. R.; Padmanilayam, M. P.; Puthucode, R. N.; Nazarali, A. J.; Motaganahalli, N. L.; Zello, G. A.; Quail, J. W.; Oloo, E. O.; Kraatz, H. B.; Prisciak, J. S.; Allen, T. M.; Santos, C. L.; Balzarini, J.; De Clercq, E.; Manavathu, E. K. J Med Chem 2001, 44, 586.
Dimmock, J. R.; Padmanilyam, M. P.; Zello, G. A.; Quail, J. W.; Oloo, E. O.; Prisciak, J. S.; Kraatz, H. B.; Cherkasov, A.; Lee, J. S.; Allen, T. M.; Santos, C. L.; Manavathu, E. K.; De Clercq, E.; Balzarini, J.; Stables, J. P. Eur J Med Chem 2002, 37, 813.

Dozmorov I, Knowlton N, Tang Y, Shields A, Pathipvanich P, Jarvis J N, Centola M (2004) Nucleic Acids Res 32:e147.

Dozmorov I, Lefkovits I (2009) Nucleic Acids Res 37:6323-6339.

Du Z Y, Liu R R, Shao W Y, Mao X P, Ma L, Gu L Q, Huang Z S, Chan A S (2006) European journal of medicinal chemistry 41:213-218.

Dubey, S.; Powell, C. A. Am J Respir Crit. Care Med 2009, 179, 860.

Eberhart, C. E.; Coffey, R. J.; Radhika, A.; Giardiello, F. M.; Ferrenbach, S.; DuBois, R. N. Gastroenterology 1994, 107, 1183.

El-Subbagh, H. I.; Abu-Zaid, S. M.; Mahran, M. A.; Badria, F. A.; Al-Obaid, A. M. J Med Chem 2000, 43, 2915.

Fang J, Seki T, Maeda H (2009) Adv Drug Deliv Rev 61:290-302.

Frank, D. W., in E. C. J. Melby (Ed.), Handbook of Laboratory Animal Science, CRC Press, Boca Raton, Fla., 1976, 23.

Furuta S, Hidaka E, Ogata A, Yokota S, Kamata T (2004) Oncogene 23:3898-3904.

Gaiter D, Mihm S, Droge W (1994) Eur J Biochem 221:639-648.

Gibellini L, Pinti M, Nasi M, Biasi S D, Roat E, Bertoncelli L, Cossarizza A (2010) Cancers 2:1288-1311.

Gregoriadis, G., in D. D. Lasic and F. Martin (Eds.), Stealth Liposomes, CRC Press, Boca Raton, Fla., 1995, Chapter 2.

Gridelli, C., A. Ardizzoni, J. Y. Douillard, N. Hanna, C. Manegold, F. Perrone, R. Pirker, R. Rosell, F. A. Shepherd, L. De Petris, M. Di Maio, F. de Marinis, Lung Cancer, 68 (2010) 319.

Guo X, Shin V Y, Cho C H (2001) Life Sci 69:3113-3119.

Herbst R S, Heymach J V, Lippman S M (2008) The New England journal of medicine 359:1367-1380.

Higuchi, T., K. Connors, Adv. Anal. Chem. Instrum., 4 (1965) 127

Hileman E O, Liu J, Albitar M, Keating M J, Huang P (2004) Cancer Chemother Pharmacol 53:209-219.

Homolya L, Varadi A, Sarkadi B (2003) Biofactors 17:103-114.

Huang C L, Yokomise H, Miyatake A (2007) Future oncology (London, England) 3:83-93.

Huncharek M, Muscat J, Geschwind J F (1999) Carcinogenesis 20:1507-1510.

Huwyler, J., J. Drewe, S. Krahenbuhl, Int. J. Nanomedicine, 3 (2008) 21.

Itoh K, Chiba T, Takahashi S, Ishii T, Igarashi K, Katoh Y, Oyake T, Hayashi N, Satoh K, Hatayama I, Yamamoto M, Nabeshima Y (1997) Biochem Biophys Res Commun 236:313-322.

Jaiswal A K (2000) Free Radic Biol Med 29:254-262.

Jaiswal A K (2004) Free Radic Biol Med 36:1199-1207.

Jia, Z.; Quail, J. W. Acta Cryst. 1988, C44, 2114.

Joseph P, Long D J, 2nd, Klein-Szanto A J, Jaiswal A K (2000) Biochem Pharmacol 60:207-214.

Kaasgaard, T., T. L. Andresen, Expert Opin. Drug Deliv., 7225.

Kasinski A L, Du Y, Thomas S L, Zhao J, Sun S Y, Khuri F R, Wang C Y, Shoji M, Sun A, Snyder J P, Liotta D, Fu H (2008) Molecular pharmacology 74:654-661.

Kasinski, A. L.; Du, Y.; Thomas, S. L.; Zhao, J.; Sun, S. Y.; Khuri, F. R.; Wang, C. Y.; Shoji, M.; Sun, A.; Snyder, J. P.; Liotta, D.; Fu, H. Mol Pharmacol 2008, 74, 654.

Kaur, N., R. Puri, S. K. Jain, AAPS PharmSciTech, 11 (2010) 528.

Konig J, Nies A T, Cui Y, Leier I, Keppler D (1999) Biochim Biophys Acta 1461:377-394.

Krejsa C M, Franklin C C, White C C, Ledbetter J A, Schieven G L, Kavanagh T J (2010) J Biol Chem 285:16116-16124.

Lagisetty P, Powell D R, Awasthi V (2009) J Mol Str 936:23-28.

Lagisetty P, Vilekar P, Sahoo K, Anant S, Awasthi V (2010) Bioorg Med Chem 18:6109-6120 (incorporated herein as Example 1).

Landais, I.; Hiddingh, S.; McCarroll, M.; Yang, C.; Sun, A.; Turker, M. S.; Snyder, J. P.; Hoatlin, M. E. Mol Cancer 2009, 8, 133.

Landegren U (1984) J Immunol Methods 67:379-388.

Landegren, U., J. Immunol. Methods, 67 (1984) 379.

Lee J S, Yoon A, Kalapurakal S K, Ro J Y, Lee J J, Tu N, Hittelman W N, Hong W K (1995) J Clin Oncol 13:1893-1903.

Lee Y J, Shacter E (1999) J Biol Chem 274:19792-19798.

Lelli J L, Becks L L, Dabrowska M I, Hinshaw D B (1998) Free Radic Biol Med 25:694-702.

Lennon S V, Martin S J, Cotter T G (1991) Cell Prolif 24:203-214.

Lev-Ari S, Starr A, Vexler A, Karaush V, Loew V, Greif J, Fenig E, Aderka D, Ben-Yosef R (2006) Anticancer research 26:4423-4430.

Leyon, P. V.; Kuttan, G. J Exp Clin Cancer Res 2003, 22, 77.

Liu R M, Gao L, Choi J, Forman H J (1998) Am J Physiol 275:L861-869.

Lock, R. B.; Stribinskiene, L. Cancer Res 1996, 56, 4006.

Maeda, H., K. Greish, J. Fang, Adv. Polym. Sci., 193 (2006) 103.

Malone P E, Hernandez M R (2007) Exp Eye Res 84:444-454.

Mantovani, A. Current molecular medicine-10, 369.

Matsko, N.; Mueller, M. J Struct Biol 2005, 152, 92.

McCormack, B., G. Gregoriadis, J. Drug Targeting, 2 (1994) 449.

Meyer M, Schreck R, Baeuerle P A (1993) The EMBO journal 12:2005-2015.

Meylan E, Dooley A L, Feldser D M, Shen L, Turk E, Ouyang C, Jacks T (2009) Nature 462:104-107.

Modzelewska A, Pettit C, Achanta G, Davidson N E, Huang P, Khan S R (2006) Bioorg Med Chem 14:3491-3495.

Morse, D. L.; Gray, H.; Payne, C. M.; Gillies, R. J. Mol. Cancer Ther 2005, 4, 1495.

Mosley, C. A.; Liotta, D. C.; Snyder, J. P. Adv Exp Med Biol 2007, 595, 77.

Mulcahy R T, Gipp 11 (1995) Biochem Biophys Res Commun 209:227-233.

Nguyen T, Sherratt P J, Pickett C B (2003) Annu Rev Pharmacol Toxicol 43:233-260.

Niklinski J, Niklinska W, Laudanski J, Chyczewska E, Chyczewski L (2001) Lung cancer (Amsterdam, Netherlands) 34 Suppl 2:S53-58.

Niklinski, J.; Niklinska, W.; Laudanski, J.; Chyczewska, E.; Chyczewski, L. Lung Cancer 2001, 34 Suppl 2, S53.

O'Dwyer P J, LaCreta F P, Haas N B, Halbherr T, Frucht H, Goosenberg E, Yao K S (1994) Cancer Chemother Pharmacol 34 Suppl:S46-52.

Pastore A, Piemonte F, Locatelli M, Lo Russo A, Gaeta L M, Tozzi G, Federici G (2001) Clin Chem 47:1467-1469.

Pati H N, Das U, Quail J W, Kawase M, Sakagami H, Dimmock J R (2008) European journal of medicinal chemistry 43:1-7.

Pati, H. N.; Das, U.; Das, S.; Bandy, B.; De Clercq, E.; Balzarini, J.; Kawase, M.; Sakagami, H.; Quail, J. W.; Stables, J. P.; Dimmock, J. R. EurJ Med Chem 2009, 44, 54.

Penning T M, Drury J E (2007) Arch Biochem Biophys 464: 241-250.

Petty, C., Research Techniques in the Rats, Charles C. Thomas, Springfield, I L, 1982.

Phillips, W. T., A. S. Rudolph, B. Goins, J. H. Timmons, R. Klipper, R. Blumhardt, Nucl. Med. Biol., 19 (1992) 539.

Pink J J, Planchon S M, Tagliarino C, Varnes M E, Siegel D, Boothman D A (2000) J Biol Chem 275:5416-5424.

Rahman I, MacNee W (2000) Free Radic Biol Med 28:1405-1420.

Rahman, M. A.; Kelly, D. R.; Srivastava, R. M.; Fraser-Reid, B. Carbohydr Res 1985, 136, 91.

Raiser M, Wamelink M M, Kowald A, Gerisch B, Heeren G, Struys E A, Klipp E, Jakobs C, Breitenbach M, Lehrach H, Krobitsch S (2007) J Biol 6:10.

Reddy, P. G.; Kishore Kumar, G. D.; Baskaran, S. Tetrahedron Lett 2000, 41, 9149.

Rein, D. T.; Schondorf, T.; Breidenbach, M.; Janat, M. M.; Weikelt, A.; Gohring, U. J.; Becker, M.; Mallmann, P.; Kurbacher, C. M. Anticancer Res 2000, 20, 5069.

Ricciardi, S., S. Tomao, F. de Marinis, Clin. Lung Cancer, 10 (2009) 28.

Roberson, E. D.; Mucke, L. Science 2006, 314, 781.

Robinson T P, Hubbard R B, Ehlers T J, Arbiser J L, Goldsmith D J, Bowen J P (2005) Bioorg Med Chem 13:4007-4013.

Rushmore T H, King R G, Paulson K E, Pickett C B (1990) Proc Natl Acad Sci USA 87:3826-3830.

Samad, A., Y. Sultana, M. Aqil, Curr. Drug Delivery, 4 (2007) 297.

Scherz-Shouval R, Shvets E, Fass E, Shorer H, Gil L, Elazar Z (2007) The EMBO journal 26:1749-1760.

Schettino, C., M. A. Bareschino, P. Maione, A. Rossi, F. Ciardiello, C. Gridelli, Curr. Genomics, 9 (2008) 252.

Schwendener, R. A., Advances in Experimental Medicine and Biology, 620 (2007) 117.

Seglen, P. O.; Gordon, P. B. Proc Natl Acad Sci USA 1982, 79, 1889.

Sekhar K R, Long M, Long J, Xu Z Q, Summar M L, Freeman M L (1997) Radiat Res 147:592-597.

Selvendiran K, Tong L, Vishwanath S, Bratasz A, Trigg N J, Kutala V K, Hideg K, Kuppusamy P (2007) J Biol Chem 282:28609-28618.

Singh A, Ling G, Suhasini A N, Zhang P, Yamamoto M, Navas-Acien A, Cosgrove G, Tuder R M, Kensler T W, Watson W H, Biswal S (2009) Free Radic Biol Med 46:376-386.

Singh, S.; Khar, A. Anti-cancer agents in medicinal chemistry 2006, 6, 259.

Snyder, J. P.; Davis, M. C.; Adams, B.; Shoji, M.; Liotta, D. C.; Ferstl, E. M.; Sunay, U. B. United States Patent WO 2001/040188 2003.

Snyder, J. P.; Davis, M., C.; Adams, B.; Shoji, M.; Liotta, D. C.; Ferstl, E. M.; Sunay, U. B. U.S. Pat. No. 6,664,272 2008.

Snyder, J. P.; Davis, M., C.; Adams, B.; Shoji, M.; Liotta, D. C.; Ferstl, E. M.; Sunay, U. B. US Patent 2008/0234230 A1 2008.

Stewart, J. C., Anal. Biochem., 104 (1980) 10.

Subramaniam D, May R, Sureban S M, Lee K B, George R, Kuppusamy P, Ramanujam R P, Hideg K, Dieckgraefe B K, Houchen C W, Anant S (2008) Cancer research 68:1962-1969.

Sun A, Lu Y J, Hu H, Shoji M, Liotta D C, Snyder J P (2009) Bioorg Med Chem Lett 19:6627-6631.

Sun A, Shoji M, Lu Y J, Liotta D C, Snyder J P (2006) J Med Chem 49:3153-3158.

Sun, A.; Lu, Y. J.; Hu, H.; Shoji, M.; Liotta, D. C.; Snyder, J. P. Bioorg Med Chem Lett 2009, 19, 6627.

Thomas, S. L.; Zhong, D.; Zhou, W.; Malik, S.; Liotta, D.; Snyder, J. P.; Hamel, E.; Giannakakou, P. Cell Cycle 2008, 7, 2409.

Thomas, S. L., J. Zhao, Z. Li, B. Lou, Y. Du, J. Purcell, J. P. Snyder, F. R. Khuri, D. Liotta, H. Fu, Biochem. Pharmacol., 80 (2010) 1309.

Trachootham D, Alexandre J, Huang P (2009) Nature reviews 8:579-591.

Tsuboi, M.; Kato, H. Gan To Kagaku Ryoho 2007, 34, 1538.

Venugopal R, Jaiswal A K (1996) Proc Natl Acad Sci USA 93:14960-14965.

Westerhoff, O.; Lutzen, A.; Maison, W.; Kosten, M. J. Chem. Soc., Perkin Trans 1 2001, 508.

Wondrak G T (2009) Antioxid Redox Signal 11:3013-3069.

Woodcock, J., R. Woosley, Ann. Rev. Med., 59 (2008)$_1$.

Wouters, B. G.; Giaccia, A. J.; Denko, N. C.; Brown, J. M. Cancer Res 1997, 57, 4703.

Yang H, Wang J, Huang Z Z, Ou X, Lu S C (2001) Biochem J 357:447-455.

Yang H, Wang J, Ou X, Huang Z Z, Lu S C (2001) Biochem Biophys Res Commun 285:476-482.

Youssef, D.; Potter, E.; Jha, M.; De Clercq, E.; Balzarini, J.; Stables, J. P.; Jha, A. Bioorg Med Chem Lett 2009, 19, 6364.

What is claimed is:

1. A curcumin analog composition, comprising 4-[3,5-bis(2-chlorobenzylidene-4-oxo-piperidine-1-yl)-4-oxo-2-butenoic acid] (CLEFMA).

2. The curcumin analog composition of claim 1, further comprising 2-hydroxypropyl-beta-cyclodextrin (HPβCD).

3. The curcumin analog composition of claim 1, further comprising glutathione.

4. The curcumin analog composition of claim 1, further comprising at least one additional molecule/agent selected from the group consisting of a Cox-2 inhibitor, an anti-cancer agent, an anti-inflammatory agent, an anti-oxidant, a targeting moiety, a polyethylene glycol molecule, a labeling moiety, and combinations thereof.

5. A liposomal composition comprising:
a lipid composition; and
a curcumin analog composition comprising 4-[3,5-bis(2-chlorobenzylidene-4-oxo-piperidine-1-yl)-4-oxo-2-butenoic acid] (CLEFMA) encapsulated within a liposomal structure formed by the lipid composition.

6. The liposomal composition of claim 5, wherein the lipid composition is further defined as an anionic non-phospholipid having the structure represented by the following general formula [1]:

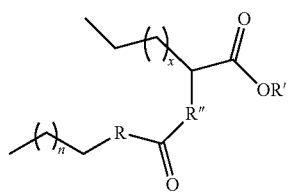

wherein R is NH or O; R' is at least one of a hydrogen (H), an alkyl group (such as but not limited to, methyl, ethyl, propyl, butyl, pentyl, hexyl, heptyl, octyl, nonyl, decyl, undecyl, dodecyl, hexadecyl), Na, Li, K, a metal, or a halogen; R" is at least one of a —CH$_2$— group and a —CH$_2$CH$_2$— group; and n and x are each an 8-16 carbon chain.

7. The liposomal composition of claim 6, wherein the lipid composition is selected from the group consisting of 2-carboxyheptadecanoyl heptadecylamide (CHHDA); 1,4-dipalmitoyl-tartarate-2,3-disuccinic acid (DPTSA); 1,4-dipalmitoyl-tartarate-2,3-diglutaric acid (DPTGA); 1,4-disteroyl-tartarate-2,3-disuccinic acid (DSTSA); and cholesteryl hemisuccinate (CHEMS).

8. The liposomal composition of claim 6, further comprising at least one additional lipid composition is selected from the group consisting of phosphatidylcholine, phosphoethanolamine, phosphatidylglycerol, and a sterol lipid.

9. The liposomal composition of claim 6, wherein the anionic non-phospholipid is present in a range of from about 1% to about 30% of the total lipid present in the liposomal structure, and wherein the liposomal structure comprises a particle size in a range of from about 50 nm to about 500 nm, and a volume average particle size in a range of from about 10 nm to about 5,000 nm.

10. The liposomal composition of claim 5, further comprising at least one molecule/agent selected from the group consisting of 2-hydroxypropyl-beta-cyclodextrin (HPβCD), glutathione, a Cox-2 inhibitor, an anti-cancer agent, an anti-inflammatory agent, an anti-oxidant, a targeting moiety, a polyethylene glycol molecule, a labeling moiety, and combinations thereof.

11. A method of forming a liposomal composition, comprising the steps of:
disposing an anionic non-phospholipid composition and a curcumin analog composition in an aqueous solution, wherein the curcumin analog composition comprises 4-[3,5-bis(2-chlorobenzylidene-4-oxo-piperidine-1-yl)-4-oxo-2-butenoic acid] (CLEFMA), and wherein the anionic non-phospholipid composition has the structure represented by the following general formula [1]:

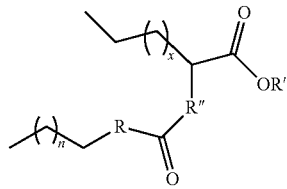

wherein R is NH or O; R' is at least one of a hydrogen (H), an alkyl group (such as but not limited to, methyl, ethyl, propyl, butyl, pentyl, hexyl, heptyl, octyl, nonyl, decyl, undecyl, dodecyl, hexadecyl), Na, Li, K, a metal, or a halogen; R" is at least one of a —CH$_2$— group and a —CH$_2$CH$_2$— group; and n and x are each an 8-16 carbon chain; and
dispersing same to form the liposomal structure having the curcumin analog composition encapsulated therein.

* * * * *

UNITED STATES PATENT AND TRADEMARK OFFICE
CERTIFICATE OF CORRECTION

PATENT NO. : 9,359,196 B2
APPLICATION NO. : 13/279766
DATED : June 7, 2016
INVENTOR(S) : Vibhudutta Awasthi, Pallavi Lagisetty and Hrushikesh Agashe It is certified that error appears in the above-identified patent and that said Letters Patent is hereby corrected as shown below:

In the Specification:
Column 11, line 23: Delete "HP(3CD)." and replace with -- HPβCD), --
Column 14, line 14: Delete "-5-transferase," and replace with -- S-transferase, --
Column 19, line 37: Delete "E1-" and replace with -- El- --
Column 19, line 44: Delete "CH NMR)." and replace with -- ($^1$H NMR). --
Column 22, line 6: Delete "E1-" and replace with -- El- --
Column 22, line 23: Delete "E1-" and replace with -- El- --
Column 25, line 31: Delete "multiples," and replace with -- multiplet, --
Column 25, line 41: Delete "MeI-Temp" and replace with -- Mel-Temp --
Column 31, line 22: Delete "NC1" and replace with -- NCl --
Column 42, line 37: Delete "NC1-H441" and replace with -- NCl-H441 --
Column 43, line 2: Delete "E-well" and replace with -- 6-well --
Column 48, line 52: Delete "3-lapachone," and replace with -- β-lapachone, --
Column 48, line 65: Delete "sulfuredoxin" and replace with -- sulfiredoxin --
Column 49, line 64: Delete "[Gaiter" and replace with -- [Galter --
Column 53, line 17: Delete "E1-Subbagh," and replace with -- El-Subbagh, --

Signed and Sealed this
Twelfth Day of July, 2016

Michelle K. Lee
*Director of the United States Patent and Trademark Office*